(12) United States Patent
Salverda et al.

(10) Patent No.: US 11,040,010 B2
(45) Date of Patent: Jun. 22, 2021

(54) SURFACE DISPLAY OF ANTIGENS ON GRAM-NEGATIVE OUTER MEMBRANE VESICLES

(71) Applicant: De Staat der Nederlanden, vert. door de minister van VWS, Ministerie van Volksgezondheid, Welzijn en, The Hague (NL)

(72) Inventors: Merijn Louis Marten Salverda, Amsterdam (NL); Peter André van der Ley, Utrecht (NL)

(73) Assignee: De Staat der Nederlanden, vert. door de minister van VWS, Ministerie van Volksgezondheid, Welzijn en Sport, The Hague (NL)

( * ) Notice: Subject to any disclaimer, the term of this patent is extended or adjusted under 35 U.S.C. 154(b) by 25 days.

(21) Appl. No.: 16/702,660

(22) Filed: Dec. 4, 2019

(65) Prior Publication Data

US 2020/0197308 A1    Jun. 25, 2020

Related U.S. Application Data

(62) Division of application No. 15/578,639, filed as application No. PCT/EP2016/062494 on Jun. 2, 2016, now Pat. No. 10,639,280.

(30) Foreign Application Priority Data

Jun. 2, 2015 (EP) ..................................... 15170307

(51) Int. Cl.

| | | |
|---|---|---|
| *A01N 63/00* | (2020.01) | |
| *A61K 9/127* | (2006.01) | |
| *C07K 14/20* | (2006.01) | |
| *C07K 14/22* | (2006.01) | |
| *C07K 14/245* | (2006.01) | |
| *C07K 14/235* | (2006.01) | |
| *C07K 14/255* | (2006.01) | |
| *A61K 39/02* | (2006.01) | |
| *A61K 39/095* | (2006.01) | |
| *A61P 31/00* | (2006.01) | |
| *A61P 35/00* | (2006.01) | |
| *A61K 39/00* | (2006.01) | |
| *A61K 35/74* | (2015.01) | |

(52) U.S. Cl.
CPC ........ *A61K 9/1275* (2013.01); *A61K 39/0225* (2013.01); *A61K 39/095* (2013.01); *A61P 31/00* (2018.01); *A61P 35/00* (2018.01); *C07K 14/20* (2013.01); *C07K 14/22* (2013.01); *C07K 14/235* (2013.01); *C07K 14/245* (2013.01); *C07K 14/255* (2013.01); *A61K 35/74* (2013.01); *A61K 39/00* (2013.01); *A61K 2039/523* (2013.01); *A61K 2039/6068* (2013.01); *A61K 2039/70* (2013.01); *C07K 2319/00* (2013.01); *Y02A 50/30* (2018.01)

(58) Field of Classification Search
CPC .................................................... A61K 9/1275
See application file for complete search history.

(56) References Cited

U.S. PATENT DOCUMENTS

| | | |
|---|---|---|
| 5,777,095 A | 7/1998 | Barbour et al. |
| 2012/0107339 A1 | 5/2012 | Granoff et al. |

FOREIGN PATENT DOCUMENTS

| | | |
|---|---|---|
| WO | WO2004048404 A2 | 6/2004 |
| WO | WO2009114207 A2 | 9/2009 |
| WO | WO2012041899 A1 | 4/2012 |
| WO | WO2013098589 A1 | 7/2013 |
| WO | WO2014044728 A1 | 3/2014 |

OTHER PUBLICATIONS

Kumru OS. Surface localization determinants of Borrelia burgdorferi lipoproteins. Kansas: University of Kansas; 2011.

Van der Ley P, Steeghs L, Hamstra HJ, ten Hove J, Zomer B, van Alphen L. Modification of lipid A biosynthesis in Neisseria meningitidis lpxL mutants: influence on lipopolysaccharide structure, toxicity, and adjuvant activity. Infection and immunity. 2001;69(10):5981-90.

Van der Voort ER, van der Ley P, van der Biezen J, George S, Tunnela O, van Dijken H, et al. Specificity of human bactericidal antibodies against PorA P1.7,16 induced with a hexavalent meningococcal outer membrane vesicle vaccine. Infection and immunity. 1996;64(7):2745-51.

Bos MP, Tefsen B, Geurtsen J, Tommassen J. Identification of an outer membrane protein required for the transport of lipopolysaccharide to the bacterial cell surface. Proceedings of the National Academy of Sciences of the United States of America. 2004;101(25):9417-22.

(Continued)

*Primary Examiner* — Albert M Navarro
(74) *Attorney, Agent, or Firm* — N.V. Nederlandsch Octrooibureau; Tamara C. Stegmann; Catherine A. Shultz

(57) ABSTRACT

The present invention relates to vaccine compositions based on Gram-negative outer membrane vesicles displaying antigens of pathogens expressed as part of a fusion protein comprising N-terminal parts of surface expressed lipoproteins of Gram-negative bacteria, and use of such compositions in vaccination. The invention further relates to the fusion lipoproteins comprising N-terminal parts of surface expressed lipoproteins of Gram-negative bacteria and antigens of pathogens fused thereto, DNA constructs and bacterial host cells for expressing these fusion lipoproteins and to methods for producing outer membrane vesicles displaying the fusion lipoproteins.

16 Claims, 19 Drawing Sheets

Specification includes a Sequence Listing.

(56) References Cited

OTHER PUBLICATIONS

Grizot S, Buchanan SK. Structure of the OmpA-like domain of RmpM from Neisseria meningitidis. Molecular microbiology. 2004;51(4):1027-37.
Li H, Dunn JJ, Luft BJ, Lawson CL. Crystal structure of Lyme disease antigen outer surface protein A complexed with an Fab. Proceedings of the National Academy of Sciences of the United States of America. 1997;94(8):3584-9.
Oriente F, Scarlato V, Delany I. Expression of factor H binding protein of meningococcus responds to oxygen limitation through a dedicated FNR-regulated promoter. Journal of bacteriology. 2010;192(3):691-701.
Chen S, Zuckert WR. Probing the Borrelia burgdorferi surface lipoprotein secretion pathway using a conditionally folding protein domain. Journal of bacteriology. 2011;193(23):6724-32.
Lee JS, Shin KS, Pan JG, Kim CJ. Surface-displayed viral antigens on *Salmonella* carrier vaccine. Nature biotechnology. 2000;18(6):645-8.
Rizos K, Lattemann CT, Bumann D, Meyer TF, Aebischer T. Autodisplay: efficacious surface exposure of antigenic UreA fragments from Helicobacter pylori in *Salmonella* vaccine strains. Infection and immunity. 2003;71(11):6320-8.
Lee SJ, Liang L, Juarez S, Nanton MR, Gondwe EN, Msefula CL, et al. Identification of a common immune signature in murine and human systemic Salmonellosis. Proceedings of the National Academy of Sciences of the United States of America. 2012;109(13):4998-5003.
Cote-Sierra J, Bredan A, Toldos CM, Stijlemans B, Brys L, Cornelis P, et al. Bacterial lipoprotein-based vaccines induce tumour necrosis factor-dependent type 1 protective immunity against Leishmania major. Infection and immunity. 2002;70(1):240-8.
Earnhart CG, Buckles EL, Dumler JS, Marconi RT. Demonstration of OspC type diversity in invasive human lyme disease isolates and identification of previously uncharacterized epitopes that define the specificity of the OspC murine antibody response. Infection and immunity. 2005;73(12):7869-77.
Steere AC, Livey I. Lyme disease vaccines. In: Plotkin SA, Orenstein WA, Offit PA, editors. Vaccines. 6th ed: Saunders, and imprint of Elsevier Inc.; 2013. p. 1122-32.
Probst C, Ott A, Scheper T, Meyer W, Stocker W, Komorowski L. N-terminal disulfide-bridging of Borrelia outer surface protein C increases its diagnostic and vaccine potentials. Ticks and tick-borne diseases. 2012;3(1):1-7.
Eicken C, Sharma V, Klabunde T, Owens RT, Pikas DS, Hook M, et al. Crystal structure of Lyme disease antigen outer surface protein C from Borrelia burgdorferi. The Journal of biological chemistry. 2001;276(13)10010-5.
Buckles EL, Earnhart CG, Marconi RT. Analysis of antibody response in humans to the type A OspC loop 5 domain and assessment of the potential utility of the loop 5 epitope in Lyme disease vaccine development. Clinical and vaccine immunology : CVI. 2006,13(10):1162-5.
Ellis TN, Kuehn MJ. Virulence and immunomodulatory roles of bacterial outer membrane vesicles. Microbiology and molecular biology reviews : MMBR. 2010;74(1):81-94.
Chen DJ, Osterrieder N, Metzger SM, Buckles E, Doody AM, DeLisa MP, et al. Delivery of foreign antigens by engineered outer membrane vesicle vaccines. Proceedings of the National Academy of Sciences of the United States of America. 2010;107(7):3099-104.
Muralinath M, Kuehn MJ, Roland KL, Curtiss R, 3rd. Immunization with *Salmonella enterica* serovar Typhimurium-derived outer membrane vesicles delivering the pneumococcal protein PspA confers protection against challenge with *Streptococcus pneumoniae*. Infection and immunity. 2011;79(2):887-94.
Gaillard ME, Bottero, D., Errea, A. Acellular pertussis vaccine based on outer membrane vesicles capable of conferring both long-lasting immunity and protection against different strain genotypes. Vaccine. 2014;32:931-7.
Zollinger WD, Donets MA, Schmiel DH, Pinto VB, Labrie JE, 3rd, Moran EE, et al. Design and evaluation in mice of a broadly protective meningococcal group B native outer membrane vesicle vaccine. Vaccine. 2010;28(31):5057-67.
Nieves W, Petersen H, Judy BM, Blumentritt CA, Russell-Lodrigue K, Roy CJ, et al. A Burkholderia pseudomallei outer membrane vesicle vaccine provides protection against lethal sepsis. Clinical and vaccine immunology : CVI. 2014;21(5):747-54.
Camacho AI, de Souza J, Sanchez-Gomez S, Pardo-Ros M, Irache JM, Gamazo C. Mucosal immunization with Shigella flexneri outer membrane vesicles induced protection in mice. Vaccine. 2011;29(46):8222-9.
Kim OY, Hong BS, Park KS, Yoon YJ, Choi SJ, Lee WH, et al. Immunization with *Escherichia coli* outer membrane vesicles protects bacteria-induced lethality via Th1 and Th17 cell responses. J Immunol. 2013;190(8):4092-102.
Keenan JI, Rijpkema SG, Durrani Z, Roake JA. Differences in immunogenicity and protection in mice and guinea pigs following intranasal immunization with Helicobacter pylori outer membrane antigens. FEMS immunology and medical microbiology. 2003;36(3):199-205.
Roberts R, Moreno G, Bottero D, Gaillard ME, Fingermann M, Graieb A, et al. Outer membrane vesicles as acellular vaccine against pertussis. Vaccine. 2008;26(36):4639-46.
Bartolini E, Ianni E, Frigimelica E, Petracca R, Galli G, Berlanda Scorza F, et al. Recombinant outer membrane vesicles carrying Chlamydia muridarum HtrA induce antibodies that neutralize chlamydial infection in vitro. Journal of extracellular vesicles. 2013;2.
Holst J, Martin D, Arnold R, Huergo CC, Oster P, O'Hallahan J, et al. Properties and clinical performance of vaccines containing outer membrane vesicles from Neisseria meningitidis. Vaccine. 2009;27 Suppl 2:B3-12.
Nokleby H, Aavitsland P, O'Hallahan J, Feiring B, Tilman S, Oster P. Safety review: two outer membrane vesicle (OMV) vaccines against systemic Neisseria meningitidis serogroup B disease. Vaccine. 2007;25(16):3080-4.
Acevedo R, Fernandez S, Zayas C, Acosta A, Sarmiento ME, Ferro VA, et al. Bacterial Outer Membrane Vesicles and Vaccine Applications. Frontiers in immunology. 2014;5:121.
Kesty NC, Kuehn MJ. Incorporation of heterologous outer membrane and periplasmic proteins into *Escherichia coli* outer membrane vesicles. The Journal of biological chemistry. 2004;279(3):2069-76.
Fantappie L, de Santis M, Chiarot E, Carboni F, Bensi G, Jousson O, et al. Antibody-mediated immunity induced by engineered *Escherichia coli* OMVs carrying heterologous antigens in their lumen. Journal of extracellular vesicles. 2014;3.
Schild S, Nelson EJ, Bishop AL, Camilli A. Characterization of Vibrio cholerae outer membrane vesicles as a candidate vaccine for cholera. Infection and immunity. 2009;77(1):472-84.
Poland GA. Vaccines against Lyme disease: What happened and what lessons can we learn? Clinical infectious diseases : an official publication of the Infectious Diseases Society of America. 2011;52 Suppl 3:s253-8.
Barat S, Willer Y, Rizos K, Claudi B, Maze A, Schemmer AK, et al. Immunity to intracellular *Salmonella* depends on surface-associated antigens. PLoS pathogens. 2012;8(10):e1002966.
Daleke-Schermerhorn MH, Felix T, Soprova Z, Ten Hagen-Jongman CM, Vikstrom D, Majlessi L, et al. Decoration of outer membrane vesicles with multiple antigens by using an autotransporter approach. Applied and environmental microbiology. 2014;80(18):5854-65.
Mascioni A, Bentley BE, Camarda R, Dilts DA, Fink P, Gusarova V, et al. Structural Basis for the Immunogenic Properties of the Meningococcal Vaccine Candidate LP2086. The Journal of biological chemistry. 2009;284(13):8738-46.
Hess J, Gentschev I, Miko D, Welzel M, Ladel C, Goebel W, et al. Superior efficacy of secreted over somatic antigen display in recombinant *Salmonella* vaccine induced protection against listeriosis. Proceedings of the National Academy of Sciences of the United States of America. 1996;93(4):1458-63.
Kang HY, Curtiss R, 3rd. Immune responses dependent on antigen location in recombinant attenuated *Salmonella typhimurium* vac-

(56) References Cited

OTHER PUBLICATIONS cines following oral immunization. FEMS immunology and medical microbiology. 2003;37(2-3):99-104.
Cornelis P. Expressing genes in different *Escherichia coli* compartments. Current opinion in biotechnology. 2000;11(5):450-4.
Georgiou G, Stathopoulos C, Daugherty PS, Nayak AR, Iverson BL, Curtiss R, 3rd. Display of heterologous proteins on the surface of microorganisms: from the screening of combinatorial libraries to live recombinant vaccines. Nature biotechnology. 1997;15(1):29-34.
Van Bloois E, Winter RT, Kolmar H, Fraaije MW. Decorating microbes: surface display of proteins on *Escherichia coli*. Trends in biotechnology. 2011;29(2):79-86.
Lee SY, Choi JH, Xu Z. Microbial cell-surface display. Trends in biotechnology. 2003;21(1):45-52.
Samuelson P, Gunneriusson E, Nygren PA, Stahl S. Display of proteins on bacteria. Journal of biotechnology. 2002;96(2):129-54.
Jong W, Daleke-Schermerhorn MH, Vikstrom D, Ten Hagen-Jongman CM, de Punder K, van der Wel NN, et al. An autotransporter display platform for the development of multivalent recombinant bacterial vector vaccines. Microbial cell factories. 2014;13(1):162.
Park M, Sun Q, Liu F, DeLisa MP, Chen W. Positional assembly of enzymes on bacterial outer membrane vesicles for cascade reactions. PloS one. 2014;9(5):e97103.
Schroeder J, Aebischer T. Recombinant outer membrane vesicles to augment antigen-specific live vaccine responses. Vaccine. 2009;27(48):6748-54.
Jong WS, Sauri A, Luirink J. Extracellular production of recombinant proteins using bacterial autotransporters. Current opinion in biotechnology. 2010;21(5):646-52.
Jose J, Meyer TF. The autodisplay story, from discovery to biotechnical and biomedical applications. Microbiology and molecular biology reviews : MMBR. 2007;71(4):600-19.
Jung HC, Lebeault JM, Pan JG. Surface display of Zymomonas mobilis levansucrase by using the ice-nucleation protein of Pseudomonas syringae. Nature biotechnology. 1998;16(6):576-80.
Sigal LH, Zahradnik JM, Lavin P, Patella SJ, Bryant G, Haselby R, et al. A vaccine consisting of recombinant Borrelia burgdorferi outer-surface protein A to prevent Lyme disease. Recombinant Outer-Surface Protein A Lyme Disease Vaccine Study Consortium. The New England journal of medicine. 1998;339(4):216-22.
Steere AC, Sikand VK, Meurice F, Parenti DL, Fikrig E, Schoen RT, et al. Vaccination against Lyme disease with recombinant Borrelia burgdorferi outer-surface lipoprotein A with adjuvant. Lyme Disease Vaccine Study Group. The New England journal of medicine. 1998;339(4):209-15.
Wressnigg N, Barrett PN, Pollabauer EM, O'Rourke M, Portsmouth D, Schwendinger MG, et al. A Novel Multivalent OspA Vaccine against Lyme Borreliosis Is Safe and Immunogenic in an Adult Population Previously Infected with Borrelia burgdorferi Sensu Lato. Clinical and vaccine immunology : CVI. 2014;21(11):1490-9.
Comstedt P, Hanner M, Schuler W, Meinke A, Lundberg U. Design and Development of a Novel Vaccine for Protection against Lyme Borreliosis. PloS one. 2014;9(11):e113294.
Fletcher LD, Bernfield L, Barniak V, Farley JE, Howell A, Knauf M, et al. Vaccine Potential of the Neisseria meningitidis 2086 Lipoprotein. Infection and immunity. 2004;72(4):2088-100.
Masignani V, Comanducci M, Giuliani MM, Bambini S, Adu-Bobie J, Arico B, et al. Vaccination against Neisseria meningitidis using three variants of the lipoprotein GNA1870. The Journal of experimental medicine. 2003;197(6):789-99.
Koeberling O, Seubert A, Granoff DM. Bactericidal antibody responses elicited by a meningococcal outer membrane vesicle vaccine with overexpressed factor H-binding protein and genetically attenuated endotoxin. The Journal of infectious diseases. 2008;198(2):262-70.
Van de Waterbeemd B, Streefland M, van der Ley P, Zomer B, van Dijken H, Martens D, et al. Improved OMV vaccine against Neisseria meningitidis using genetically engineered strains and a detergent-free purification process. Vaccine. 2010;28(30):4810-6.
Brightbill HD, Libraty DH, Krutzik SR, Yang RB, Belisle JT, Bleharski JR, et al. Host defense mechanisms triggered by microbial lipoproteins through toll-like receptors. Science. 1999;285(5428):732-6.
Thoma-Uszynski S, Stenger S, Takeuchi O, Ochoa MT, Engele M, Sieling PA, et al. Induction of direct antimicrobial activity through mammalian toll-like receptors. Science. 2001;291(5508)1544-7.
Steere AC, Livey I. Lyme disease vaccines. Plotkin SA, Orenstein WA, editors. Saunders, PA, USA2013.
Schulze RJ, Zuckert WR. Borrelia burgdorferi lipoproteins are secreted to the outer surface by default. Molecular microbiology. 2006;59(5):1473-84.
Comstedt et al., "Design and development of a novel vaccine for protection against Lyme borreliosis", PLOS One, 2014, vol. 9, No. 11, pp. 1-12.
Daleke-Schermerhorn et al., "Decoration of outer membrane vesicles with multiple antigens by using an autotransporter approach". Applied and Environmental Microbiology, Sep. 2014, vol. 80, No. 18, pp. 5854-5865.
Jong et al., "A structurally informed autotransporter platform for efficient heterologous protein secretion and display". Microbial Cell Factories, 2012, vol. 11, No. 85, pp. 1-11.
Jong et al., "An autotransporter display platform for the development of multivalent recombinant bacterial vector vaccines". Microbial Cell Factories, Nov. 2014, vol. 13, No. 162, pp. 1-14.
Koeberling et al., "Bactericidal antibody responses elicited by a meningococcal outer membrane vesicle vaccine with overexpressed factor H-binding protein and genetically attenuated endotoxin". Journal of Infectious Diseases, Jul. 2008, vol. 198, pp. 262-270.
Mascioni et al., "NMR dynamics and antibody recognition of the meningococcal lapidated outer membrane protein LP2086 in micellar solution", Biochimica et Biophysica Acta, 2010, vol. 1798, pp. 87-93.
Salverda et al., "Surface display of a borrelial lipoprotein on meningococcal outer membrane vesicles". Vaccine, 2016, vol. 34, pp. 1025-1033.
Van De Waterbeemd et al. "Improved OMV vaccine against Neisseria meningitides using genetically engineered strains and a detergent-free purification process". Vaccine, 2010, vol. 28, pp. 4810-4816.
Wressnigg et al., "A novel multivalent OspA vaccine against Lyme Borreliosis is safe and immunogenic in an adult population previously infected with Borrelia burgdorferi Sensu Lato", Clinical and Vaccine Immunology: CVI, Nov. 2014, vol. 21, No. 11, pp. 1490-1499.
Wressnigg et al., "Safety and immunogenicity of a novel multivalent OspA vaccine against Lyme borreliosis in healthy adults: a double-blind, randomized, dose-escalation phase 1/2 trial". The Lancet, Infectious Diseases, Aug. 2013, vol. 13, pp. 680-689.
Giuliana, et al. "A universal vaccine for serogroup B meningococcus." Proceedings of the National Academy of Sciences 103.29 (2006): 10834-10839.
Huang, Chiung-Yi, et al. "Recombinant lipidated HPV E7 induces a Th-1-biased immune response and protective immunity against cervical cancer in a mouse model." PloS one 7.7 (2012): e40970.
Lewenza, Shawn, Dominique Vidal-Ingigliardi, and Anthony P. Pugsley. "Direct visualization of red fluorescent lipoproteins indicates conservation of the membrane sorting rules in the family Enterobacteriaceae." Journal of bacteriology 188.10 (2006): 3516-3524.
Chen, Hsin-Wei, et al. "A novel technology for the production of a heterologous lipoprotein immunogen in high yield has implications for the field of vaccine design." Vaccine 27.9 (2009): 1400-1409.

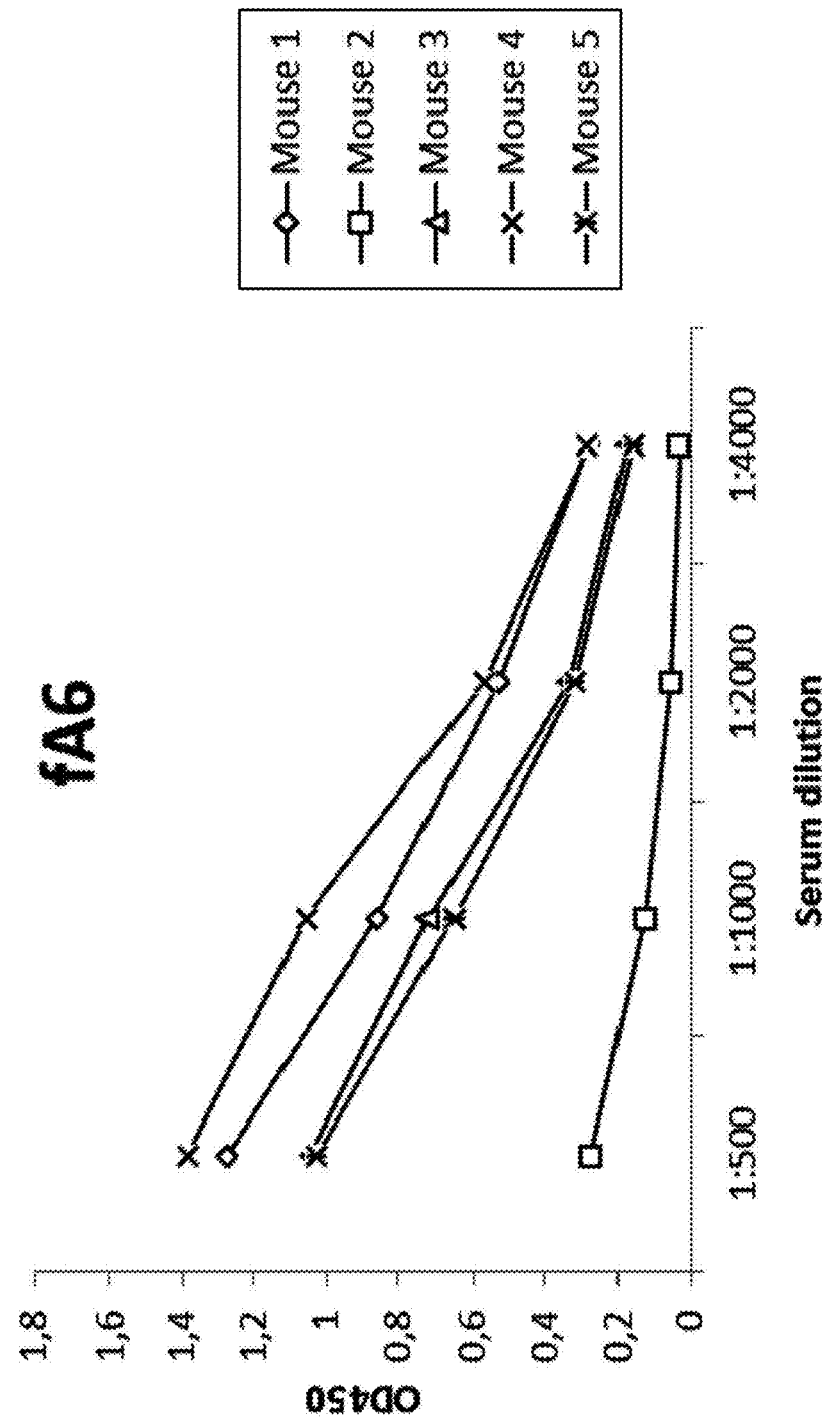

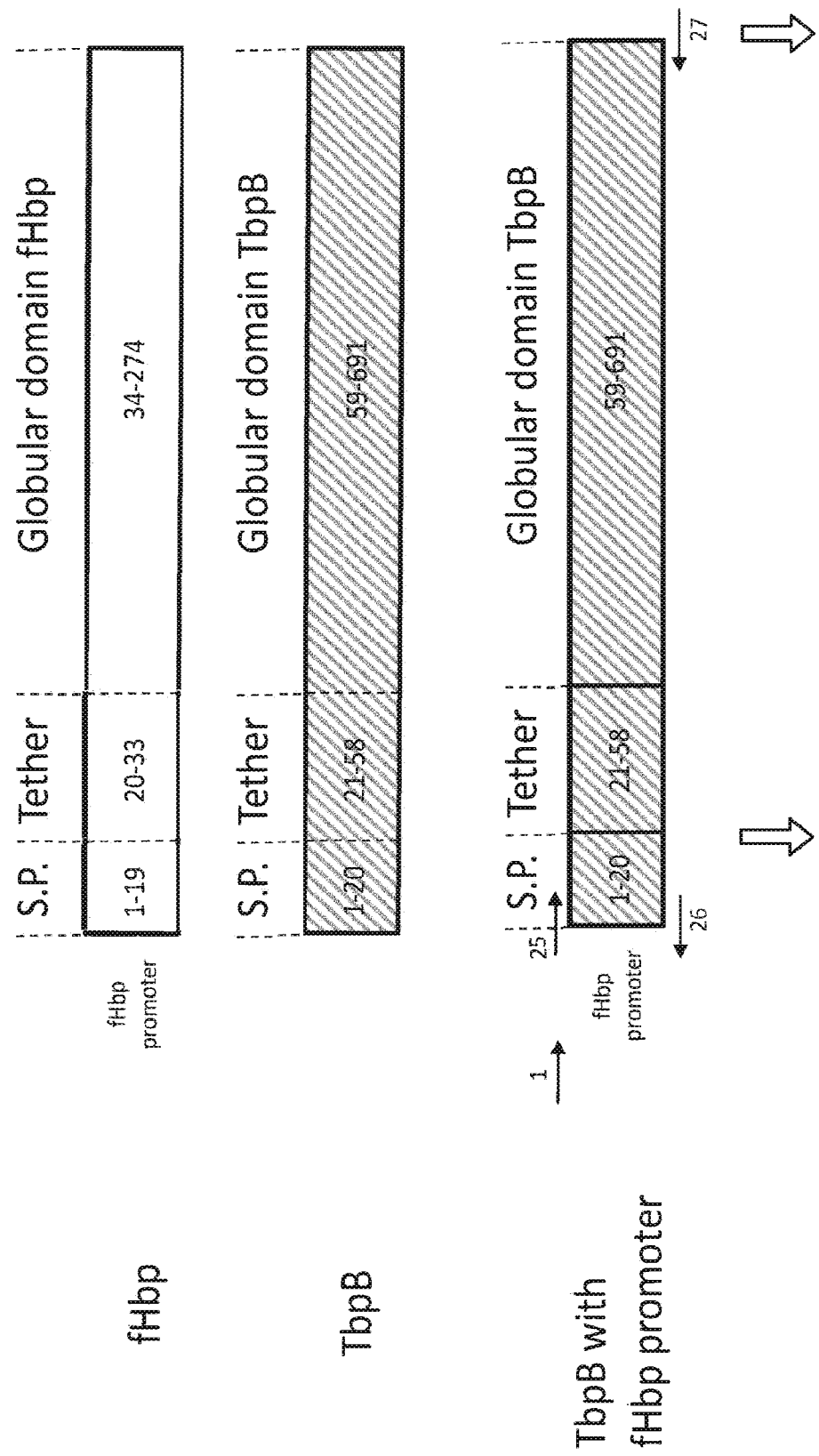

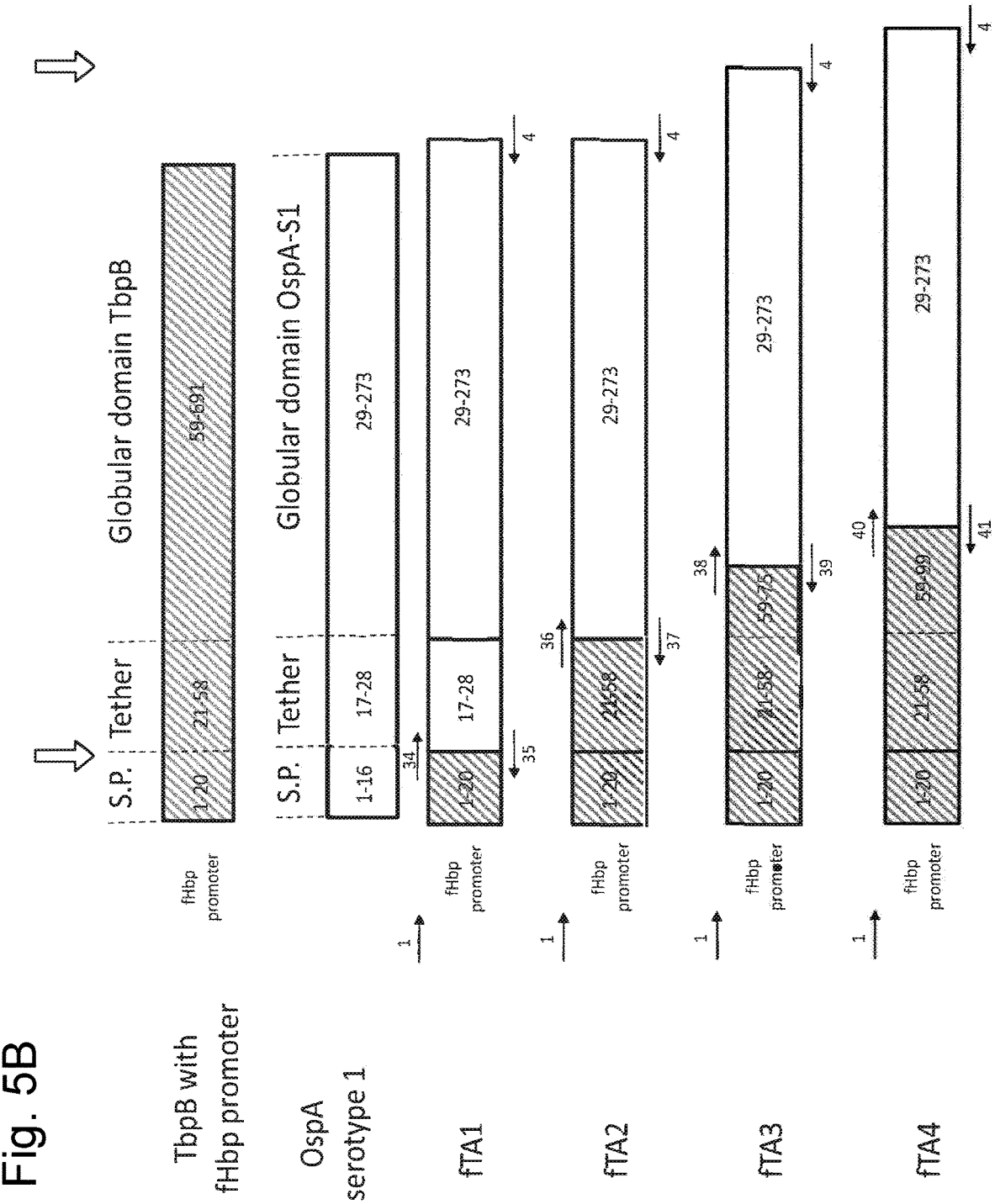

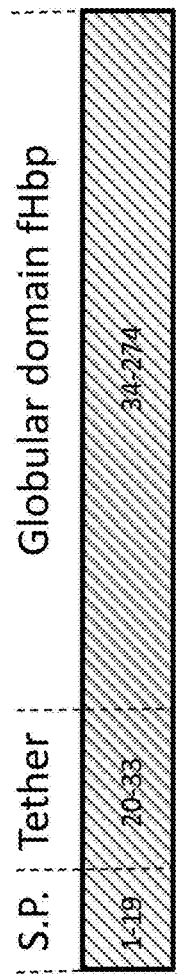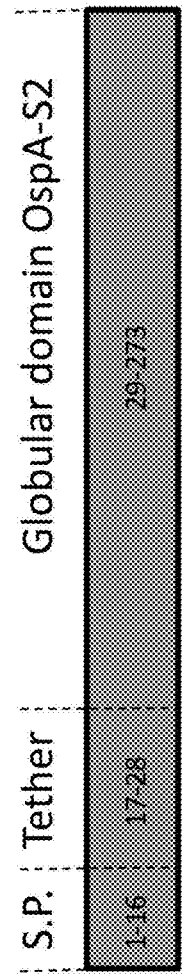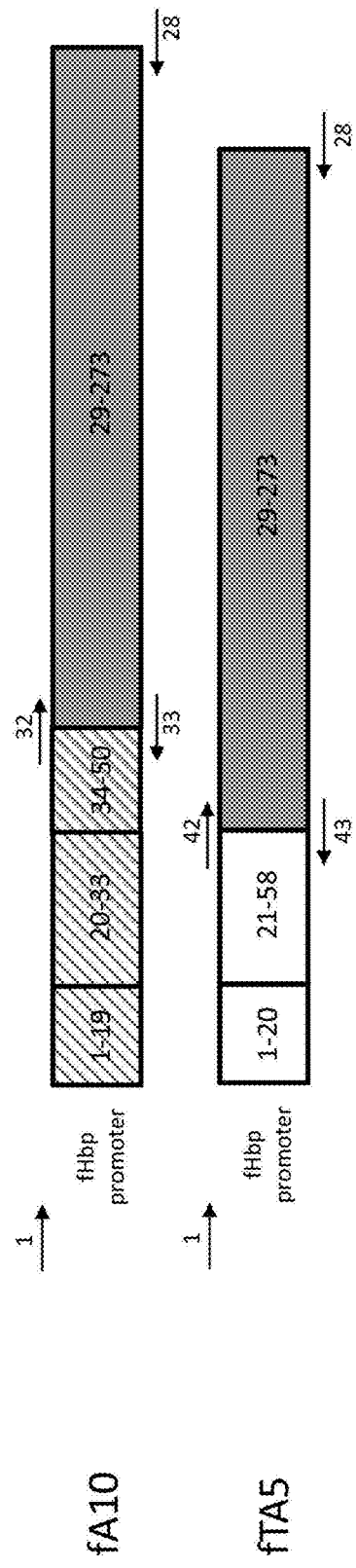
Fig. 7A

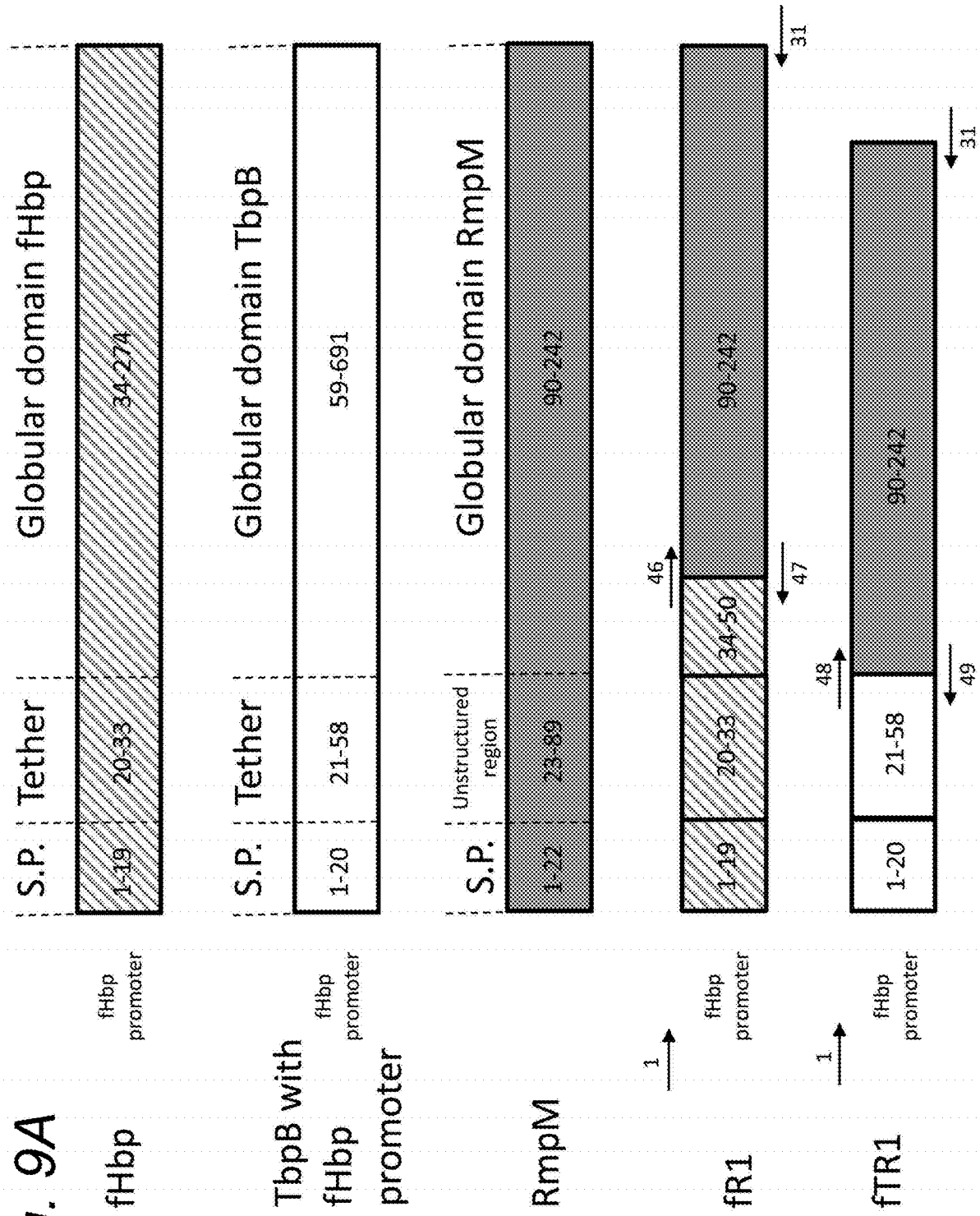

SEQUENCE LISTING

<160> NUMBER OF SEQ ID NOS: 60

<210> SEQ ID NO 1
<211> LENGTH: 274
<212> TYPE: PRT
<213> ORGANISM: Neisseria meningitidis

<400> SEQUENCE: 1

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser

|     |     |     |     |     |     |     |     |     |     |     |     |
| --- | --- | --- | --- | --- | --- | --- | --- | --- | --- | --- | --- |
|     |     | 100 |     |     |     | 105 |     |     |     | 110 |     |

Gly Glu Phe Gln Val Tyr Lys Gln Ser His Ser Ala Leu Thr Ala Phe
            115                  120                  125

Gln Thr Glu Gln Ile Gln Asp Ser Glu His Ser Gly Lys Met Val Ala
130                  135                  140

Lys Arg Gln Phe Arg Ile Gly Asp Ile Ala Gly Glu His Thr Ser Phe
145                  150                  155                  160

Asp Lys Leu Pro Glu Gly Gly Arg Ala Thr Tyr Arg Gly Thr Ala Phe
            165                  170                  175

Gly Ser Asp Asp Ala Gly Gly Lys Leu Thr Tyr Thr Ile Asp Phe Ala
            180                  185                  190

Ala Lys Gln Gly Asn Gly Lys Ile Glu His Leu Lys Ser Pro Glu Leu
            195                  200                  205

Asn Val Asp Leu Ala Ala Ala Asp Ile Lys Pro Asp Gly Lys Arg His
            210                  215                  220

Ala Val Ile Ser Gly Ser Val Leu Tyr Asn Gln Ala Glu Lys Gly Ser
225                  230                  235                  240

Tyr Ser Leu Gly Ile Phe Gly Gly Lys Ala Gln Glu Val Ala Gly Ser
            245                  250                  255

Ala Glu Val Lys Thr Val Asn Gly Ile Arg His Ile Gly Leu Ala Ala
            260                  265                  270

Lys Gln

<210> SEQ ID NO 2
<211> LENGTH: 712
<212> TYPE: PRT
<213> ORGANISM: Neisseria meningitidis

<400> SEQUENCE: 2

Met Asn Asn Pro Leu Val Asn Gln Ala Ala Met Val Leu Pro Val Phe
1                  5                    10                  15

Leu Leu Ser Ala Cys Leu Gly Gly Gly Ser Phe Asp Leu Asp Ser
            20                  25                  30

Val Asp Thr Glu Ala Pro Arg Pro Ala Pro Lys Tyr Gln Asp Val Phe
            35                  40                  45

Ser Glu Lys Pro Gln Ala Gln Lys Asp Gln Gly Gly Tyr Gly Phe Ala
  50                  55                  60

Met Arg Leu Lys Arg Arg Asn Trp Tyr Pro Gln Ala Lys Glu Asp Glu
65                  70                  75                  80

Val Lys Leu Asp Glu Ser Asp Trp Glu Ala Thr Gly Leu Pro Asp Glu
            85                  90                  95

Pro Lys Glu Leu Pro Lys Arg Gln Lys Ser Val Ile Glu Lys Val Glu
            100                  105                  110

Thr Asp Ser Asp Asn Asn Ile Tyr Ser Ser Pro Tyr Leu Lys Pro Ser
            115                  120                  125

Asn His Gln Asn Gly Asn Thr Gly Asn Gly Ile Asn Gln Pro Lys Asn
            130                  135                  140

Gln Ala Lys Asp Tyr Glu Asn Phe Lys Val Tyr Ser Gly Trp Phe
145                  150                  155                  160

Tyr Lys His Ala Lys Arg Glu Phe Asn Leu Lys Val Glu Pro Lys Ser
            165                  170                  175

Ala Lys Asn Gly Asp Asp Gly Tyr Ile Phe Tyr His Gly Lys Glu Pro
            180                  185                  190

Ser Arg Gln Leu Pro Ala Ser Gly Lys Ile Thr Tyr Lys Gly Val Trp

```
            195                 200                 205
His Phe Ala Thr Asp Thr Lys Lys Gly Gln Lys Phe Arg Glu Ile Ile
210                 215                 220

Gln Pro Ser Lys Ser Gln Gly Asp Arg Tyr Ser Gly Phe Ser Gly Asp
225                 230                 235                 240

Asp Gly Glu Glu Tyr Ser Asn Lys Asn Lys Ser Thr Leu Thr Asp Gly
                245                 250                 255

Gln Glu Gly Tyr Gly Phe Thr Ser Asn Leu Glu Val Asp Phe His Asn
            260                 265                 270

Lys Lys Leu Thr Gly Lys Leu Ile Arg Asn Asn Ala Asn Thr Asp Asn
        275                 280                 285

Asn Gln Ala Thr Thr Thr Gln Tyr Tyr Ser Leu Glu Ala Gln Val Thr
290                 295                 300

Gly Asn Arg Phe Asn Gly Lys Ala Thr Ala Thr Asp Lys Pro Gln Gln
305                 310                 315                 320

Asn Ser Glu Thr Lys Glu His Pro Phe Val Ser Asp Ser Ser Ser Leu
                325                 330                 335

Ser Gly Gly Phe Phe Gly Pro Gln Gly Glu Glu Leu Gly Phe Arg Phe
            340                 345                 350

Leu Ser Asp Asp Gln Lys Val Ala Val Val Gly Ser Ala Lys Thr Lys
        355                 360                 365

Asp Lys Pro Ala Asn Gly Asn Thr Ala Ala Ala Ser Gly Gly Thr Asp
370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
                405                 410                 415

Val Gln Lys Leu Asp Asn Phe Ser Asn Ala Ala Gln Leu Val Val Asp
            420                 425                 430

Gly Ile Met Ile Pro Leu Leu Pro Glu Ala Ser Glu Ser Gly Asn Asn
        435                 440                 445

Gln Ala Asn Gln Gly Thr Asn Gly Gly Thr Ala Phe Thr Arg Lys Phe
450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
                485                 490                 495

Lys Thr Lys Thr Tyr Glu Val Glu Val Cys Cys Ser Asn Leu Asn Tyr
            500                 505                 510

Leu Lys Tyr Gly Met Leu Thr Arg Lys Asn Ser Lys Ser Ala Met Gln
        515                 520                 525

Ala Gly Glu Ser Ser Gln Ala Asp Ala Lys Thr Glu Gln Val Glu
530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
610                 615                 620
```

-continued

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
            645                 650                 655

Tyr Ile Thr Asp Ala Lys Val Gln Gly Gly Phe Tyr Gly Pro Lys Ala
        660                 665                 670

Glu Glu Leu Gly Gly Trp Phe Ala Tyr Pro Gly Asp Lys Gln Thr Lys
    675                 680                 685

Asn Ala Thr Asn Ala Ser Gly Asn Ser Ser Ala Thr Val Val Phe Gly
690                 695                 700

Ala Lys Arg Gln Gln Pro Val Arg
705                 710

<210> SEQ ID NO 3
<211> LENGTH: 737
<212> TYPE: PRT
<213> ORGANISM: Neisseria meningitidis

<400> SEQUENCE: 3

Met Cys Lys Pro Asn Tyr Gly Gly Ile Val Leu Leu Pro Leu Leu Leu
1               5                   10                  15

Ala Ser Cys Ile Gly Gly Asn Phe Gly Val Gln Pro Val Val Glu Ser
            20                  25                  30

Thr Pro Thr Ala Tyr Pro Val Thr Phe Lys Ser Lys Asp Val Pro Thr
        35                  40                  45

Pro Pro Pro Ala Gly Ser Ser Val Glu Thr Thr Pro Val Asn Arg Pro
    50                  55                  60

Ala Val Gly Ala Ala Met Arg Leu Pro Arg Arg Asn Ile Ala Ser Tyr
65                  70                  75                  80

Lys Gln Asp Gly Thr Glu Ile Pro Asp Lys His Gln Ala Glu Glu His
                85                  90                  95

Leu Pro Leu Lys Glu Lys Asp Ile Leu Phe Leu Asp Gly Thr Leu Lys
            100                 105                 110

Glu Gln Ala Asp Lys Leu Lys Lys Lys Ile Asn Glu Arg Tyr Ser Asp
        115                 120                 125

Val Arg Val Ile Thr Ser Lys Lys Glu Glu Lys Tyr Gln Tyr Gln
    130                 135                 140

Phe Val Arg Ala Gly Tyr Val Phe Thr Arg Ala Glu Gly Lys Asp Asn
145                 150                 155                 160

Glu Lys Glu Lys Thr Ser Asp Gly Lys Glu Phe Val Asn Arg Phe Ser
                165                 170                 175

Tyr Asp Gly Phe Val Tyr Tyr Ser Gly Glu Arg Pro Ser Gln Ser Leu
            180                 185                 190

Pro Ser Ala Gly Thr Val Gln Tyr Ser Gly Asn Trp Gln Tyr Met Thr
        195                 200                 205

Asp Ala Lys Arg His Arg Thr Gly Lys Ala Val Ser Ser Thr Asp Leu
    210                 215                 220

Gly Tyr Thr Thr Tyr Tyr Gly Asn Glu Ile Gly Ala Thr Ser Tyr Glu
225                 230                 235                 240

Ala Arg Asp Ala Asp Arg Glu Lys His Pro Ala Glu Tyr Thr Val
                245                 250                 255

Asp Phe Asp Asn Lys Thr Leu Asn Gly Lys Leu Ile Lys Asn Gln Tyr
            260                 265                 270

Val Gln Asn Lys Ser Asn Pro Asn Glu Pro Lys Lys Pro Leu Thr Ile

```
            275                 280                 285
Tyr Asp Ile Thr Ala Thr Leu Asp Gly Asn Arg Phe Thr Gly Ser Ala
            290                 295                 300
Lys Val Ser Thr Glu Val Lys Thr Gln His Ala Asp Lys Glu Tyr Leu
305                 310                 315                 320
Phe Phe His Thr Asp Ala Asp Gln Arg Leu Glu Gly Gly Phe Phe Gly
                325                 330                 335
Asp Asn Gly Glu Glu Leu Ala Gly Arg Phe Ile Ser Asn Asp Asn Ser
            340                 345                 350
Val Phe Gly Val Phe Ala Gly Lys Gln Lys Thr Glu Thr Glu Asn Ala
            355                 360                 365
Ala Asp Thr Lys Pro Ala Leu Ser Ser Gly Lys His Thr Lys Ile Leu
            370                 375                 380
Asp Ser Leu Lys Ile Ser Val Asp Glu Ala Ser Asp Lys Asn Pro Arg
385                 390                 395                 400
Glu Phe Ala Ile Ser Ser Met Pro Asp Phe Gly His Pro Asp Lys Leu
                405                 410                 415
Leu Val Glu Gly Arg Glu Ile Pro Leu Val Asn Lys Glu Gln Thr Ile
            420                 425                 430
Glu Leu Ala Asp Gly Arg Lys Thr Thr Ile Arg Thr Cys Cys Asp Phe
            435                 440                 445
Leu Thr Tyr Val Lys Ile Gly Arg Met Gln Thr Glu Arg Pro Ala Ala
            450                 455                 460
Lys Pro Lys Ala Gln Asp Glu Arg Asp Glu Asp Thr Gly Val
465                 470                 475                 480
Asp Ser Val Glu Glu Gly Glu Asp Glu Ile Asp Asp Glu Glu Gly Thr
                485                 490                 495
Glu Asp Ala Ala Val Lys Asp Glu Gly Ser Glu Glu Asp Glu Ala Val
            500                 505                 510
Glu Gly Glu Asp Glu Ala Glu Glu Pro Glu Glu Glu Ser Pro Thr Glu
            515                 520                 525
Glu Gly Gly Ser Gly Ser Asp Gly Ile Leu Pro Ala Pro Glu Ala Pro
            530                 535                 540
Lys Gly Arg Asn Ile Asp Leu Phe Leu Lys Gly Ile Arg Thr Ala Glu
545                 550                 555                 560
Thr Asp Ile Pro Lys Thr Gly Glu Ala His Tyr Thr Gly Thr Trp Glu
                565                 570                 575
Ala Arg Ile Gly Lys Pro Ile Gln Trp Asp Asn Gln Ala Asp Lys Glu
            580                 585                 590
Ala Ala Lys Ala Val Phe Thr Val Asp Phe Gly Lys Lys Ser Ile Ser
            595                 600                 605
Gly Thr Leu Thr Glu Glu Asn Gly Val Glu Pro Ala Phe His Ile Glu
            610                 615                 620
Asn Gly Lys Ile Glu Gly Asn Gly Phe Tyr Ala Thr Ala Arg Thr Arg
625                 630                 635                 640
Glu Asn Gly Ile Asn Leu Ser Gly Asn Gly Ser Thr Asp Pro Lys Thr
                645                 650                 655
Phe Gln Ala Ser Asn Leu Arg Val Glu Gly Gly Phe Tyr Gly Pro Gln
            660                 665                 670
Ala Glu Glu Leu Gly Gly Ile Ile Phe Asn Asn Asp Gly Lys Ser Leu
            675                 680                 685
Gly Ile Thr Glu Gly Thr Glu Asn Lys Val Asp Val Glu Ala Glu Val
            690                 695                 700
```

Asp Ala Glu Val Asp Val Gly Lys Gln Leu Glu Ser Glu Val Lys His
705                 710                 715                 720

Gln Phe Gly Val Val Phe Gly Ala Lys Lys Asp Met Gln Glu Val Glu
            725                 730                 735

Lys

<210> SEQ ID NO 4
<211> LENGTH: 273
<212> TYPE: PRT
<213> ORGANISM: Artificial
<220> FEATURE:
<223> OTHER INFORMATION: Borrelia burgdorferi OspA lipoprotein with the
      PCR induced mutation K233I

<400> SEQUENCE: 4

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Ile Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 5
<211> LENGTH: 6
<212> TYPE: PRT
<213> ORGANISM: Artificial
<220> FEATURE:

<223> OTHER INFORMATION: Linker between N- and C-terminal fusion
partners

<400> SEQUENCE: 5

```
Pro Gly Gly Ser Gly Ala
1               5
```

<210> SEQ ID NO 6
<211> LENGTH: 299
<212> TYPE: PRT
<213> ORGANISM: Neisseria meningitidis

<400> SEQUENCE: 6

```
Met Pro Ser Glu Lys Lys Met Cys Ile Glu Met Lys Phe Ile Phe Phe
1               5                   10                  15

Val Leu Tyr Val Leu Gln Phe Leu Pro Phe Ala Leu Leu His Lys Ile
            20                  25                  30

Ala Asp Leu Thr Gly Leu Leu Ala Tyr Leu Leu Val Lys Pro Arg Arg
        35                  40                  45

Arg Ile Gly Glu Ile Asn Leu Ala Lys Cys Phe Ser Glu Trp Ser Glu
    50                  55                  60

Glu Lys Arg Lys Thr Val Leu Lys Gln His Phe Lys His Met Ala Lys
65                  70                  75                  80

Leu Met Leu Glu Tyr Gly Leu Tyr Trp Tyr Ala Pro Ala Gly Arg Leu
                85                  90                  95

Lys Ser Leu Val Arg Tyr Arg Asn Lys His Tyr Leu Asp Asp Ala Leu
            100                 105                 110

Ala Ala Gly Glu Lys Val Ile Ile Leu Tyr Pro His Phe Thr Ala Phe
        115                 120                 125

Glu Met Ala Val Tyr Ala Leu Asn Gln Asp Ile Pro Leu Ile Ser Met
    130                 135                 140

Tyr Ser His Gln Lys Asn Lys Ile Leu Asp Glu Gln Ile Leu Lys Gly
145                 150                 155                 160

Arg Asn Arg Tyr His Asn Val Phe Leu Ile Gly Arg Thr Glu Gly Leu
                165                 170                 175

Arg Ala Leu Val Lys Gln Phe Arg Lys Ser Ser Ala Pro Phe Leu Tyr
            180                 185                 190

Leu Pro Asp Gln Asp Phe Gly Arg Asn Asp Ser Val Phe Val Asp Phe
        195                 200                 205

Phe Gly Ile Gln Thr Ala Thr Ile Thr Gly Leu Ser Arg Ile Ala Ala
    210                 215                 220

Leu Ala Asn Ala Lys Val Ile Pro Ala Ile Pro Val Arg Glu Ala Asp
225                 230                 235                 240

Asn Thr Val Thr Leu His Phe Tyr Pro Ala Trp Lys Ser Phe Pro Gly
                245                 250                 255

Glu Asp Ala Lys Ala Asp Ala Gln Arg Met Asn Arg Phe Ile Glu Asp
            260                 265                 270

Arg Val Arg Glu His Pro Glu Gln Tyr Phe Trp Leu His Lys Arg Phe
        275                 280                 285

Lys Thr Arg Pro Glu Gly Ser Pro Asp Phe Tyr
    290                 295
```

<210> SEQ ID NO 7
<211> LENGTH: 242
<212> TYPE: PRT
<213> ORGANISM: Neisseria meningitidis

<400> SEQUENCE: 7

Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val
            20                  25                  30

Ser Gly Gln Ser Asn Glu Ile Val Arg Asn Asn Tyr Gly Glu Cys Trp
        35                  40                  45

Lys Asn Ala Tyr Phe Asp Lys Ala Ser Gln Gly Arg Val Glu Cys Gly
    50                  55                  60

Asp Ala Val Ala Ala Pro Glu Pro Glu Pro Glu Pro Glu Pro Ala Pro
65                  70                  75                  80

Ala Pro Val Val Val Val Glu Gln Ala Pro Gln Tyr Val Asp Glu Thr
                85                  90                  95

Ile Ser Leu Ser Ala Lys Thr Leu Phe Gly Phe Asp Lys Asp Ser Leu
            100                 105                 110

Arg Ala Glu Ala Gln Asp Asn Leu Lys Val Leu Ala Gln Arg Leu Ser
        115                 120                 125

Arg Thr Asn Val Gln Ser Val Arg Val Glu Gly His Thr Asp Phe Met
    130                 135                 140

Gly Ser Asp Lys Tyr Asn Gln Ala Leu Ser Glu Arg Arg Ala Tyr Val
145                 150                 155                 160

Val Ala Asn Asn Leu Val Ser Asn Gly Val Pro Val Ser Arg Ile Ser
                165                 170                 175

Ala Val Gly Leu Gly Glu Ser Gln Ala Gln Met Thr Gln Val Cys Glu
            180                 185                 190

Ala Glu Val Ala Lys Leu Gly Ala Lys Val Ser Lys Ala Lys Lys Arg
        195                 200                 205

Glu Ala Leu Ile Ala Cys Ile Glu Pro Asp Arg Arg Val Asp Val Lys
    210                 215                 220

Ile Arg Ser Ile Val Thr Arg Gln Val Val Pro Ala His Asn His His
225                 230                 235                 240

Gln His

<210> SEQ ID NO 8
<211> LENGTH: 1083
<212> TYPE: PRT
<213> ORGANISM: Neisseria meningitidis

<400> SEQUENCE: 8

Met Arg Thr Thr Pro Thr Phe Pro Thr Lys Thr Phe Lys Pro Thr Ala
1               5                   10                  15

Met Ala Leu Ala Val Ala Thr Thr Leu Ser Ala Cys Leu Gly Gly Gly
            20                  25                  30

Gly Gly Gly Thr Ser Ala Pro Asp Phe Asn Ala Gly Thr Gly Ile
        35                  40                  45

Gly Ser Asn Ser Arg Ala Thr Thr Ala Lys Ser Ala Val Ser Tyr
    50                  55                  60

Ala Gly Ile Lys Asn Glu Met Cys Lys Asp Arg Ser Met Leu Cys Ala
65                  70                  75                  80

Gly Arg Asp Asp Val Ala Val Thr Asp Arg Asp Ala Lys Ile Asn Ala
                85                  90                  95

Pro Pro Pro Pro Asn Leu His Thr Gly Asp Phe Pro Asn Pro Asn Asp
            100                 105                 110

Ala Tyr Lys Asn Leu Ile Asn Leu Lys Pro Ala Ile Glu Ala Gly Tyr

-continued

```
            115                 120                 125
Thr Gly Arg Gly Val Glu Val Gly Ile Val Asp Thr Gly Glu Ser Val
130                 135                 140
Gly Ser Ile Ser Phe Pro Glu Leu Tyr Gly Arg Lys Glu His Gly Tyr
145                 150                 155                 160
Asn Glu Asn Tyr Lys Asn Tyr Thr Ala Tyr Met Arg Lys Glu Ala Pro
                165                 170                 175
Glu Asp Gly Gly Lys Asp Ile Glu Ala Ser Phe Asp Asp Glu Ala
            180                 185                 190
Val Ile Glu Thr Glu Ala Lys Pro Thr Asp Ile Arg His Val Lys Glu
            195                 200                 205
Ile Gly His Ile Asp Leu Val Ser His Ile Ile Gly Gly Arg Ser Val
210                 215                 220
Asp Gly Arg Pro Ala Gly Gly Ile Ala Pro Asp Ala Thr Leu His Ile
225                 230                 235                 240
Met Asn Thr Asn Asp Gly Thr Lys Asn Glu Met Met Val Ala Ala Ile
                245                 250                 255
Arg Asn Ala Trp Val Lys Leu Gly Glu Arg Gly Val Arg Ile Val Asn
            260                 265                 270
Asn Ser Phe Gly Thr Thr Ser Arg Ala Gly Thr Ala Asp Leu Phe Gln
            275                 280                 285
Ile Ala Asn Ser Glu Glu Gln Tyr Arg Gln Ala Leu Leu Asp Tyr Ser
290                 295                 300
Gly Gly Asp Lys Thr Asp Glu Gly Ile Arg Leu Met Gln Gln Ser Asp
305                 310                 315                 320
Tyr Gly Asn Leu Ser Tyr His Ile Arg Asn Lys Asn Met Leu Phe Ile
                325                 330                 335
Phe Ser Thr Gly Asn Asp Ala Gln Ala Gln Pro Asn Thr Tyr Ala Leu
            340                 345                 350
Leu Pro Phe Tyr Glu Lys Asp Ala Gln Lys Gly Ile Ile Thr Val Ala
            355                 360                 365
Gly Val Asp Arg Ser Gly Glu Lys Phe Lys Arg Glu Met Tyr Gly Glu
370                 375                 380
Pro Gly Thr Glu Pro Leu Glu Tyr Gly Ser Asn His Cys Gly Ile Thr
385                 390                 395                 400
Ala Met Trp Cys Leu Ser Ala Pro Tyr Glu Ala Ser Val Arg Phe Thr
                405                 410                 415
Arg Thr Asn Pro Ile Gln Ile Ala Gly Thr Ser Phe Ser Ala Pro Ile
            420                 425                 430
Val Thr Gly Thr Ala Ala Leu Leu Leu Gln Lys Tyr Pro Trp Met Ser
            435                 440                 445
Asn Asp Asn Leu Arg Thr Thr Leu Leu Thr Thr Ala Gln Asp Ile Gly
450                 455                 460
Ala Val Gly Val Asp Ser Lys Phe Gly Trp Gly Leu Leu Asp Ala Gly
465                 470                 475                 480
Lys Ala Met Asn Gly Pro Ala Ser Phe Pro Phe Gly Asp Phe Thr Ala
                485                 490                 495
Asp Thr Lys Gly Thr Ser Asp Ile Ala Tyr Ser Phe Arg Asn Asp Ile
            500                 505                 510
Ser Gly Thr Gly Gly Leu Ile Lys Lys Gly Gly Ser Gln Leu Gln Leu
            515                 520                 525
His Gly Asn Asn Thr Tyr Thr Gly Lys Thr Ile Ile Glu Gly Gly Ser
530                 535                 540
```

```
Leu Val Leu Tyr Gly Asn Asn Lys Ser Asp Met Arg Val Glu Thr Lys
545                 550                 555                 560

Gly Ala Leu Ile Tyr Asn Gly Ala Ala Ser Gly Gly Ser Leu Asn Ser
                565                 570                 575

Asp Gly Ile Val Tyr Leu Ala Asp Thr Asp Gln Ser Gly Ala Asn Glu
            580                 585                 590

Thr Val His Ile Lys Gly Ser Leu Gln Leu Asp Gly Lys Gly Thr Leu
        595                 600                 605

Tyr Thr Arg Leu Gly Lys Leu Leu Lys Val Asp Gly Thr Ala Ile Ile
    610                 615                 620

Gly Gly Lys Leu Tyr Met Ser Ala Arg Gly Lys Gly Ala Gly Tyr Leu
625                 630                 635                 640

Asn Ser Thr Gly Arg Arg Val Pro Phe Leu Ser Ala Ala Lys Ile Gly
                645                 650                 655

Gln Asp Tyr Ser Phe Phe Thr Asn Ile Glu Thr Asp Gly Gly Leu Leu
            660                 665                 670

Ala Ser Leu Asp Ser Val Glu Lys Thr Ala Gly Ser Glu Gly Asp Thr
        675                 680                 685

Leu Ser Tyr Tyr Val Arg Arg Gly Asn Ala Ala Arg Thr Ala Ser Ala
    690                 695                 700

Ala Ala His Ser Ala Pro Ala Gly Leu Lys His Ala Val Glu Gln Gly
705                 710                 715                 720

Gly Ser Asn Leu Glu Asn Leu Met Val Glu Leu Asp Ala Ser Glu Ser
                725                 730                 735

Ser Ala Thr Pro Glu Thr Val Glu Thr Ala Ala Ala Asp Arg Thr Asp
            740                 745                 750

Met Pro Gly Ile Arg Pro Tyr Gly Ala Thr Phe Arg Ala Ala Ala Ala
        755                 760                 765

Val Gln His Ala Asn Ala Ala Asp Gly Val Arg Ile Phe Asn Ser Leu
    770                 775                 780

Ala Ala Thr Val Tyr Ala Asp Ser Thr Ala Ala His Ala Asp Met Gln
785                 790                 795                 800

Gly Arg Arg Leu Lys Ala Val Ser Asp Gly Leu Asp His Asn Gly Thr
                805                 810                 815

Gly Leu Arg Val Ile Ala Gln Thr Gln Gln Asp Gly Gly Thr Trp Glu
            820                 825                 830

Gln Gly Gly Val Glu Gly Lys Met Arg Gly Ser Thr Gln Thr Val Gly
        835                 840                 845

Ile Ala Ala Lys Thr Gly Glu Asn Thr Thr Ala Ala Thr Leu Gly
    850                 855                 860

Met Gly Arg Ser Thr Trp Ser Glu Asn Ser Ala Asn Ala Lys Thr Asp
865                 870                 875                 880

Ser Ile Ser Leu Phe Ala Gly Ile Arg His Asp Ala Gly Asp Ile Gly
                885                 890                 895

Tyr Leu Lys Gly Leu Phe Ser Tyr Gly Arg Tyr Lys Asn Ser Ile Ser
            900                 905                 910

Arg Ser Thr Gly Ala Asp Glu His Ala Glu Gly Ser Val Asn Gly Thr
        915                 920                 925

Leu Met Gln Leu Gly Ala Leu Gly Gly Val Asn Val Pro Phe Ala Ala
    930                 935                 940

Thr Gly Asp Leu Thr Val Glu Gly Gly Leu Arg Tyr Asp Leu Leu Lys
945                 950                 955                 960
```

-continued

```
Gln Asp Ala Phe Ala Glu Lys Gly Ser Ala Leu Gly Trp Ser Gly Asn
                965                 970                 975
Ser Leu Thr Glu Gly Thr Leu Val Gly Leu Ala Gly Leu Lys Leu Ser
            980                 985                 990
Gln Pro Leu Ser Asp Lys Ala Val Leu Phe Ala Thr Ala Gly Val Glu
        995                 1000                1005
Arg Asp Leu Asn Gly Arg Asp Tyr Thr Val Thr Gly Gly Phe Thr
    1010                1015                1020
Gly Ala Thr Ala Ala Thr Gly Lys Thr Gly Ala Arg Asn Met Pro
    1025                1030                1035
His Thr Arg Leu Val Ala Gly Leu Gly Ala Asp Val Glu Phe Gly
    1040                1045                1050
Asn Gly Trp Asn Gly Leu Ala Arg Tyr Ser Tyr Ala Gly Ser Lys
    1055                1060                1065
Gln Tyr Gly Asn His Ser Gly Arg Val Gly Val Gly Tyr Arg Phe
    1070                1075                1080
```

<210> SEQ ID NO 9
<211> LENGTH: 34
<212> TYPE: DNA
<213> ORGANISM: Artificial
<220> FEATURE:
<223> OTHER INFORMATION: fHbp-F primer

<400> SEQUENCE: 9
catatgcgcc gttcggacga catttgattt ttgc         34

<210> SEQ ID NO 10
<211> LENGTH: 26
<212> TYPE: DNA
<213> ORGANISM: Artificial
<220> FEATURE:
<223> OTHER INFORMATION: fHbp-R primer

<400> SEQUENCE: 10
gacgtcacgg taaattatcg tgttcg                  26

<210> SEQ ID NO 11
<211> LENGTH: 39
<212> TYPE: DNA
<213> ORGANISM: Artificial
<220> FEATURE:
<223> OTHER INFORMATION: OspA-F primer

<400> SEQUENCE: 11
catatgaagg agaatatatt atgaaaaaat atttattgg    39

<210> SEQ ID NO 12
<211> LENGTH: 30
<212> TYPE: DNA
<213> ORGANISM: Artificial
<220> FEATURE:
<223> OTHER INFORMATION: OspA-R primer

<400> SEQUENCE: 12
gacgtctaaa gctaacgcta aagcaaatcc              30

<210> SEQ ID NO 13
<211> LENGTH: 16
<212> TYPE: DNA
<213> ORGANISM: Artificial
<220> FEATURE:
<223> OTHER INFORMATION: M13-F primer

<400> SEQUENCE: 13
gtaaaacgac ggccag                                                          16

<210> SEQ ID NO 14
<211> LENGTH: 17
<212> TYPE: DNA
<213> ORGANISM: Artificial
<220> FEATURE:
<223> OTHER INFORMATION: M13-R primer

<400> SEQUENCE: 14
caggaaacag ctatgac                                                         17

<210> SEQ ID NO 15
<211> LENGTH: 22
<212> TYPE: DNA
<213> ORGANISM: Artificial
<220> FEATURE:
<223> OTHER INFORMATION: pEN11-F primer

<400> SEQUENCE: 15
aaaccgcatt ccgcaccaca ag                                                   22

<210> SEQ ID NO 16
<211> LENGTH: 24
<212> TYPE: DNA
<213> ORGANISM: Artificial
<220> FEATURE:
<223> OTHER INFORMATION: pEN11-R primer

<400> SEQUENCE: 16
gggcgacacg gaaatgttga atac                                                 24

<210> SEQ ID NO 17
<211> LENGTH: 42
<212> TYPE: DNA
<213> ORGANISM: Artificial
<220> FEATURE:
<223> OTHER INFORMATION: fA1-F primer

<400> SEQUENCE: 17
gtgtcgccgc cgacatcggt gcgagcgttt cagtagattt gc                             42

<210> SEQ ID NO 18
<211> LENGTH: 42
<212> TYPE: DNA
<213> ORGANISM: Artificial
<220> FEATURE:
<223> OTHER INFORMATION: fA1-R primer

<400> SEQUENCE: 18
gcaaatctac tgaaacgctc gcaccgatgt cggcggcgac ac                             42

<210> SEQ ID NO 19
<211> LENGTH: 43
<212> TYPE: DNA
<213> ORGANISM: Artificial
<220> FEATURE:
<223> OTHER INFORMATION: fA2b-F primer

<400> SEQUENCE: 19
ggcgacccgg gtggctcagg tgctagcgtt tcagtagatt tgc                            43

<210> SEQ ID NO 20

<211> LENGTH: 43
<212> TYPE: DNA
<213> ORGANISM: Artificial
<220> FEATURE:
<223> OTHER INFORMATION: fA2b-R primer

<400> SEQUENCE: 20
aaacgctagc acctgagcca cccgggtcgc cgattctgaa ctg                          43

<210> SEQ ID NO 21
<211> LENGTH: 45
<212> TYPE: DNA
<213> ORGANISM: Artificial
<220> FEATURE:
<223> OTHER INFORMATION: fA3b-F primer

<400> SEQUENCE: 21
ttaaaaccgg gtggctcagg tgctagggcg acatatcgcg ggacg                        45

<210> SEQ ID NO 22
<211> LENGTH: 45
<212> TYPE: DNA
<213> ORGANISM: Artificial
<220> FEATURE:
<223> OTHER INFORMATION: fA3b-R primer

<400> SEQUENCE: 22
cgccctagca cctgagccac ccggttttaa agcgttttta atttc                        45

<210> SEQ ID NO 23
<211> LENGTH: 43
<212> TYPE: DNA
<213> ORGANISM: Artificial
<220> FEATURE:
<223> OTHER INFORMATION: fA4b-F primer

<400> SEQUENCE: 23
aagcaaccgg gtggctcagg tgctagcgtt tcagtagatt tgc                          43

<210> SEQ ID NO 24
<211> LENGTH: 40
<212> TYPE: DNA
<213> ORGANISM: Artificial
<220> FEATURE:
<223> OTHER INFORMATION: fA4b-R primer

<400> SEQUENCE: 24
aaacgctagc acctgagcca cccggttgct tggcggcaag                              40

<210> SEQ ID NO 25
<211> LENGTH: 34
<212> TYPE: DNA
<213> ORGANISM: Artificial
<220> FEATURE:
<223> OTHER INFORMATION: fA4c-F primer

<400> SEQUENCE: 25
ccttgccgcc aagcaatgta agcaaaatgt tagc                                    34

<210> SEQ ID NO 26
<211> LENGTH: 34
<212> TYPE: DNA
<213> ORGANISM: Artificial
<220> FEATURE:
<223> OTHER INFORMATION: fA4c-R primer

<400> SEQUENCE: 26

-continued gctaacattt tgcttacatt gcttggcggc aagg                          34

<210> SEQ ID NO 27
<211> LENGTH: 43
<212> TYPE: DNA
<213> ORGANISM: Artificial
<220> FEATURE:
<223> OTHER INFORMATION: fA5c-F primer

<400> SEQUENCE: 27
gaaattaaaa acgctttaaa atgcagcagc ggagggggtg gtg               43

<210> SEQ ID NO 28
<211> LENGTH: 43
<212> TYPE: DNA
<213> ORGANISM: Artificial
<220> FEATURE:
<223> OTHER INFORMATION: fA5c-R primer

<400> SEQUENCE: 28
caccaccccc tccgctgctg cattttaaag cgttttttaat ttc              43

<210> SEQ ID NO 29
<211> LENGTH: 38
<212> TYPE: DNA
<213> ORGANISM: Artificial
<220> FEATURE:
<223> OTHER INFORMATION: fA6-F primer

<400> SEQUENCE: 29
ccataaagac aaaggtttga gcgtttcagt agatttgc                     38

<210> SEQ ID NO 30
<211> LENGTH: 38
<212> TYPE: DNA
<213> ORGANISM: Artificial
<220> FEATURE:
<223> OTHER INFORMATION: fA6-R primer

<400> SEQUENCE: 30
gcaaatctac tgaaacgctc aaacctttgt ctttatgg                     38

<210> SEQ ID NO 31
<211> LENGTH: 38
<212> TYPE: DNA
<213> ORGANISM: Artificial
<220> FEATURE:
<223> OTHER INFORMATION: fA7-F primer

<400> SEQUENCE: 31
caatacgggc aaattgaaga gcgtttcagt agatttgc                     38

<210> SEQ ID NO 32
<211> LENGTH: 38
<212> TYPE: DNA
<213> ORGANISM: Artificial
<220> FEATURE:
<223> OTHER INFORMATION: fA7-R primer

<400> SEQUENCE: 32
gcaaatctac tgaaacgctc ttcaatttgc ccgtattg                     38

<210> SEQ ID NO 33
<211> LENGTH: 46
<212> TYPE: DNA

<213> ORGANISM: artificial
<220> FEATURE:
<223> OTHER INFORMATION: pfHbpTbpB-F primer

<400> SEQUENCE: 33
cgtatgacta ggagtaaacc tatgaacaat ccattggtga atcagg         46

<210> SEQ ID NO 34
<211> LENGTH: 37
<212> TYPE: DNA
<213> ORGANISM: artificial
<220> FEATURE:
<223> OTHER INFORMATION: pfHbpTbpB-R primer

<400> SEQUENCE: 34
ccaatggatt gttcataggt ttactcctag tcatacg                   37

<210> SEQ ID NO 35
<211> LENGTH: 26
<212> TYPE: DNA
<213> ORGANISM: artificial
<220> FEATURE:
<223> OTHER INFORMATION: TbpB-R primer

<400> SEQUENCE: 35
gacgtccgtc tgaagcctta ttctcg                               26

<210> SEQ ID NO 36
<211> LENGTH: 25
<212> TYPE: DNA
<213> ORGANISM: artificial
<220> FEATURE:
<223> OTHER INFORMATION: OspA afz-R long primer

<400> SEQUENCE: 36
gacgtctact ttttggctca gtacc                                25

<210> SEQ ID NO 37
<211> LENGTH: 31
<212> TYPE: DNA
<213> ORGANISM: artificial
<220> FEATURE:
<223> OTHER INFORMATION: OspC-F primer

<400> SEQUENCE: 37
catatgaata aaaaggaggc acaaattaat g                         31

<210> SEQ ID NO 38
<211> LENGTH: 33
<212> TYPE: DNA
<213> ORGANISM: artificial
<220> FEATURE:
<223> OTHER INFORMATION: OspC-R primer

<400> SEQUENCE: 38
gacgtcttaa ttaaggtttt tttggactttt ctg                      33

<210> SEQ ID NO 39
<211> LENGTH: 24
<212> TYPE: DNA
<213> ORGANISM: artificial
<220> FEATURE:
<223> OTHER INFORMATION: RmpM-R primer

<400> SEQUENCE: 39
gacgtcgcat cggcaagata ttgc                                 24

<210> SEQ ID NO 40
<211> LENGTH: 38
<212> TYPE: DNA
<213> ORGANISM: artificial
<220> FEATURE:
<223> OTHER INFORMATION: fA10-F primer

<400> SEQUENCE: 40
ccataaagac aaaggtttga gcgcttcagt agatttgc                           38

<210> SEQ ID NO 41
<211> LENGTH: 38
<212> TYPE: DNA
<213> ORGANISM: artificial
<220> FEATURE:
<223> OTHER INFORMATION: fA10-R primer

<400> SEQUENCE: 41
gcaaatctac tgaagcgctc aaacctttgt ctttatgg                           38

<210> SEQ ID NO 42
<211> LENGTH: 46
<212> TYPE: DNA
<213> ORGANISM: artificial
<220> FEATURE:
<223> OTHER INFORMATION: fTA1-F primer

<400> SEQUENCE: 42
cctgtgtttt tgttgagtgc ttgtaagcaa aatgttagca gccttg                  46

<210> SEQ ID NO 43
<211> LENGTH: 46
<212> TYPE: DNA
<213> ORGANISM: artificial
<220> FEATURE:
<223> OTHER INFORMATION: fTA1-R primer

<400> SEQUENCE: 43
caaggctgct aacattttgc ttacaagcac tcaacaaaaa cacagg                  46

<210> SEQ ID NO 44
<211> LENGTH: 38
<212> TYPE: DNA
<213> ORGANISM: artificial
<220> FEATURE:
<223> OTHER INFORMATION: fTA2-F primer

<400> SEQUENCE: 44
gcaagcccaa aaagaccaaa gcgtttcagt agatttgc                           38

<210> SEQ ID NO 45
<211> LENGTH: 38
<212> TYPE: DNA
<213> ORGANISM: artificial
<220> FEATURE:
<223> OTHER INFORMATION: fTA2-R primer

<400> SEQUENCE: 45
gcaaatctac tgaaacgctt tggtcttttt gggcttgc                           38

<210> SEQ ID NO 46
<211> LENGTH: 44
<212> TYPE: DNA
<213> ORGANISM: artificial
<220> FEATURE:

<223> OTHER INFORMATION: fTA3-F primer

<400> SEQUENCE: 46
caagcggcgg aattggtatc agaggagcgt tcagtagat ttgc        44

<210> SEQ ID NO 47
<211> LENGTH: 44
<212> TYPE: DNA
<213> ORGANISM: artificial
<220> FEATURE:
<223> OTHER INFORMATION: fTA3-R primer

<400> SEQUENCE: 47
gcaaatctac tgaaacgctc ctctgatacc aattccgccg cttg        44

<210> SEQ ID NO 48
<211> LENGTH: 44
<212> TYPE: DNA
<213> ORGANISM: artificial
<220> FEATURE:
<223> OTHER INFORMATION: fTA4-F primer

<400> SEQUENCE: 48
ggatgatggt gatatcaaaa gcgtttcagt agatttgcct ggtg        44

<210> SEQ ID NO 49
<211> LENGTH: 44
<212> TYPE: DNA
<213> ORGANISM: artificial
<220> FEATURE:
<223> OTHER INFORMATION: fTA4-R primer

<400> SEQUENCE: 49
caccaggcaa atctactgaa acgcttttga tatcaccatc atcc        44

<210> SEQ ID NO 50
<211> LENGTH: 38
<212> TYPE: DNA
<213> ORGANISM: artificial
<220> FEATURE:
<223> OTHER INFORMATION: fTA5-F primer

<400> SEQUENCE: 50
gcaagcccaa aaagaccaaa gcgcttcagt agatttgc        38

<210> SEQ ID NO 51
<211> LENGTH: 38
<212> TYPE: DNA
<213> ORGANISM: artificial
<220> FEATURE:
<223> OTHER INFORMATION: fTA5-R primer

<400> SEQUENCE: 51
gcaaatctac tgaagcgctt tggtcttttt gggcttgc        38

<210> SEQ ID NO 52
<211> LENGTH: 46
<212> TYPE: DNA
<213> ORGANISM: artificial
<220> FEATURE:
<223> OTHER INFORMATION: fC9-F primer

<400> SEQUENCE: 52
gaccataaag acaaaggttt gaataaatta aagaaaaac acacag        46

-continued

<210> SEQ ID NO 53
<211> LENGTH: 46
<212> TYPE: DNA
<213> ORGANISM: artificial
<220> FEATURE:
<223> OTHER INFORMATION: fC9-R primer

<400> SEQUENCE: 53
ctgtgtgttt ttcttttaat ttattcaaac ctttgtcttt atggtc         46

<210> SEQ ID NO 54
<211> LENGTH: 40
<212> TYPE: DNA
<213> ORGANISM: artificial
<220> FEATURE:
<223> OTHER INFORMATION: fR1-F primer

<400> SEQUENCE: 54
ccataaagac aaaggtttgc cgcaatatgt tgatgaaacc               40

<210> SEQ ID NO 55
<211> LENGTH: 40
<212> TYPE: DNA
<213> ORGANISM: artificial
<220> FEATURE:
<223> OTHER INFORMATION: fR1-R primer

<400> SEQUENCE: 55
ggtttcatca acatattgcg gcaaacctttt gtctttatgg              40

<210> SEQ ID NO 56
<211> LENGTH: 40
<212> TYPE: DNA
<213> ORGANISM: artificial
<220> FEATURE:
<223> OTHER INFORMATION: fTR1-F primer

<400> SEQUENCE: 56
gcaagcccaa aaagaccaac cgcaatatgt tgatgaaacc               40

<210> SEQ ID NO 57
<211> LENGTH: 40
<212> TYPE: DNA
<213> ORGANISM: artificial
<220> FEATURE:
<223> OTHER INFORMATION: fTR1-R primer

<400> SEQUENCE: 57
ggtttcatca acatattgcg gttggtcttt ttgggcttgc               40

<210> SEQ ID NO 58
<211> LENGTH: 273
<212> TYPE: PRT
<213> ORGANISM: Borrelia afzelii

<400> SEQUENCE: 58

Met Lys Lys Tyr Leu Leu Gly Ile Gly Leu Ile Leu Ala Leu Ile Ala
1 5 10 15

Cys Lys Gln Asn Val Ser Ser Leu Asp Glu Lys Asn Ser Ala Ser Val
20 25 30

Asp Leu Pro Gly Glu Met Lys Val Leu Val Ser Lys Glu Lys Asp Lys
35 40 45

Asp Gly Lys Tyr Ser Leu Lys Ala Thr Val Asp Lys Ile Glu Leu Lys
50 55 60

```
Gly Thr Ser Asp Lys Asp Asn Gly Ser Gly Val Leu Glu Gly Thr Lys
 65                  70                  75                  80

Asp Asp Lys Ser Lys Ala Lys Leu Thr Ile Ala Asp Asp Leu Ser Lys
                 85                  90                  95

Thr Thr Phe Glu Leu Phe Lys Glu Asp Gly Lys Thr Leu Val Ser Arg
            100                 105                 110

Lys Val Ser Ser Lys Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys

<210> SEQ ID NO 59
<211> LENGTH: 210
<212> TYPE: PRT
<213> ORGANISM: Borrelia burgdorferi

<400> SEQUENCE: 59

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160
```

```
Lys Thr Asn Gly Thr Lys Thr Lys Gly Ala Glu Glu Leu Gly Lys Leu
            165                 170                 175

Phe Glu Ser Val Glu Val Leu Ser Lys Ala Ala Lys Glu Met Leu Ala
        180                 185                 190

Asn Ser Val Lys Glu Leu Thr Ser Pro Val Val Ala Glu Ser Pro Lys
        195                 200                 205

Lys Pro
    210

<210> SEQ ID NO 60
<211> LENGTH: 691
<212> TYPE: PRT
<213> ORGANISM: Neisseria meningitidis

<400> SEQUENCE: 60

Met Asn Asn Pro Leu Val Asn Gln Ala Ala Met Val Leu Pro Val Phe
1               5                   10                  15

Leu Leu Ser Ala Cys Leu Gly Gly Gly Ser Phe Asp Leu Asp Ser
            20                  25                  30

Val Asp Thr Glu Ala Pro Arg Pro Ala Pro Lys Tyr Gln Asp Val Ser
        35                  40                  45

Ser Glu Lys Pro Gln Ala Gln Lys Asp Gln Gly Gly Tyr Gly Phe Ala
    50                  55                  60

Met Arg Phe Lys Arg Arg Asn Trp Tyr Gln Arg Ala Asn Pro Lys Glu
65              70                  75                  80

Asp Glu Ile Lys Leu Ser Glu Asp Asp Trp Glu Gln Thr Asp Asp Gly
                85                  90                  95

Asp Ile Lys Asn Pro Ser Lys Gln Lys Asn Ile Ile Asn Ala Leu Pro
            100                 105                 110

Gly Asn Asn Glu Gly Ala Leu Leu Gln Asp Ser Ser Gln Glu Asn Gln
        115                 120                 125

Gly Ile Ser Lys Val Lys Asp Tyr His Asn Phe Gln Tyr Val Trp Ser
    130                 135                 140

Gly Phe Phe Tyr Lys Gln Ile Lys Asn Thr Ile Glu Lys Asn Gly Ser
145             150                 155                 160

Ser Ile Thr Ala Ala Arg Asn Gly Pro Asp Gly Tyr Ile Phe Tyr Lys
                165                 170                 175

Gly Lys Asp Pro Ser Arg Lys Leu Pro Val Ser Gly Glu Val Met Tyr
            180                 185                 190

Lys Gly Thr Trp Asp Phe Leu Thr Asp Val Lys Ala Asn Gln Lys Phe
        195                 200                 205

Thr Asp Leu Gly Asn Ala Ser Thr Lys Pro Gly Asp Arg Tyr Ser Ala
    210                 215                 220

Phe Ser Gly Glu Leu Asp Tyr Ile Val Lys Gln Glu Asn Asp Lys Lys
225             230                 235                 240

Asp Gly His Val Gly Leu Gly Leu Thr Thr Glu Ile Thr Val Asp Phe
                245                 250                 255

Glu Lys Lys Thr Leu Ser Gly Lys Leu Ile Lys Asn Asn Ser Val Ile
            260                 265                 270

Thr Thr Asn Asn Asp Lys His Thr Thr Gln Tyr Tyr Ser Leu Glu Ala
        275                 280                 285

Thr Leu Lys Gly Asn Arg Phe Asn Gly Lys Ala Thr Ala Thr Asp Lys
    290                 295                 300

Pro Lys Glu Asn Glu Thr Lys Gln His Pro Phe Val Ser Asp Ser Ser
305             310                 315                 320
```

```
Ser Leu Ser Gly Gly Phe Phe Gly Pro Gln Gly Glu Glu Leu Gly Phe
                325                 330                 335

Arg Phe Leu Ser Asp Asp Lys Lys Val Ala Val Val Gly Ser Ala Lys
            340                 345                 350

Thr Lys Asp Lys Pro Gly Asn Gly Ala Ala Ala Pro Gly Gly Thr Asp
        355                 360                 365

Ala Ala Ala Ser Asn Gly Ala Ala Gly Thr Ser Ser Glu Asn Ser Lys
370                 375                 380

Leu Thr Thr Val Leu Asp Ala Val Glu Leu Lys Ser Gly Gly Lys Glu
385                 390                 395                 400

Val Lys Asn Leu Asp Asn Phe Ser Asn Ala Ala Gln Leu Val Val Asp
                405                 410                 415

Gly Ile Met Ile Pro Leu Leu Pro Lys Asp Ser Glu Ser Gly Asn Thr
            420                 425                 430

Gln Ala Asp Lys Gly Lys Asn Gly Gly Thr Glu Phe Thr Arg Lys Phe
        435                 440                 445

Glu His Thr Pro Glu Ser Asp Lys Lys Asp Ala Gln Ala Gly Thr Ala
    450                 455                 460

Glu Asn Gly Asn Pro Ala Ala Ser Asn Thr Ala Gly Asp Thr Asn Gly
465                 470                 475                 480

Lys Thr Lys Thr Tyr Ala Val Glu Val Cys Cys Ser Asn Leu Asn Tyr
                485                 490                 495

Leu Lys Tyr Gly Leu Leu Thr Arg Lys Thr Ala Gly Asn Thr Gly Glu
            500                 505                 510

Gly Gly Asn Gly Ala Ala Gln Thr Asp Ala Gln Ser Met Phe Leu Gln
        515                 520                 525

Gly Glu Arg Thr Asp Glu Lys Glu Ile Pro Asn Asp Gln Asn Ile Val
    530                 535                 540

Tyr Arg Gly Ser Trp Tyr Gly His Ile Ala Asn Gly Thr Ser Trp Ser
545                 550                 555                 560

Gly Asn Ala Ser Asp Lys Glu Gly Gly Asn Arg Ala Glu Phe Thr Val
                565                 570                 575

Asn Phe Ala Asp Lys Lys Leu Asn Gly Thr Leu Thr Ala Gly Glu Arg
            580                 585                 590

Thr Ser Pro Thr Phe Thr Ile Thr Ala Thr Ile Gln Gly Asn Gly Phe
        595                 600                 605

Glu Gly Thr Ala Lys Thr Gly Asp Asp Gly Phe Ala Leu Asp Thr Lys
    610                 615                 620

Asn Thr Val Asp Thr His Lys Ala His Ile Thr Asp Ala Asn Val Gln
625                 630                 635                 640

Gly Gly Phe Tyr Gly Pro Lys Ala Glu Glu Leu Gly Gly Trp Phe Ala
                645                 650                 655

Tyr Pro Gly Asp Arg Gln Ala Gln Pro Ser Ala Ser Gly Ser Gly Thr
            660                 665                 670

Ser Ala Ala Asn Ser Ala Thr Val Val Phe Gly Ala Lys Arg Gln Gln
        675                 680                 685

Leu Val Gln
    690
```

SURFACE DISPLAY OF ANTIGENS ON GRAM-NEGATIVE OUTER MEMBRANE VESICLES

FIELD OF THE INVENTION

The present invention relates to the field of medicine, in particular the fields of vaccinology, medical microbiology, bacteriology and immunology. More specifically, the invention relates to vaccine composition based on Gram-negative outer membrane vesicles displaying antigens of pathogens, preferably *Borrelia* antigens, and use of these compositions in vaccination.

BACKGROUND OF THE INVENTION

Outer Membrane Vesicles (OMVs) are spherical buddings of the outer membrane (OM) that are spontaneously produced by Gram-negative bacteria. They are composed of OM proteins, LPS, phospholipids, and entrapped periplasmic components. Because of their excellent immunostimulatory properties (1-3) and ease of production, OMVs are receiving more and more attention as vaccine candidates. Immunization studies in mice have demonstrated that OMVs can protect against challenges with various pathogenic bacteria (4-12). For *Neisseria meningitidis*, OMV vaccines have been extensively investigated in clinical trials, and two OMV-based vaccines against *Neisseria* (MenBvac and MeNZB) are already available for human use (13, 14).

Because of their intrinsic adjuvant properties, the use of OMVs as a delivery vehicle for heterologous antigens has gained considerable interest (15). Several studies have demonstrated that the expression of heterologous antigens in the periplasm or OM of Gram-negative bacteria, by fusion of the heterologous protein to signal peptides or carrier proteins of the host, can lead to their inclusion in OMVs (1-3, 16-19). Importantly, such recombinant OMVs can induce an immune response to the heterologous antigen in immunized mice (2, 3, 12, 17, 18), and even protect them against an otherwise lethal challenge with the pathogen from which the antigen originates (3, 17).

To what extent the specific location of a heterologous antigen within the OMV (periplasm/inside of OM/outside of OM) affects the immune response remains an open question. Theoretically, the outer surface of the OMV appears to be the best option, as this provides the best accessibility for the binding of B-cell receptors (17). There is indeed accumulating evidence that surface exposed antigens evoke superior immune responses (20-24), which makes the precise targeting of heterologous antigens to the OMV surface of special interest.

Various expression systems that specifically target the expression of heterologous proteins to the outer surface of bacterial cells have been developed (see (25-29) for reviews). However, many of these systems can only display small parts of proteins and suffer from low expression levels (30). The two most versatile approaches fuse (parts of) heterologous proteins to Ice Nucleation Protein (25, 31) or autotransporters (21, 32-35) to reach the cell surface. Recently, both systems have also been used to decorate the surface of OMVs with multiple enzymes/antigens (21, 31).

Lipoproteins are membrane-bound proteins that are emerging as key targets for protective immunity, because of their excellent immunostimulatory properties and role as virulence factors. For example, OspA (*Borrelia burgdorferi*) and fHbp (*N. meningitidis*) have both been extensively studied as vaccine components against Lyme disease (36-39) and meningitis (40, 41), respectively. Surface expression of heterologous lipoproteins in OMVs has however not been explored so far.

Lipoproteins carry a lipid-modification on their N-terminal cysteine, facilitating the anchoring of hydrophilic proteins in hydrophobic membranes. This highly conserved protein lipidation motif is recognized by the mammalian innate immune system through the Toll like receptor TLR2, providing lipoproteins with superior immunostimulatory properties (44, 45). In Gram-negative bacteria, most lipoproteins are found on the periplasmic side of the inner or outer membrane. They are transferred from the inner membrane to the outer membrane by the Lol (localization of lipoproteins) machinery (46). Lipoproteins that are located on the extracellular side of the outer membrane are less common, and systems or signals guiding transfer over the outer membrane have not yet been elucidated.

In *Borrelia*, lipoproteins seem to be transferred to the outside of the outer membrane by default, so that the surface of this spirochete is unusually rich in lipoproteins (47). One example of a *Borrelia* lipoprotein with a surface localization is OspA, for which detailed knowledge regarding its immunogenicity and structure is available because OspA has been extensively investigated as a vaccine component against Lyme disease.

Lyme disease is the most common vector-borne disease in Europe and the United States. Lyme disease is a multisystemic inflammatory disorder that is caused by infection with spirochetes of the *B. burgdorferi* sensu lato complex as a result of a bite by infected ticks. If an infection is not treated with antibiotics, it can eventually develop into a chronic disease with severe pathology. The only vaccine shortly available for human use (Lymerix) was based on recombinant lipidated OspA. Due to poor sales resulting from claims about auto-immune side-effects, this vaccine was voluntarily withdrawn from the market in 2002, only three years after its introduction (49). However, the side-effect claims were later found to be unsubstantiated (50) and recent Lyme vaccine developments still target OspA, with the much-disputed epitope removed (38, 39).

There is however, still a need in the art for improved vaccine compositions based on Gram-negative outer membrane vesicles displaying antigens of pathogens at their surface, such as *Borrelia* antigens, and use of these compositions in vaccination e.g. against Lyme disease.

SUMMARY OF THE INVENTION

In a first aspect, the invention relates to a fusion lipoprotein comprising an N-terminal and a C-terminal fusion partner, wherein: a) the N-terminal fusion partner comprises in N- to C-terminal order: i) a lipidated N-terminal cysteine; ii) a tether of a surface exposed lipoprotein of a Gram-negative bacterium, wherein preferably the tether is located adjacent to the lipidated N-terminal cysteine; and, preferably, iii) a stretch of at least 5, 10, or 17 contiguous amino acids that are located C-terminally of a tether in the amino acids sequence of a surface exposed lipoprotein of a Gram-negative bacterium; and wherein the N-terminal fusion partner causes expression of the fusion lipoprotein on the extracellular outermembrane surface of a Gram-negative bacterium upon expression therein; and, b) the C-terminal fusion partner comprises at least one epitope of an antigen associated with an infectious disease and/or a tumour, and wherein, preferably, the amino acid sequence of the fusion lipoprotein does not occur in nature. Preferably, in the fusion lipoprotein, the N-terminal fusion partner comprises an N-terminal fragment from a surface exposed lipoprotein of a Gram-negative bacterium and wherein the fragment causes surface expression of the fusion lipoprotein when expressed in the Gram-negative bacterium. Preferably, the N-terminal fragment is from a surface exposed lipoprotein of a Gram-negative bacterium of the genus *Neisseria*, preferably a *Neisseria meningitidis*, *Neisseria gonorrhoeae* or *N. lactamica*, and more preferably the surface exposed lipoprotein is selected from the group consisting of fHbp, LpbB, TbpB, HpuA, NHBA and Ag473.

In a preferred fusion lipoprotein according to the invention, the N-terminal fusion partner at least comprises: a) an amino acid sequence that has at least 60% sequence identity to the amino acid sequence in positions 20-38 of SEQ ID NO: 1, preferably an amino acid sequence that has at least 60% sequence identity to the amino acid sequence in positions 20-50 of SEQ ID NO: 1; b) an amino acid sequence that has at least 60% sequence identity to the amino acid sequence in positions 21-61 or positions 21-63 of SEQ ID NO: 2, preferably an amino acid sequence that has at least 60% sequence identity to the amino acid sequence in positions 21-73 or positions 21-75 of SEQ ID NO: 2; or, c) an amino acid sequence that has at least 60% sequence identity to the amino acid sequence in positions 23-51 of SEQ ID NO: 3, preferably an amino acid sequence that has at least 60% sequence identity to the amino acid sequence in positions 23-63 of SEQ ID NO: 3.

Preferably, in a fusion lipoprotein according to the invention, the C-terminal fusion partner lacks amino acid sequences from a surface exposed lipoprotein from which the sequences of the N-terminal fusion partner are derived.

The C-terminal fusion partner in a fusion lipoprotein of the invention, preferably, comprises or consists of surface exposed epitopes from a proteinaceous antigen of an infectious agent or tumour. More preferably, the C-terminal fusion partner comprises or consists of a surface exposed domain of a surface exposed bacterial protein or lipoprotein. The surface exposed bacterial protein or lipoprotein preferably is a *Borrelia* surface lipoprotein, preferably selected from the group consisting of OspA, OspB, OspC, OspF, VlsE, BbCRASP1, Vsp1, P35 (BBK32), P37 (BBK50), P39, P66, DpbA and BB017. More preferably, the *Borrelia* surface lipoprotein comprises or consists of amino acids 29-273 of SEQ ID NO: 4 or amino acids 29-273 of SEQ ID NO: 58 or amino acids 136-210 of SEQ ID NO: 59.

In a second aspect, the invention pertains to an OMV comprising a fusion lipoprotein of the invention, wherein the OMV preferably is not a detergent-extracted OMV. Suitable OMV that are not detergent-extracted are supernatant OMV or native OMV, wherein preferably the OMV is a native OMV.

An OMV comprising a fusion lipoprotein of the invention, preferably is obtained/obtainable from a Gram-negative bacterium that has one or more genetic modifications selected from the group consisting of: a) a genetic modification causing the bacterium to produce an LPS with reduced toxicity, wherein preferably the genetic modification reduces or eliminates expression of at least one of a lpxL1, lpxL2 and lpxK gene or a homologue thereof and/or increases the expression of at least one of a lpxE, lpxF and pagL genes; b) genetic modification that increases vesicle formation, wherein preferably, the genetic modification reduces or eliminates expression of an ompA gene or homologue thereof, more preferably a rmpM gene or homologue thereof; and, c) genetic modification that prevent proteolytic release of cell surface-exposed lipoprotein, wherein preferably, the genetic modification reduces or eliminates expression of a nalP gene or homologue thereof. The Gram-negative bacterium where the OMV of the invention are produced preferably belongs to a genus selected from the group consisting of *Neisseria*, *Bordetella*, *Escherichia* and *Salmonella*, more preferably the bacterium belongs to a species selected from the group consisting of *Neisseria meningitidis*, *Bordetella pertussis*, *Escherichia coli* and *Salmonella enterica*.

In a third aspect, the invention relates to a pharmaceutical composition comprising an OMV of the invention and a pharmaceutically accepted excipient.

In a fourth aspect, the invention relates to an OMV according to of the invention, or a pharmaceutical composition comprising the OMV, for use as a medicament.

In a fifth aspect, the invention relates to an OMV according to of the invention, or a pharmaceutical composition comprising the OMV, for the prevention or treatment of an infectious disease or tumour associated with the antigen, wherein preferably the infectious disease is a *Borrelia* infection, more preferably a *Borrelia burgdorferi* infection.

In a sixth aspect, the invention relates to a nucleic acid molecule encoding a pre-profusion lipoprotein, wherein upon expression in a Gram-negative bacterium the pre-profusion lipoprotein matures into the fusion lipoprotein of the invention, and wherein preferably the nucleic acid molecule is an expression construct for expression of the pre-profusion lipoprotein in a Gram-negative bacterium.

In a seventh aspect, the invention relates to a Gram-negative bacterial host cell comprising a nucleic acid molecule or an expression construct comprising a nucleic acid sequence encoding the pre-profusion lipoprotein, wherein preferably the Gram-negative bacterium belongs to a genus selected from the group consisting of *Neisseria*, *Bordetella*, *Escherichia* and *Salmonella*, more preferably the bacterium belongs to a species selected from the group consisting of *Neisseria meningitidis*, *Bordetella pertussis*, *Escherichia coli* and *Salmonella enterica*.

In an eighth aspect, the invention relates to a method for producing an OMV comprising a fusion lipoprotein of the invention, wherein the method comprises the steps of: i) cultivating Gram-negative bacterial host cell comprising a nucleic acid molecule or an expression construct comprising a nucleic acid sequence encoding the pre-profusion lipoprotein; ii) optionally extracting the OMV; and, iii) recovering the OMV, wherein the recovery at least comprises removal of the bacteria from the OMV, and wherein preferably, the method is detergent-free.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagines and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5× SSC/5×Denhardt's solution/ 1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), Sambrook and Russell (2001) "Molecular Cloning: A Laboratory Manual ($3^{rd}$ edition), Cold Spring Harbor Laboratory, Cold Spring Harbor Laboratory Press, New York 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The term "peptide" as used herein is defined as a chain of amino acid residues, usually having a defined sequence. As used herein the term peptide is interchangeable with the terms "polypeptide" and "protein". In the context of the present invention, the term "peptide" is defined as being any peptide or protein comprising at least two amino acids linked by a modified or unmodified peptide bond. The term "peptide" refers to short-chain molecules such as oligopeptides or oligomers or to long-chain molecules such as proteins. A protein/peptide can be linear, branched or cyclic. The peptide can include D amino acids, L amino acids, or a combination thereof. A peptide according to the present invention can comprise modified amino acids. Thus, the peptide of the present invention can also be modified by natural processes such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, covalent bonding to a modified or unmodified carbohydrate moiety, bonding with a lipid or a lipid derivative, covalent bonding with a phosphotidylinositol, cross-linking, cyclization, disulfide bond formation, demethylation, cysteine molecule formation, pyroglutamate formation, formylation, gamma-carboxylation, hydroxylation, iodination, methylation, oxidation, phosphorylation, racemization, hydroxylation, etc. Thus, any modification of the peptide which does not have the effect of eliminating the immunogenicity of the peptide, is covered within the scope of the present invention.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature.

Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The term "immune response" as used herein refers to the production of antibodies and/or cells (such as T lymphocytes) that are directed against, and/or assist in the decomposition and/or inhibition of, a particular antigenic entity, carrying and/or expressing or presenting antigens and/or antigenic epitopes at its surface. The phrases "an effective immunoprotective response", "immunoprotection", and like terms, for purposes of the present invention, mean an immune response that is directed against one or more antigenic epitopes of a pathogen, a pathogen-infected cell or a cancer cell so as to protect against infection by the pathogen or against cancer in a vaccinated subject. For purposes of the present invention, protection against infection by a pathogen or protection against cancer includes not only the absolute prevention of infection or cancer, but also any detectable reduction in the degree or rate of infection by a pathogen or of the cancer, or any detectable reduction in the severity of the disease or any symptom or condition resulting from infection by the pathogen or cancer in the vaccinated subject, for example as compared to an unvaccinated infected subject. An effective immunoprotective response in the case of cancer also includes clearing up the cancer cells, thereby reducing the size of cancer or even abolishing the cancer. Vaccination in order to achieve this is also called therapeutic vaccination. Alternatively, an effective immunoprotective response can be induced in subjects that have not previously been infected with the pathogen and/or are not infected with the pathogen or do not yet suffer from cancer at the time of vaccination, such vaccination can be referred to as prophylactic vaccination.

According to the present invention, the general use herein of the term "antigen" refers to any molecule that binds specifically to an antibody. The term also refers to any molecule or molecular fragment that can be bound by an MHC molecule and presented to a T-cell receptor. Antigens can be e.g. proteinaceous molecules, i.e. polyaminoacid sequences, optionally comprising non-protein groups such as carbohydrate moieties and/or lipid moieties or antigens can be e.g. molecules that are not proteinaceous such as carbohydrates. An antigen can be e.g. any portion of a protein (peptide, partial protein, full-length protein), wherein the protein is naturally occurring or synthetically derived, a cellular composition (whole cell, cell lysate or disrupted cells), an organism (whole organism, lysate or disrupted cells) or a carbohydrate or other molecule, or a portion thereof, that is able to elicit an antigen-specific immune response (humoral and/or cellular immune response) in a particular subject, which immune response preferably is measurable via an assay or method.

The term "antigen" is herein understood as a structural substance which serves as a target for the receptors of an adaptive immune response. An antigen thus serves as target for a TCR (T-cell receptor) or a BCR (B-cell receptor) or the secreted form of a BCR, i.e. an antibody. The antigen can thus be a protein, peptide, carbohydrate or other hapten that is usually part of a larger structure, such as e.g. a cell or a virion. The antigen may originate from within the body ("self") or from the external environment ("non-self"). The immune system is usually non-reactive against "self" antigens under normal conditions due to negative selection of T cells in the thymus and is supposed to identify and attack only "non-self" invaders from the outside world or modified/harmful substances present in the body under e.g. disease conditions. Antigens structures that are the target of a cellular immune response are presented by antigen presenting cells (APC) in the form of processed antigenic peptides to the T cells of the adaptive immune system via a histocompatibility molecule. Depending on the antigen presented and the type of the histocompatibility molecule, several types of T cells can become activated. For T-Cell Receptor (TCR) recognition, the antigen is processed into small peptide fragments inside the cell and presented to a T-cell receptor by major histocompatibility complex (WIC).

The term "immunogen" is used herein to describe an entity that comprises or encodes at least one epitope of an antigen such that when administered to a subject, preferably together with an appropriate adjuvant, elicits a specific humoral and/or cellular immune response in the subject against the epitope and antigen comprising the epitope. An immunogen can be identical to the antigen or at least comprises a part of the antigen, e.g. a part comprising an epitope of the antigen. Therefore, to vaccinate a subject against a particular antigen means, in one embodiment, that an immune response is elicited against the antigen or immunogenic portion thereof, as a result of administration of an immunogen comprising at least one epitope of the antigen. Vaccination preferably results in a protective or therapeutic effect, wherein subsequent exposure to the antigen (or a source of the antigen) elicits an immune response against the antigen (or source) that reduces or prevents a disease or condition in the subject. The concept of vaccination is well-known in the art. The immune response that is elicited by administration of a prophylactic or therapeutic composition of the present invention can be any detectable change in any facet of the immune status (e.g., cellular response, humoral response, cytokine production), as compared to in the absence of the administration of the vaccine.

An "epitope" is defined herein as a single immunogenic site within a given antigen that is sufficient to elicit an immune response in a subject. Those of skill in the art will recognize that T cell epitopes are different in size and composition from B cell epitopes, and that T cell epitopes presented through the Class I MEW pathway differ from epitopes presented through the Class II MEW pathway. Epitopes can be linear sequences or conformational epitopes (conserved binding regions) depending on the type of immune response. An antigen can be as small as a single epitope, or larger, and can include multiple epitopes. As such, the size of an antigen can be as small as about 5-12 amino acids (e.g., a peptide) and as large as: a full length protein, including multimeric proteins, protein complexes, virions, particles, whole cells, whole microorganisms, or portions thereof (e.g., lysates of whole cells or extracts of microorganisms).

OMV (also referred to as "blebs") are bi-layered membrane structures, usually spherical, with a diameter in the range of 20-250 nm (sometimes 10-500 nm), that are pinched off from the outer membrane of Gram-negative bacteria. The OMV membrane contains phospholipids (PL) on the inside and lipopolysaccharides (LPS) and PL on the outside, mixed with membrane proteins in various positions, largely reflecting the structure of the bacterial outer membrane from which they pinched off. The lumen of the OMV may contain various compounds from the periplasm or cytoplasm, such as proteins, RNA/DNA, and peptidoglycan (PG), however, unlike bacterial cells, OMV lack the ability to self-replicate. In the context of the present invention three type of OMV can be distinguished depending on the method of their production. sOMV are spontaneous or natural OMV, that are purified and concentrated from culture supernatant, by separating intact cells from the already formed OMVs. Detergent OMV, dOMV, are extracted from cells with detergent, such as deoxycholate, which also reduces the content of reactogenic LPS and of lipoproteins. After detergent extraction dOMV are separated from cells and cellular debris and further purified and concentrated. Finally, the term native nOMV is used herein for OMV that are generated from concentrated dead cells with non-detergent cell disruption techniques, or that are extracted from cells with other (non-disruptive) detergent-free methods, to be able to clearly distinguish them from the wild-type spontaneous OMVs and from the detergent-extracted dOMV.

Any reference to nucleotide or amino acid sequences accessible in public sequence databases herein refers to the version of the sequence entry as available on the filing date of this document.

DETAILED DESCRIPTION OF THE INVENTION

The present invention relates to Gram-negative OMVs comprising surface exposed fusion lipoprotein comprising epitopes of antigens for vaccination purposes. Surface lipoproteins are normally removed from the OMV during conventional detergent-based removal of LPS. However, recent biotechnological developments have led to detergent-free OMV extraction processes, e.g. from in *Neisseria*, that would potentially allow for surface exposed lipoproteins to remain attached to the OMV (42, 43). The present inventors have investigated the possibility for surface expression of antigenic lipoproteins in these so-called native OMVs (nOMVs) including heterologous lipoproteins. Specifically the inventors have tested the heterologous expression of the *Borrelia* OspA lipoprotein in *Neisseria* nOMVs. Because of its surface localization in *Borrelia* and the detailed knowledge regarding its immunogenicity and structure, OspA would be a suitable lipoprotein to test.

Even though the inventors were able to express OspA in *N. meningitidis* cells and nOMVs, they were unable to detect it on the meningococcal cell surface. This indicates mislocalization to the periplasm or the periplasmic side of the OM. Such host-switch induced mislocalization of lipoproteins is not uncommon and probably results from adherence to the surrogate host's sorting rules (51).

Surprisingly we were able to redirect OspA to the cell surface of *Neisseria*, by fusing its globular domain to different parts of fHbp, a well-studied meningococcal surface lipoprotein (41, 48). We show that fusion to specific N-terminal parts of fHbp allows surface expression of the fHbp-OspA fusion constructs. Moreover, we demonstrate that *Neisseria* nOMV expressing these surface-exposed fHbp-OspA hybrids elicit strong antibody responses in immunized mice.

Secondly, we were also able to redirect OspA to the cell surface of *Neisseria*, by fusing its globular domain to different parts of transferrin binding protein B (TbpB), which has been well characterized at the structural level and which is a co-receptor involved in iron piracy (63).

Thirdly, we were able to redirect other proteins, such as OspC and RmpM, to the cell surface of *Neisseria*, including non-borrelial and non-liporoteins (such as RmpM).

In a first aspect the invention pertains to a fusion lipoprotein. The fusion lipoprotein preferably at least comprises an N-terminal and a C-terminal fusion partner.

The N-terminal fusion partner in the fusion lipoprotein is intended to effect expression of the fusion protein on the extracellular surface of the outermembrane of the Gram-negative bacterium wherein the fusion protein is expressed as well as anchoring into that membrane through its covalently attached lipid. To this end, the N-terminal fusion partner in the fusion lipoprotein preferably at least comprises, preferably in N- to C-terminal order: i) a lipidated N-terminal cysteine; ii) a tether of a surface exposed lipoprotein of a Gram-negative bacterium, wherein preferably the tether is located (immediately) adjacent to the lipidated N-terminal cysteine; and, preferably, iii) at least 1 or a stretch of at least 2, 3, 4, 5, 6, 7, 8, 9, 10, 11, 12, 13, 14, 15, 16, 17, 18, 19, 20, 22, 25, 28 or 30 contiguous amino acids that are located immediately C-terminal of a tether in the amino acids sequence of a surface exposed lipoprotein of a Gram-negative bacterium.

The N-terminal fusion partner preferably causes surface expression of the fusion lipoprotein on the extracellular outermembrane surface when expressed in a Gram-negative bacterium. The ability of the N-terminal fusion partner to cause such surface expression of the fusion lipoprotein can be assayed by expression of the fusion lipoprotein in a Gram-negative bacterium and detection of the fusion lipoprotein on the outside of the Gram-negative bacterium, e.g. using an antibody against the fusion lipoprotein, preferably an antibody against the C-terminal fusion partner, whereby the bound antibody preferably is detected by immunofluorescence, e.g. as described in Examples 1.5 and 2.3 herein. In a preferred assay for determining the ability of the N-terminal fusion partner to cause surface expression, the N-terminal fusion partner is fused to a C-terminal fusion partner that is known to be capable of surface expression as (part of) a lipoprotein on the extracellular outermembrane surface of a Gram-negative bacterium.

A suitable C-terminal fusion partner for this purpose is e.g. the globular domain of a *Borrelia* OspA lipoprotein, preferably the globular domain of a *Borrelia burgdorferi* OspA lipoprotein, whereby preferably the globular domain consists of the amino acid sequence of positions 29-273 of an OspA lipoprotein, e.g. the amino acid sequence of positions 29-273 of SEQ ID NO: 4, as used in the Examples herein.

An alternative suitable C-terminal fusion partner for testing the ability of the N-terminal fusion partner to cause surface expression, comprises or consists e.g. of the globular domain of a *Borrelia afzelii* OspA lipoprotein, whereby preferably the globular domain consists of e.g. the amino acid sequence of positions 29-273 of SEQ ID NO: 58, as used in the Examples herein.

Another alternative suitable C-terminal fusion partner for testing the ability of the N-terminal fusion partner to cause surface expression, comprises or consists e.g. of (a fragment of) the globular domain of a *Borrelia* OspC lipoprotein, preferably a *B. burgdorferi* OspC lipoprotein, whereby preferably the fragment consists of the amino acid sequence of positions 136-210 of an OspC lipoprotein, e.g. the amino acid sequence of positions 136-210 of SEQ ID NO: 59, as used in the Examples herein.

Alternatively, the C-terminal fusion partner for testing the ability of the N-terminal fusion partner to cause surface expression, preferably comprises or consists of a domain of a periplasmic bacterial protein. Preferably the domain of a periplasmic bacterial protein is from a bacterium selected from a genus consisting of Bordetella, Borrelia, Coxiella, Neisseria and any of the other pathogenic bacterial genera mentioned above. The domain of the periplasmic bacterial protein preferably associates with peptidoglycan and/or preferably is the C-terminal domain of the protein. More preferably, the domain of the periplasmic Neisseria protein is derived from RmpM, more preferably the Neisseria periplasmic protein comprises or consists of amino acids 90-242 of SEQ ID NO: 7, as used in the Examples herein.

In a preferred assay for the determining the ability of the N-terminal fusion partner to cause surface expression, the fusion lipoprotein is expressed in a Gram-negative bacterial host cell that is of the same species as the bacterium from which the majority of the sequences in the N-terminal fusion partner are obtained/obtainable, i.e. the bacterium contributing the highest number of individual amino acids to the N-terminal fusion partner. Thus, preferably the N-terminal fusion partner at least causes expression on the extracellular outermembrane surface of a Gram-negative bacterium of a fusion lipoprotein consisting of the N-terminal fusion partner fused (at its C-terminus) to the amino acid sequence of positions 29-273 of SEQ ID NO: 4 (or alternatively to the amino acid sequence of positions 29-273 of SEQ ID NO: 58, or the amino acid sequence of positions 136-210 of SEQ ID NO: 59 or to the amino acid sequence of positions 90-242 of SEQ ID NO: 7), upon expression in the Gram-negative bacterium, whereby the Gram-negative bacterium is of the same species as the bacterium from which the majority of the sequences in the N-terminal fusion partner are obtainable. Preferably, surface expression of this fusion lipoprotein is detected by immunofluorescence microscopy with an anti-OspA (polyclonal) antibody, e.g. the anti-OspA (rabbit) antibody 200-401-C13S as available from Rockland Immunochemicals Inc. (Limerick, Pa. 19468, USA; www.rockland-inc.com). Moreover, surface expression of the OspC fusion lipoprotein is preferably detected with an anti-OspC (polyclonal) antibody, e.g. the anti-OspC antibody 200-401-C11S as available from Rockland Immunochemicals Inc. The surface expression of the RmpM fusion lipoprotein is preferably detected with an anti-RmpM antibody MN2D6D as available from the National Institute for Public Health and the Environment, Bilthoven, the Netherlands.

The lipidated cysteine preferably is the most N-terminal amino acid in the mature fusion lipoprotein of the invention. Bacterial lipoproteins are initially translated as preprolipoproteins, which possess an N-terminal signal peptide of around 20 amino acids with typical characteristic features of the signal peptides of secreted proteins (Inouye et al., 1977, PNAS USA 74: 1004-1008). A conserved sequence at the C-terminal region of the signal peptides, referred to as lipobox, [LVI][ASTVI][GAS]C, is modified through the covalent attachment of a diacylglycerol moiety to the thiol group on the side chain of the indispensable cysteine residue (Babu et al., 2006, J. Bacteriol. 188: 2761-2773). This modification is catalyzed by the enzyme lipoprotein diacylglyceryl transferase, resulting in a prolipoprotein consisting of a diacylglycerol moiety linked by a thioester bond to the protein. The prolipoprotein is subsequently processed by the lipoprotein signal peptidase, which cleaves off the signal peptide, leaving the lipidated cysteine as the new N-terminal residue forming the mature lipoprotein. The mature lipoprotein can have an additional amide-linked fatty acid attached by a lipoprotein N-acyl transferase to the N-terminal cysteine residue.

Downstream (in N- to C-terminal order) of the lipidated cysteine, the N-terminal fusion partner preferably comprises a tether of a surface exposed lipoprotein of a Gram-negative bacterium, whereby preferably the tether is located immediately adjacent to the N-terminal lipidated cysteine, meaning that no additional amino acids are present between the N-terminal lipidated cysteine and the tether. Tethers of Gram-negative surface lipoproteins are usually stretches of 5-50 amino acids with a low propensity of forming a secondary structure, such as an α-helix or a β-strand or β-sheet, and which provide an unordered and flexible lipopeptide tether to the remainder of the exposed structural protein. Without wishing to be bound by theory, the tether is further thought to be important in determining the location of the lipoprotein, e.g. whether it is directed to the outer membrane by the lipoprotein localization machinery (Lol) or is retained at the inner membrane. Particularly the identity of the amino acid in position +2, i.e. immediately adjacent to the N-terminal lipidated cysteine has been reported to be important for determining the location of the lipoprotein, even though this does not appear to be a universal rule and other amino acids more downstream in tether may also play a role in locating the lipoprotein (Kovacs-Simon et al., 2011, Infect. Immun. 79: 548-561). Furthermore, as also shown by the present inventors, the ability of a tether to effect surface expression of a lipoprotein can be species-specific. Preferably therefore, the tether in the fusion protein is a tether from a surface expressed lipoprotein of a bacterial genus, more preferably of a bacterial species that is the same as the bacterial host cell of the invention in which the fusion lipoprotein is expressed. The tether in the fusion lipoprotein is thus preferably homologous to the host cell of the invention in which the fusion lipoprotein is expressed.

Preferred tethers for expression of a fusion lipoprotein of the invention in a Neisserial host cell are tethers from surface expressed Neisserial lipoproteins such as fHbp (factor H binding protein), LpbB (Lactoferrin binding protein), TbpB Transferrin binding protein), HpuA (hemoglobin-haptoglobin utilization protein), NHBA (Neisseria Heparin Binding Antigen, GNA2132) and Ag473 (Chu et al., 2012, PLoS One 7 (7): e40873; Genbank NP_274477.1) from a Neisseria such as e.g. N. meningitidis, N. gonorrhoeae and N. lactamica. A preferred tether for expression of a fusion lipoprotein of the invention in a Neisserial host cell is therefore a tether selected from the group consisting of a) an amino acid sequence that has at least 60, 69, 76, 84, 92 or 100% sequence identity to the amino acid sequence in positions 20-33 of SEQ ID NO: 1; b) an amino acid sequence that has at least 60, 68, 75, 81, 87, 93 or 100% sequence identity to the amino acid sequence in positions 21-56 or positions 21-58 of SEQ ID NO: 2 (e.g. derived from TbpB, strain MC58) or an amino acid sequence that has at least 60, 68, 75, 81, 87, 93 or 100% sequence identity to the amino acid sequence in positions 21-56 or positions 21-58 of SEQ ID NO: 60 (e.g. derived from TbpB, strain H44/76); and, c) an amino acid sequence that has at least 60, 66, 70, 75, 79, 83, 87, 91, 95 or 100% sequence identity to the amino acid sequence in positions 23-46 of SEQ ID NO: 3, wherein preferably the tether has an amino acid sequence that naturally occurs in a surface expressed Gram-negative lipoprotein. It is understood that the N-terminal lipidated cysteine is included in the definitions of the amino acid sequences of the tether in a), b) and c) above.

In a preferred embodiment, the N-terminal partner in a fusion lipoprotein of the invention comprises further sequences from a surface exposed lipoprotein of a Gram-negative bacterium. The inventors have found that an N-terminal fusion partner comprising additional amino acid sequences of a surface exposed lipoprotein of a Gram-negative bacterium can significantly increase the level of surface expression of the fusion lipoprotein as e.g. exemplified by the fA1 fusion lipoprotein. The N-terminal fusion partner therefore preferably comprises at least one or more contiguous amino acids from an amino acids sequence of a surface exposed lipoprotein of a Gram-negative bacterium, wherein preferably these one or more contiguous amino acids are present immediately C-terminal of a tether in the surface exposed lipoprotein from which they are derived. The length of this stretch of amino acids preferably is as indicated above.

In a preferred embodiment the additional stretch of amino acids from a surface exposed lipoprotein comprise an amino acid sequence with a propensity to form a local element or segment of secondary structure, or a part thereof, such as an α-helix, a β-strand or a β-pleated sheet. A preferred additional stretch of amino acids from a surface exposed lipoprotein that can be included for increasing the level of surface expression of the fusion lipoprotein is a contiguous stretch of at least 3, 4, 5, 6, 7, 8, 9, 10, 11, 12, 13, 14, 15, 16 or 17 amino acids taken from the amino acid sequence in positions 34-50 of a Neisserial fHbp protein, more preferably of a N. meningitidis fHbp protein, most preferably contiguous stretch is taken from the amino acid sequence in positions 34-50 of SEQ ID NO: 1. Preferably, amino acid in position 34 is included in the contiguous stretch taken from the amino acid sequence in positions 34-50 of a Neisserial fHbp protein such that the stretch is located immediately C-terminal of a tether in the amino acids sequence of Neisserial fHbp protein.

In the N-terminal partner of a fusion lipoprotein of the invention the tether of a surface exposed lipoprotein of a Gram-negative bacterium and the one or more contiguous amino acids from an amino acids sequence of a surface exposed lipoprotein of a Gram-negative bacterium, i.e. elements ii) and iii) above, can be obtained/obtainable from amino acid sequences from two different surface exposed lipoproteins (that could even be from two different Gram-negative bacteria), but preferably they are obtained/obtainable from an amino acid sequence of one and the same surface exposed lipoprotein.

In one embodiment, in the fusion lipoprotein of the invention, the N-terminal fusion partner in the lipoprotein comprises an N-terminal fragment from a surface exposed lipoprotein of a Gram-negative bacterium, which N-terminal fragment at least includes the lipidated cysteine. Preferably the N-terminal fusion partner in the lipoprotein comprises an N-terminal fragment from a mature surface exposed lipoprotein, wherein the mature lipoprotein is understood to have a lipidated cysteine as N-terminus. Preferably, the N-terminal fusion partner of the lipoprotein comprises at least 10, 11, 12, 13, 14, 15, 16, 17, 18, 19, 20, 22, 25, 28, 30, 31, 32, 35, 38 or 40 contiguous amino acids from an N-terminal fragment of a mature surface exposed lipoprotein including and starting from the lipidated cysteine at the N-terminus of the fragment. Preferably, the N-terminal fragment causes surface expression of the fusion lipoprotein when expressed in the Gram-negative bacterium. The ability of the N-terminal fragment to effect surface expression of the fusion lipoprotein can be assayed as described above.

In a preferred embodiment, the fusion lipoprotein of the invention is a fusion lipoprotein that can be used for expression in a Neisserial host cell. In the N-terminal partner of such a fusion lipoprotein, preferably, the tether of a surface exposed lipoprotein of a Gram-negative bacterium and the one or more contiguous amino acids from an amino acids sequence of a surface exposed lipoprotein of a Gram-negative bacterium, i.e. elements ii) and iii) above, and/or the N-terminal fragment as defined above, are obtained/obtainable from amino acid sequences from a bacterium of the genus Neisseria, preferably a Neisseria meningitidis or Neisseria gonorrhoeae or N. lactamica. More preferably, the Neisserial surface exposed lipoprotein from which the amino acid sequences for the N-terminal fusion partner are obtained/obtainable is selected from the group consisting of fHbp, LpbB, TbpB, HpuA, NHBA and Ag473.

In another preferred embodiment, in a fusion lipoprotein of the invention that can be used for expression in a Neisserial host cell, the N-terminal partner of the fusion lipoprotein comprises at least: a) an amino acid sequence that has at least 60% sequence identity to the amino acid sequence in position 20 to one of positions 34, 35, 36, 37, 38, 39, 40, 41, 42, 43, 44, 45, 46, 47, 48, 49 and 50 of SEQ ID NO: 1; b) an amino acid sequence that has at least 60% sequence identity to the amino acid sequence in position 21 to one of positions 56, 57, 58, 59, 60, 61, 62, 63, 64, 65, 66, 67, 68, 69, 70, 71, 72, 73, 74 and 75 of SEQ ID NO: 2; or, c) an amino acid sequence that has at least 60% sequence identity to the amino acid sequence in position 23 to one of positions 46, 47, 48, 49, 50, 51, 52, 53, 54, 55, 56, 57, 58, 59, 60, 61, 62 and 63 of SEQ ID NO: 3.

The C-terminal fusion partner in the fusion lipoprotein is preferably intended to generate an immune response against at least one epitope of an antigen associated with an infectious disease and/or a tumour, which epitope is present in the C-terminal fusion partner. The C-terminal fusion partner in the fusion lipoprotein in principle can be any amino acid sequence comprising the at least one epitope.

It is understood herein that a fusion lipoprotein of the invention preferably is a fusion protein wherein the N- and C-terminal fusion partners are fused by normal protein synthesis in the Gram-negative host cell wherein the fusion lipoprotein is expressed (see below) by translation of nucleic acid sequences coding for respectively the N- and C-terminal fusion partners, which coding sequences are operably linked in frame by standard recombinant DNA techniques. Optionally, the N- and C-terminal fusion partners are fused through a linker amino acid sequence, for which the coding sequence is operably linked in frame with the respective nucleic acid sequences coding for the N- and C-terminal fusion partners. The linker amino acid sequence preferably is amino acid sequence of 2, 3, 4, 5, 6, 7, 8, 9, 10, 12, 15, or 20 amino acid. A preferred linker comprises an amino acid sequence composed of the amino acids glycine, proline, serine and alanine. More preferably, linker comprises the amino acid sequence PGGSGA (SEQ ID NO: 5), or repeats of (parts) thereof.

The C-terminal fusion partner in the fusion lipoprotein in principle can be any amino acid sequence comprising the at least one epitope. Preferably, the C-terminal fusion partner comprises an amino acids sequence of at least 5, 10, 15, 30, 50, 100, 150, 200, 250, 300, 350 or 400 amino acids and/or no more than 800, 700, 600, 500 or 450 amino acids. Preferably, the C-terminal fusion partner in the fusion lipoprotein of the invention is compatible with surface expression of the fusion lipoprotein when expressed in the Gram-negative bacterium. The compatibility of the C-terminal fusion partner with surface expression of the fusion lipoprotein can be assayed as described above.

In one embodiment, the C-terminal fusion partner in the fusion lipoprotein of the invention is heterologous to the N-terminal fusion partner. A C-terminal fusion partner that is heterologous to the N-terminal fusion partner is understood to mean that the amino acid sequences in the C-terminal fusion partner originate from one or more protein that are different than the protein from which the amino acid sequences in the N-terminal fusion partner originate. The heterologous C-terminal fusion partner can originate from the same organism as the N-terminal fusion partner, or the N- and C-terminal fusion partners can be each from a different organism. Preferably, in a fusion lipoprotein according to the invention, the C-terminal fusion partner lacks amino acid sequences from the surface exposed lipoprotein from which the sequences of the N-terminal fusion partner are derived. More preferably, the C-terminal fusion partner lacks a (contiguous) amino acid sequence of at least 3, 4, 5, 6, 7, 8, 9, 10, 15 or at least 20 amino acids from the surface exposed lipoprotein from which the sequences of the N-terminal fusion partner are derived. Thus, preferably the C-terminal fusion partner comprises or consists of amino acids sequences originating from one or more proteinaceous antigens that are different from the surface exposed lipoprotein from which the amino sequences of N-terminal fusion partner originate.

The C-terminal fusion partner in the fusion lipoprotein of the invention, preferably comprises at least one epitope for inducing and/or enhancing an immune response against an antigen comprising the epitope. Preferably, a B-cell, humoral or antibody response is elicited by the epitope in the C-terminal fusion partner. Preferably the epitope in the C-terminal fusion partner elicits a protective and/or neutralizing antibody response. Alternatively and/or additionally, the C-terminal fusion partner comprises epitopes that elicit a T cell response. A preferred T-cell response induced and/or enhanced by an immunogenic peptide comprises at least one of an HLA class I restricted CTL response and an HLA class II restricted Th response. More preferably the T-cell response consists of both an HLA class I restricted CTL response and simultaneously an HLA class II restricted Th response, and may be advantageously accompanied by a B-cell response.

The C-terminal fusion partner in the fusion lipoprotein can comprise one or more epitopes from a wide range of antigens of pathogens (infectious agents) and/or tumours. For example, the C-terminal fusion partner may comprise one or more epitopes from antigens from pathogens and infectious agents such as viruses, bacteria, fungi and protozoa. Some examples of pathogenic viruses causing infections or tumours from which epitopes from antigens may be derived include: hepatitis (A, B, or C), herpes virus (e.g., VZV, HSV-I, HAV-6, HSV-II, and CMV, Epstein Barr virus), adenovirus, SV40 virus (causing mesothelioma), influenza virus, flaviviruses, ebola virus, echovirus, rhinovirus, coxsackie virus, coronavirus, respiratory syncytial virus (RSV), mumps virus, rotavirus, measles virus, rubella virus, parvovirus, vaccinia virus, HTLV virus, dengue virus, molluscum virus, poliovirus, rabies virus, JC virus, arboviral encephalitis virus, and human immunodeficiency virus (HIV virus; e.g., type I and II), human papilloma virus (HPV). Some examples of pathogenic bacteria causing infections from which epitopes from antigens may be derived include: *Borrelia, Listeria, Escherichia, Chlamydia, Coxiella, Rickettsial bacteria, Mycobacteria, Staphylococci, Streptocci, Pneumonococci, Meningococci, Gonococci, Klebsiella, Proteus, Serratia, Pseudomonas, Legionella, Diphtheria, Salmonella, Bacilli, Bordetella*, bacteria causing Cholera, Tetanus, Botulism, Anthrax, Plague, Leptospirosis, Whooping cough and Lymes disease. Some examples of pathogenic fungi causing infections from which epitopes from antigens may be derived include: *Candida* (e.g., *albicans, krusei, glabrata, tropicalis*), *Cryptococcus neoformans, Aspergillus* (e.g., *fumigatus, niger*), fungi of the genus *Mucorales* (*Mucor, Absidia, Rhizopus*), *Sporothrix schenkii, Blastomyces dermatitidis, Paracoccidioides brasiliensis, Coccidioides immitis* and *Histoplasma capsulatum*. Some examples of pathogenic parasites causing infections from which epitopes from antigens may be derived include: *Entamoeba histolytica, Balantidium coli, Naegleria, Fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii* and *Plasmodium falciparis*.

In addition, the C-terminal fusion can comprise one or more epitopes from a wide range of tumour antigens, including e.g. MAGE, BAGE, RAGE, GAGE, SSX-2, NY-ESO-1, CT-antigen, CEA, PSA, p53, XAGE and PRAME but also virally induced malignancies, comprising Human papilloma virus (HPV), Kaposi sarcoma herpes virus (KSHV), Epstein Bar virus induced lymphoma's (EBV). Other examples of tumour antigens from which epitopes for use in the present invention may be derived are various ubiquitously expressed self-antigens that are known to be associated with cancer, which include e.g. p53, MDM-2, HDM2 and other proteins playing a role in p53 pathway, molecules such as surviving, telomerase, cytochrome P450 isoform 1B1, Her-2/neu, and CD19 and all so-called house hold proteins. Cancers that may be treated in accordance with the present invention are selected among the following list: lung, colon, esophagus, ovary, pancreas, skin, gastric, head and neck, bladder, sarcoma, prostate, hepatocellular, brain, adrenal, breast, endometrial, mesothelioma, renal, thyroid, hematological, carcinoid, melanoma, parathyroid, cervix, neuroblastoma, Wilms, testes, pituitary and pheochromocytoma cancers.

In one embodiment, the C-terminal fusion partner comprises or consists of one or more surface exposed epitopes from a proteinaceous antigen of an infectious agent or tumour. The C-terminal fusion partner can e.g. comprises or consists of an extracellular and/or surface exposed domain of the proteinaceous antigen of an infectious agent or tumour.

In a preferred embodiment, the C-terminal fusion partner comprises or consists of a surface exposed domain of a surface exposed bacterial protein or lipoprotein. Preferably the surface exposed domain of a surface exposed protein or lipoprotein from a bacterium selected from a genus consisting of *Bordetella, Borrelia, Coxiella Neisseria* and any of the other pathogenic bacterial genera mentioned above. More preferably the surface exposed domain is of a surface exposed *Borrelia* protein or lipoprotein selected from the group consisting of OspA, OspB, OspC, OspF, VlsE, BbCRASP1, Vsp1, P35 (BBK32), P37 (BBK50), P39, P66, DpbA and BB017, as described in one or more of Schuijt et al. (2011, Trends in parasitology. 27(1):40-7), Steere and Livey (2013; 49 in the reference list), Embers and Narasimhan (2013, Frontiers in cellular and infection microbiology. 3:6) and Small et al. (2014, PloS one. 9(2): e88245). Most preferably, the surface exposed domain comprises or consists of amino acids 29-273 of SEQ ID NO: 4, amino acids 29-273 of SEQ ID NO: 58, or amino acids 136-210 of SEQ ID NO: 59.

The amino acid sequence of the C-terminal fusion partner may also have 35%, 40%, 45%, 50%, 55%, 60%, 65%, 70%, 75%, 80%, 85%, 90%, 95%, 96%, 97%, 98%, or 99% sequence identity with the sequence of amino acids 29-273 of SEQ ID NO: 4, amino acids 29-273 of SEQ ID NO: 58 or with amino acids 136-210 of SEQ ID NO: 59.

In a second aspect, the invention pertains to an OMV comprising a fusion lipoprotein as herein defined above. OMV (also known as "blebs") for use in vaccines have traditionally been prepared by detergent extraction (a dOMV purification process), wherein detergents such deoxycholate are used to remove LPS and increase vesicle release. The LPS of most Gram-negative bacteria, such as *N. meningitidis* is highly toxic, yet residual amounts (approx. 1%) are needed in OMV to maintain vesicle structure and for adjuvant activity. However, along with most of the LPS, the detergent extraction process also removes lipoproteins and is therefore not suitable for producing OMV comprising fusion lipoproteins of the present invention. An OMV comprising a fusion lipoprotein according to the invention therefore preferably is not a detergent-extracted OMV. It is understood however, that a process for preparing an OMV that is not a detergent-extracted OMV does not exclude the use of any detergents. The use of low concentration of detergent and/or the use of mild detergents are not excluded as long as most of the fusion lipoprotein according to the invention, i.e. at least 50, 60, 70, 80, 90, 95 or 99% of the fusion lipoprotein, is maintained, e.g. as compared the amount of fusion lipoprotein present in spontaneous or supernatant OMV from an equal amount of the same culture.

A preferred OMV comprising a fusion lipoprotein of the invention is a supernatant or spontaneous OMV, i.e. sOMV as herein defined above, or a native OMV, i.e. nOMV as herein defined above. nOMV can be prepared as described in Example 1.6 herein. Further methods for preparing nOMV are e.g. described in Saunders et al. (1999, Infect Immun, 67, 113-119), van de Waterbeemd et al. (2012, Vaccine, 30: 3683-3690) and in WO2013006055 and methods for preparing sOMV are e.g. described in van de Waterbeemd et al. (2013, PLoS ONE, 8(1): e54314. doi: 10.1371/journal.pone.0054314) and in Lee et al. (2007, Proteomics, 7: 3143-3153), all of which are incorporated herein by reference.

The OMV comprising a fusion lipoprotein of the invention are preferably obtained/obtainable from a Gram-negative bacterium that has a genetic modification selected from the group consisting of: (i) a genetic modification that alters the lipopolysaccharide (LPS) biosynthesis pathway, preferably in order to obtain less endotoxic and reactogenic variants; (ii) a genetic modification that causes outer membrane retention of normally secreted antigens; (iii) a genetic modification that increases OMV production by removing outer membrane anchor proteins; (iv) a genetic modification that removes immune-modulating components which may trigger an undesired type of immune response; and, (v) a genetic modification that introduces expression of heterologous antigens from other pathogens than the host OMV producing strain.

The OMV comprising a fusion lipoprotein of the invention are preferably obtained/obtainable from a Gram-negative bacterium that has a genetic modification causing the bacterium to produce an LPS with reduced toxicity but which LPS retains at least part of its adjuvant activity, wherein preferably the genetic modification reduces or eliminates expression of at least one of a lpxL1, lpxL2 and lpxK gene or a homologue thereof and/or increases the expression of at least one of a lpxE, lpxF and/or pagL genes. More preferably, the Gram-negative bacterium has a genetic modification reduces or eliminates expression of an lpxL1 gene or a homologue thereof having at least 35%, 40%, 45%, 50%, 55%, 60%, 65%, 70%, 75%, 80%, 85%, 90%, 95%, 96%, 97%, 98%, or 99% sequence identity with the amino acid sequence of SEQ ID NO: 6.

The Gram-negative bacterium from which the OMV comprising a fusion lipoprotein of the invention are obtained/obtainable, further preferably comprises a genetic modification that reduces or eliminates expression of a gene encoding an anchor protein between outer membrane and peptidoglycan in order to increase vesicle formation and thereby increase OMV yield. A suitable genetic modification for this purpose e.g. reduces or eliminates expression of an OmpA homologue, which are commonly found in Gram-negative bacteria, e.g. the RmpM protein in *Neisseria* (Steeghs et al., 2002 Cell Microbiol, 4: 599-611; van de Waterbeemd et al., 2010 Vaccine, 28: 4810-4816). Thus, preferably, the Gram-negative bacterium has a genetic modification reduces or eliminates expression of an rmpM gene or a homologue thereof having at least 35%, 40%, 45%, 50%, 55%, 60%, 65%, 70%, 75%, 80%, 85%, 90%, 95%, 96%, 97%, 98%, or 99% sequence identity with the amino acid sequence of SEQ ID NO: 7.

In one embodiment, the OMV comprising a fusion lipoprotein of the invention are preferably obtained/obtainable from a Gram-negative that has a genetic modification that reduces or eliminates expression of a nalP gene or a homologue thereof. The NalP protease has been identified as responsible for proteolytic release of the LbpB cell surface-exposed lipoprotein in *Neisseria* (Roussel-Jazédé et al., 2010, Infect Immun 78: 3083-3089). In order to prevent proteolytic release of fusion lipoprotein of the invention, preferably, the Gram-negative host for producing the OMV comprising a fusion lipoprotein of the invention has a genetic modification that reduces or eliminates expression of a nalP gene or a homologue thereof. More preferably, expression of a nalP gene or homologue thereof is reduced or eliminated in a Gram-negative host for producing the OMV comprising a fusion lipoprotein wherein the N-terminal fusion partner comprises LbpB amino acid sequences. Preferably therefore, the Gram-negative bacterium has a genetic modification reduces or eliminates expression of an nalP gene or a homologue thereof having at least 35%, 40%, 45%, 50%, 55%, 60%, 65%, 70%, 75%, 80%, 85%, 90%, 95%, 96%, 97%, 98%, or 99% sequence identity with the amino acid sequence of SEQ ID NO: 8.

A Gram-negative bacterial host cell for producing the OMV comprising a fusion lipoprotein of the invention can further have one or more genetic modifications that reduce or eliminate the expression of a gene selected from the group consisting of cps, ctrA, ctrB, ctrC, ctrD, exbB, exbD, frpB, galE, htrB, msbB, lpbB, lpxK, lpxL1, nmb0033, opA, opC, rmpM, phoP, pilC, pmrE, pmrF, porA, porB, siaA, siaB, siaC, said, synA, synB, sync, tbpA and tbpB, or homologues thereof; many of these mutations are reviewed in WO02/09746.

A Gram-negative bacterial host cell for producing the OMV comprising a fusion lipoprotein of the invention, preferably is bacterial host cell that belongs to a genus selected from the group consisting of *Neisseria, Bordetella, Escherichia* and *Salmonella*, more preferably is bacterial host cell that belongs to a species selected from the group consisting of *Neisseria meningitidis*, *Bordetella pertussis*, *Escherichia coli* and *Salmonella enterica*.

In a further aspect, the invention relates to a pharmaceutical composition comprising an OMV as defined herein above, comprising a fusion lipoprotein according to the invention. The composition further preferably comprises a pharmaceutically acceptable carrier, medium or delivery vehicle as are conventionally known in the art (see e.g. "Handbook of Pharmaceutical Excipients", Rowe et al eds. 7th edition, 2012, www.pharmpress.com). Pharmaceutically acceptable stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver the active ingredients, i.e. the OMV comprising the fusion protein of the invention to the patient.

Pharmaceutically acceptable carriers for parenteral delivery are exemplified by sterile buffered 0.9% NaCl or 5% glucose optionally supplemented with a 20% albumin. Alternatively, the OMV comprising the fusion protein can be suspended in Phosphate buffer saline (PBS). Preparations for parental administration must be sterile. The parental route for administration of the OMV comprising the fusion protein of the invention is in accord with known methods, e.g. injection or infusion by intravenous, intraperitoneal, intramuscular, intraarterial or intralesional routes. A typical pharmaceutical composition for intramuscular injection would be made up to contain, for example, 1-10 ml of phosphate buffered saline comprising the effective dosages of the OMV comprising the fusion protein of the invention. Methods for preparing parenterally administrable compositions are well known in the art and described in more detail in various sources, including, for example, "Remington: The Science and Practice of Pharmacy" (Ed. Allen, L. V. 22nd edition, 2012, www.pharmpress.com).

In another aspect, the invention pertains to an OMV comprising a fusion protein of the invention or a pharmaceutical composition comprising said OMV for use as a medicament.

In another aspect, the invention pertains to an OMV comprising a fusion protein of the invention or a pharmaceutical composition comprising said OMV for the prevention or treatment of an infectious disease or tumour associated with an antigen as herein defined above. Preferably, the infectious disease is a *Borrelia* infection, more preferably a *Borrelia burgdorferi* infection.

In this aspect, the invention thus relates to a method for vaccination against, or for prophylaxis or therapy of an infectious disease or tumour by administration of a therapeutically or prophylactically effective amount of (a pharmaceutical composition comprising) an OMV comprising a fusion protein of the invention, to a subject in need of prophylaxis or therapy. The invention also relates to an OMV comprising a fusion protein of the invention for use as a medicament, preferably a medicament for vaccination against, or for prophylaxis or therapy of an infectious disease or tumour.

In yet another aspect, the invention relates to a nucleic acid molecule encoding a pre-profusion lipoprotein, wherein upon expression in a Gram-negative bacterium the pre-profusion lipoprotein matures into the fusion lipoprotein as defined herein above, and wherein preferably the nucleic acid molecule is an expression construct for expression of the pre-profusion lipoprotein in a Gram-negative bacterium. Means and methods for constructing expression constructs for expression of the protein Gram-negative bacteria are generally well-known in the art.

In again a further aspect, the invention relates to a Gram-negative host cell comprising a nucleic acid molecule or an expression construct as defined above. Preferably the host cell is bacterial host cell that belongs to a genus or species as defined above.

In a final aspect, the invention relates to a method for producing an OMV comprising a fusion lipoprotein of the invention. The method preferably comprises the steps of: a) cultivating a Gram-negative host cell comprising a nucleic acid molecule or an expression construct as defined above for expression in the host cell of a pre-profusion lipoprotein, wherein upon expression in a Gram-negative host cell the pre-profusion lipoprotein matures into the fusion lipoprotein as defined herein above; and, c) recovering the OMV, wherein the recovery at least comprises removal of the bacteria from the OMV. Preferably in the method, the recovery of the OMV in step c) is preceded by a step b), wherein the OMV are extracted. The method for producing OMV comprising a fusion lipoprotein of the invention is further preferably, a detergent-free method as herein defined and described above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIGS. 5A and 5B Schematic overview of TbpB (hatched) and OspA (white) fusion constructs. Amino acid numbering for TbpB and OspA is shown in boxed areas. S.p.=signal peptide. Numbered arrows refer to primers listed in Table 1, forward primers are shown above and reverse primers are shown below the schematic (fusion) genes, positioning of the arrow heads reflects the approximate positioning of the 3' end.

EXAMPLES

1. Materials and Methods 1.1 Antibiotics

Figure 1A:
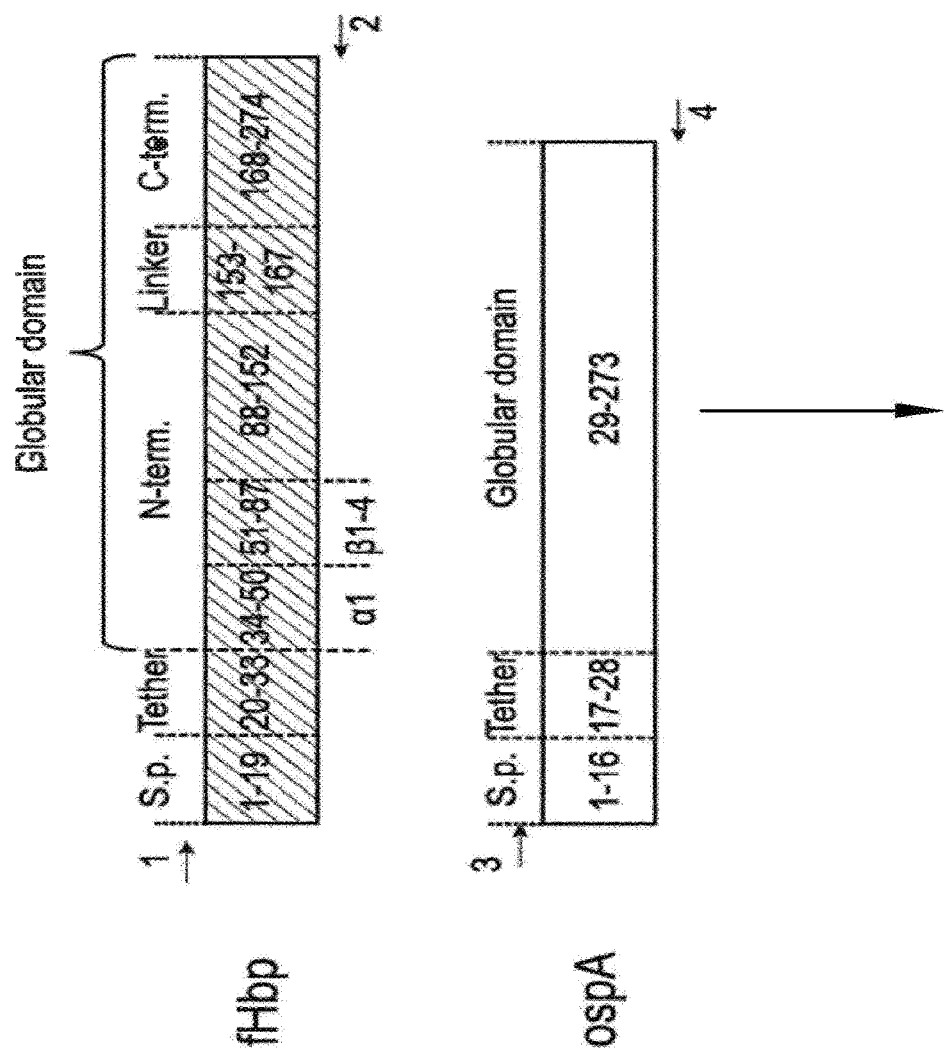
FIGS. 1A, 1B, and 1C. Schematic overview of fHbp (hatched), OspA (white) and fusion constructs. Amino acid numbering for fHbp and OspA is shown in boxed areas. S.p.=signal peptide, α1=N-terminal alpha-helix of fHbp including the subsequent loop, β1-4=first four N-terminal beta-sheets of fHbp. Numbered arrows refer to primers listed in Table 1, forward primers are shown above and reverse primers are shown below the schematic (fusion) genes, positioning of the arrow heads reflects the approximate positioning of the 3'end. The artificial linker (6) that was incorporated in some constructs is shown in white. Note that construct fA1 was used as template to create constructs fA3b and fA5c.

Ampicillin (Amp) and chloramphenicol (Cam) were purchased from Sigma. Stock solution were prepared in Milli-Q (MQ) water, filter-sterilized using a 0.22 µm Steriflip (Milipore), and stored at 4° C.

1.2 Bacterial Strains and Growth Conditions

*Escherichia coli* strains JM109 (Promega) and TOP1OF' (Invitrogen) were used for cloning steps involving vectors pGEM-T Easy and pEN11, respectively. Both strains were grown at 37° C. on Luria Bertani medium (MP Biomedicals) supplemented with 15 gram agar/liter and appropriate antibiotics (50 µg/ml Amp for pGEM-T Easy and 25 µg/ml Cam for pEN11). For blue/white screening of JM109, plates were supplemented with 50 µg/ml 5-bromo-4-chloro-3-indolyl-beta-D-galacto-pyranoside (X-gal, Fermentas) and 0.1 mM isopropyl-beta-D-thiogalactopyranoside (IPTG, Thermo Scientific). Liquid cultures were grown at 37° C. and 200 RPM.

*Neisseria meningitidis* strain HB-1 carrying the lpxL1 deletion (52) was grown on Difco GC medium base supplemented with IsoVitaleX (both Becton Dickinson) at 37° C. in a humid atmosphere containing 5% $CO_2$. Plates were supplemented with 3 µg/ml Cam in case of transformation with pEN11. Liquid cultures were grown in Tryptic Soy Broth (TSB, Becton Dickinson) with 3 µg/ml Cam and 1 mM IPTG at 37° C. and 150 RPM.

*Borrelia burgdorferi* strain B31 was kindly supplied by the lab of J. Hovius (Amsterdam Medical Centre). Genomic DNA of *B. burgdorferi* was extracted using the DNeasy Blood & Tissue Kit (Qiagen) according to the manufacturer's instructions.

1.3 Recombinant DNA Technology

All primers used in this study are shown in Table 1. Hybrids were made of fHbp (*N. meningitidis*), TbpB (*N. meningitidis*), OspA (*B. burgdorferi* or *B. afzelii*), OspC (*B. burgdorferi*) and RmpM (*N. meningitidis*). All hybrids were constructed using Overlap Extension PCR (53). All PCRs were carried out using the Accuprime Taq DNA Polymerase System (Invitrogen) to ensure both high fidelity amplification and the addition of 3' A-overhangs. See FIGS. 1 and 5 for a schematic overview of the different constructs.

TABLE 1

Oligonucleotide primers used in this study

| Primer number | SEQ ID NO | Primer name | Sequence (5'->3') |
|---|---|---|---|
| 1 | 9 | fHbp-F | CATATGCGCCGTTCGGACGACATTTGATTTTTGC |
| 2 | 10 | fHbp-R | GACGTCACGGTAAATTATCGTGTTCG |
| 3 | 11 | OspA-F | CATATGAAGGAGAATATATTATGAAAAAATATTTATTGG |
| 4 | 12 | OspA-R | GACGTCTAAAGCTAACGCTAAAGCAAATCC |
| 5 | 13 | M13-F | GTAAAACGACGGCCAG |
| 6 | 14 | M13-R | CAGGAAACAGCTATGAC |
| 7 | 15 | pEN11-F | AAACCGCATTCCGCACCACAAG |
| 8 | 16 | pEN11-R | GGGCGACACGGAAATGTTGAATAC |
| 9 | 17 | fA1-F | GTGTCGCCGCCGACATCGGTGCGAGCGTTTCAGTAGATTTGC |
| 10 | 18 | fA1-R | GCAAATCTACTGAAACGCTCGCACCGATGTCGGCGGCGACAC |
| 11 | 19 | fA2b-F | GGCGACCCGGGTGGCTCAGGTGCTAGCGTTTCAGTAGATTTGC |
| 12 | 20 | fA2b-R | AAACGCTAGCACCTGAGCCACCCGGGTCGCCGATTCTGAACTG |
| 13 | 21 | fA3b-F | TTAAAACCGGGTGGCTCAGGTGCTAGGGCGACATATCGCGGGACG |
| 14 | 22 | fA3b-R | CGCCCTAGCACCTGAGCCACCCGGTTTTAAAGCGTTTTTAATTTC |
| 15 | 23 | fA4b-F | AAGCAACCGGGTGGCTCAGGTGCTAGCGTTTCAGTAGATTTGC |
| 16 | 24 | fA4b-R | AAACGCTAGCACCTGAGCCACCCGGTTGCTTGGCGGCAAG |
| 17 | 25 | fA4c-F | CCTTGCCGCCAAGCAATGTAAGCAAAATGTTAGC |
| 18 | 26 | fA4c-R | GCTAACATTTTGCTTACATTGCTTGGCGGCAAGG |
| 19 | 27 | fA5c-F | GAAATTAAAAACGCTTTAAAATGCAGCAGCGGAGGGGTGGTG |
| 20 | 28 | fA5c-R | CACCACCCCCTCCGCTGCTGCATTTTAAAGCGTTTTTAATTTC |
| 21 | 29 | fA6-F | CCATAAAGACAAAGGTTTGAGCGTTTCAGTAGATTTGC |
| 22 | 30 | fA6-R | GCAAATCTACTGAAACGCTCAAACCTTTGTCTTTATGG |
| 23 | 31 | fA7-F | CAATACGGGCAAATTGAAGAGCGTTTCAGTAGATTTGC |
| 24 | 32 | fA7-R | GCAAATCTACTGAAACGCTCTTCAATTTGCCCGTATTG |
| 25 | 33 | pfHbpTbpB-F | CGTATGACTAGGAGTAAACCTATGAACAATCCATTGGTGAATCAGG |
| 26 | 34 | pfHbpTbpB-R | CCAATGGATTGTTCATAGGTTTACTCCTAGTCATACG |
| 27 | 35 | TbpB-R | GACGTCCGTCTGAAGCCTTATTCTCG |
| 28 | 36 | OspA afz-R long | GACGTCTACTTTTTGGCTCAGTACC |
| 29 | 37 | OspC-F | CATATGAATAAAAAGGAGGCACAAATTAATG |
| 30 | 38 | OspC-R | GACGTCTTAATTAAGGTTTTTTTGGACTTTCTG |
| 31 | 39 | RmpM-R | GACGTCGCATCGGCAAGATATTGC |
| 32 | 40 | fA10-F | CCATAAAGACAAAGGTTTGAGCGCTTCAGTAGATTTGC |
| 33 | 41 | fA10-R | GCAAATCTACTGAAGCGCTCAAACCTTTGTCTTTATGG |
| 34 | 42 | fTA1-F | CCTGTGTTTTGTTGAGTGCTTGTAAGCAAAATGTTAGCAGCCTTG |
| 35 | 43 | fTA1-R | CAAGGCTGCTAACATTTTGCTTACAAGCACTCAACAAAACACAGG |

TABLE 1 -continued

Oligonucleotide primers used in this study

| Primer number | SEQ ID NO | Primer name | Sequence (5'->3') |
|---|---|---|---|
| 36 | 44 | fTA2-F | GCAAGCCCAAAAAGACCAAAGCGTTTCAGTAGATTTGC |
| 37 | 45 | fTA2-R | GCAAATCTACTGAAACGCTTTGGTCTTTTTGGGCTTGC |
| 38 | 46 | fTA3-F | CAAGCGGCGGAATTGGTATCAGAGGAGCGTTTCAGTAGATTTGC |
| 39 | 47 | fTA3-R | GCAAATCTACTGAAACGCTCCTCTGATACCAATTCCGCCGCTTG |
| 40 | 48 | fTA4-F | GGATGATGGTGATATCAAAAGCGTTTCAGTAGATTTGCCTGGTG |
| 41 | 49 | fTA4-R | CACCAGGCAAATCTACTGAAACGCTTTTGATATCACCATCATCC |
| 42 | 50 | fTA5-F | GCAAGCCCAAAAAGACCAAAGCGCTTCAGTAGATTTGC |
| 43 | 51 | fTA5-R | GCAAATCTACTGAAGCGCTTTGGTCTTTTTGGGCTTGC |
| 44 | 52 | fC9-F | GACCATAAAGACAAAGGTTTGAATAAATTAAAAGAAAAACACACAG |
| 45 | 53 | fC9-R | CTGTGTGTTTTTCTTTTAATTTATTCAAACCTTTGTCTTTATGGTC |
| 46 | 54 | fR1-F | CCATAAAGACAAAGGTTTGCCGCAATATGTTGATGAAACC |
| 47 | 55 | fR1-R | GGTTTCATCAACATATTGCGGCAAACCTTTGTCTTTATGG |
| 48 | 56 | fTR1-F | GCAAGCCCAAAAAGACCAACCGCAATATGTTGATGAAACC |
| 49 | 57 | fTR1-R | GGTTTCATCAACATATTGCGGTTGGTCTTTTTGGGCTTGC |

Amplicons were ligated blunt-end in the pGEM-T Easy vector (Promega) and subsequently heat-shock transformed into *E. coli* JM109 cells (Promega) according to the manufacturer's instructions. Transformants were screened for insert of the correct length using primers M13-F and M13-R (see Table 1). Plasmids were isolated from overnight cultures of positive JM109 transformants using the Wizard Plus SV Plasmid Miniprep System (Promega). Isolated plasmids were digested using restriction enzymes AatII and NdeI (Fermentas). The resulting fragments were then separated by gel-electrophoresis, and subsequently gel-purified using the Wizard SV Gel and PCR Cleanup System (Promega). Universal plasmid pEN11 (54) was used as vector after digestion with AatII and NdeI in the presence of Shrimp Alkaline Phosphatase (Roche). Inserts and vector were ligated using T4 DNA ligase (Promega) according to the manufacturer's instruction and the resulting plasmids were then heat-shock transformed into *E. coli* One Shot TOP10F' competent cells (Invitrogen). Transformants were screened for insert of the correct length using primer pEN11-F and a reverse primer of the respective construct. Approximately 1 μg of isolated pEN11 plasmid (isolation procedure as described before) carrying OspA or fHbp-OspA fusions was added to a 1 ml suspension of *N. meningitidis* cells ($OD_{600}$≈0.2) and grown in TSB supplemented with 10 mM $MgCl_2$ at 37° C. for 6 hours (no shaking). Bacteria were then plated on GC plates containing 3 μg/ml Cam. Colonies were isolated after 24-48 hours and screened for the presence of pEN11 with correct insert as before.

1.4 Expression of Constructs in *N. meningitidis* Cells and nOMVs

*N. meningitidis* cells were streaked out on GC II plates (Becton Dickinson) and grown overnight as described. The following day, colonies were harvested with a sterile cotton swab were suspended in TSB containing 1 mM IPTG and 3 μg/ml Cam and further diluted to an $OD_{600}$ of 0.2 in 5 ml of the same broth with supplements. Cells were grown for 4 hours at 37° C. and 170 RPM after which $OD_{600}$ was again determined and aliquots corresponding to $4.0 \times 10^8$ CFU were centrifuged for 5 min at 13,000 RPM and resuspended in phosphate buffered saline (PBS). Cells were then centrifuged as before, after which the resulting pellet was dissolved in 40 μl MQ, combined with 10 μl 5× sample buffer (50% glycerol, 0.25% Tris pH 6.8, 10% Sodium Dodecyl Sulphate, 10% dithiothreitol and 0.05% Bromophenol blue), and boiled for 10 minutes. Samples were then stored at −20° C. for further analysis.

*N. meningitidis* native OMVs (nOMVs) were diluted to 20 μg total protein per ml in PBS, after which 40 μl nOMV suspension was boiled with 10 μl 5× sample buffer as before.

Protein samples of cells of nOMVs were separated by SDS-PAGE on 12% Precise Protein Gels (Thermo Scientific). Separated proteins were then transferred to 0.45 μm nitrocellulose membranes (BioRad). Membranes were incubated for 1 hour on a rolling table in a 1:1000 dilution of anti-OspA (Rockland) in buffer containing 0.1 M Tris, 1.54 M NaCl, and 5% Tween-80. The membrane was then transferred to a 1:2000 dilution of goat-anti-rabbit IgG AP (Southern BioTech) in the same buffer supplemented with 0.5% Protifar (Nutricia). Blots were developed using the AP Conjugate Substrate Kit (BioRad).

1.5 Immunostaining

*N. meningitidis* cells carrying pEN11 with the various constructs were immobilized on coverslips coated with poly-1-lysine (Sigma). Cells were fixated with 2% formaldehyde in PBS for 10 minutes. After blocking in PBS containing 3% Bovine Serum Albumin (BSA, Sigma), the coverslips were first incubated in a 1:300 dilution of a mix of anti-OspA (Rockland) and anti-fHbp (variant 1, NIBSC) in PBS with 0.5% BSA. After washing, they were incubated in a 1:300 dilution of a mix of Alexa Fluor 488 goat-anti-rabbit IgG and Alexa Fluor 594 goat-anti-mouse IgG (Life Technologies). Slides were post-fixed in 2% formaldehyde in PBS and viewed under an Olympus CKX41 fluorescence microscope at 40× magnification using appropriate filters.

1.6 Purification of nOMV Vaccines

Glycerol-stocks of clones selected for the immunization experiment were streaked out on GC II plates and grown overnight under conditions described above. The following day, colonies were harvested and used to start a 200 ml culture of $OD_{600}$=0.05 in TSB with 1 M IPTG and 3 µg/ml Cam. These cultures were grown at 37° C. and 130 RPM and $OD_{600}$ was measured at regular intervals. When cultures reached an $OD_{600}$ of 1.5 (after ~6 hours) they were placed on ice and subsequently centrifuged at 3,500 RPM and 4° C. for 30 minutes. Pellets were resuspended in a Tris-EDTA buffer (100 mM Tris, 10 mM EDTA, pH=8.6) and incubated on a horizontal shaking table for 30 minutes. Since this buffer contains a chelating agent (EDTA) that destabilizes the OM, the release of OMVs is stimulated. The suspensions were centrifuged at 13,000 RPM for 30 minutes and the supernatant was sterilized using a Steriflip 0.22 µm filter (Millipore). The sterile supernatant was then centrifuged at 40,000 RPM for 65 minutes, after which the resulting OMV pellet was allowed to dry before being resuspended in 1 ml sucrose buffer. Suspensions were again filtered as before and stored at 4° C.

The nOMV isolation procedure described above was developed in order to harvest as many nOMVs as possible without the hitchhiking of other cellular proteins due to lysis. As we noticed that the expression of OspA, fA1, fA2b, fA3b, and fA5c in nOMVs harvested using this procedure could be increased by allowing the respective cultures to grow for 12 hours, without significantly increasing the hitchhiking of other bacterial proteins (data not shown), we therefore decided to use the alternative isolation procedure for these constructs, in order to equalize the expression of constructs as much as possible.

The total protein concentration of the isolated nOMVs was measured using the BCA Protein Assay Kit (Pierce) and nOMVs were then further diluted in PBS to 5 or 20 µg total protein per ml on the day of vaccination.

1.7 Mice and Immunization

Groups of five female, six- to eight-week-old BALB/cOlaHsd mice (Harlan) were immunized subcutaneously with 200 µl of nOMVs, at either low concentration (5 µg/ml) or high concentration (20 µg/ml). Next to the groups that received nOMVs 'loaded' with OspA (two groups) or fHbp-OspA fusions (sixteen groups), two control groups received 'empty' nOMVS harvested form cells carrying the pEN11 plasmid with the imp gene replacing the ospA-constructs (54). An additional control group was immunized with PBS, resulting in a total of 21 groups. Mice were immunized at days 0 and 28 and sacrificed 14 days after the last immunization. Blood was collected in Vacuette Z Serum Clot Activator tubes (Greiner Bio-One) and centrifuged at 2000 RPM for 15 minutes. Subsequently, sera were collected and stored at −20° C. for further analysis.

1.8 Analysis of Sera

Sera were first pooled by group (five mice) and analyzed for the presence of antibodies by Western blot. Membranes were loaded with proteins from *E. coli* TOP10F' cells carrying either pEN11-Imp or pEN11-OspA. Membranes were incubated for one hour on a rolling table with pooled sera diluted 1:1000 in Tris buffer (described previously), followed by incubation in a 1:2000 dilution of secondary antibody (goat-anti-mouse IgG AP, Southern BioTech) in the same buffer and blot development as described previously. The ten individual sera of all mice from the two most strongly reacting groups (fA4b, 20 µg/ml and fA6, 20 µg/ml) were analyzed in the same manner.

For ELISAs, 100 µl of 0.5 µg/ml OspA control protein (Rockland) diluted in PBS was coated on the surface of wells in Microlon 96-well plates (GreinerBio) and incubated overnight at room temperature (RT). The following day, plates were blocked by adding 200 µl 0.5% Protifar in PBS followed by incubation for 30 minutes at RT. Plates were then washed three times in wash buffer (water with 0.05% tween-80). Sera of individual mice were suitably diluted in PBS with 0.1% tween-80 and 100 µl was added per well, followed by incubated for 1 hour at RT. Plates were then again washed three times in wash buffer, after which 100 µl of goat-anti-mouse IgG HRP (SouthernBiotech) was added (diluted 1:4000 in PBS with 0.1% tween-80). After incubation for 1 hour, the plates were washed as before and 100 µl of TMB was added. Plates were then incubated for 10 minutes after which coloring was stopped with 100 µl 2 M $H_2SO_4$. $OD_{450}$ was subsequently measured on a SynergyMx plate-reader (Biotek).

2. Results

2.1 Construction of fHbp-OspA Fusion-Genes

Adjacent to their lipidated N-terminal cysteine, most characterized lipoproteins contain a stretch of amino acids with a low propensity for the formation of secondary structure. This so-called 'tether' is thought to act as a flexible linker between the lipid 'anchor' (the lipidated cysteine) and the structurally confined part of the protein (55). Tethers also play a role in the transport of lipoproteins over the outer membrane, since deletions in this region can result in mislocalization of surface-exposed lipoproteins to the inside of the outer membrane (55).

Since we found no evidence for the surface exposure of OspA expressed in *Neisseria*, we hypothesized that the switch of bacterial host resulted in mislocalization of the protein to the inside of the outer membrane. We then set out to test whether the addition of parts of fHbp, a surface-exposed *Neisserial* lipoprotein, might correct this mislocalization. Since the sorting rules for transport over the outer membrane in *Neisseria* have not yet been elucidated, we designed hybrid genes that combined various parts of fHbp with the globular domain of OspA.

Figure 1B:
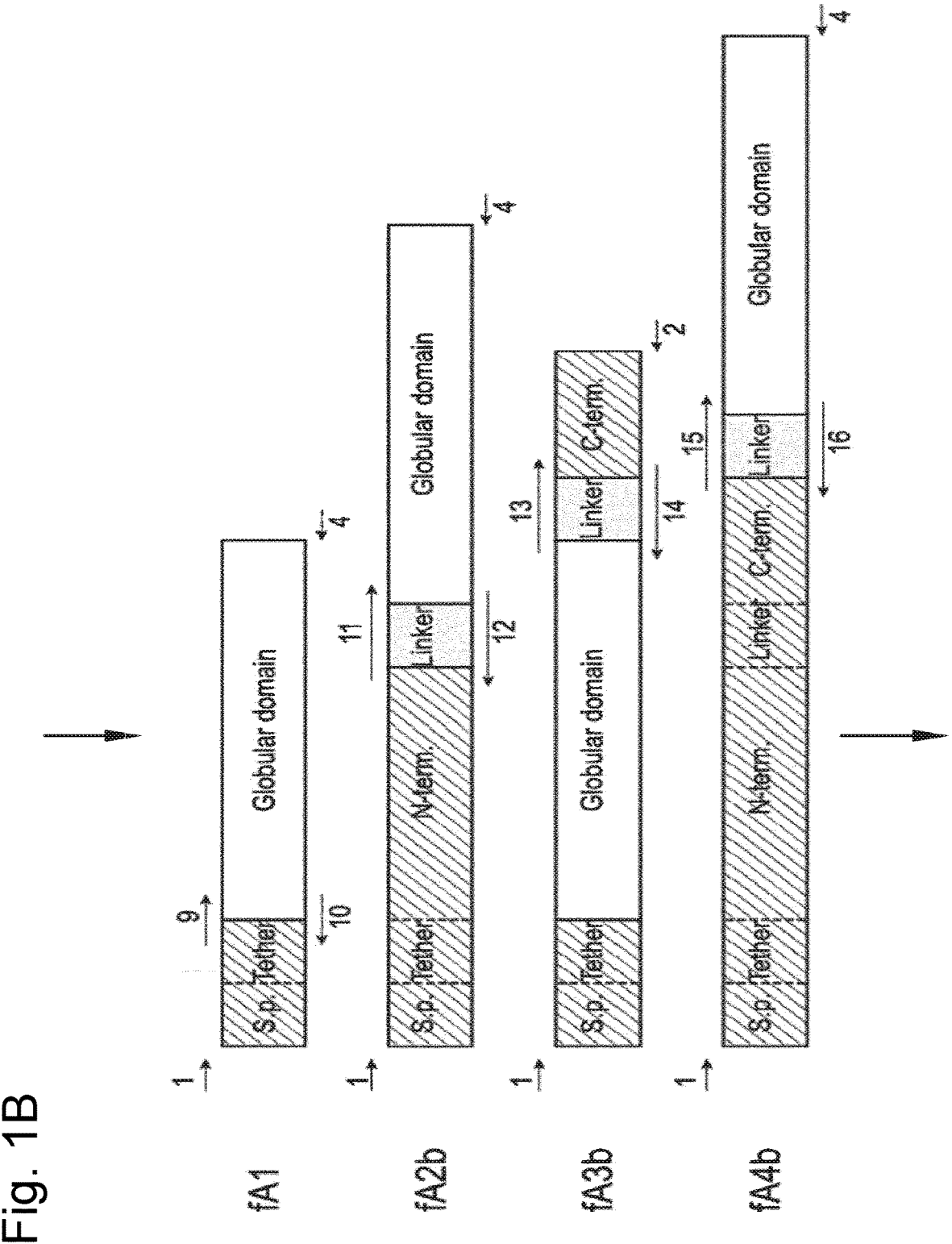
Figure 1C:
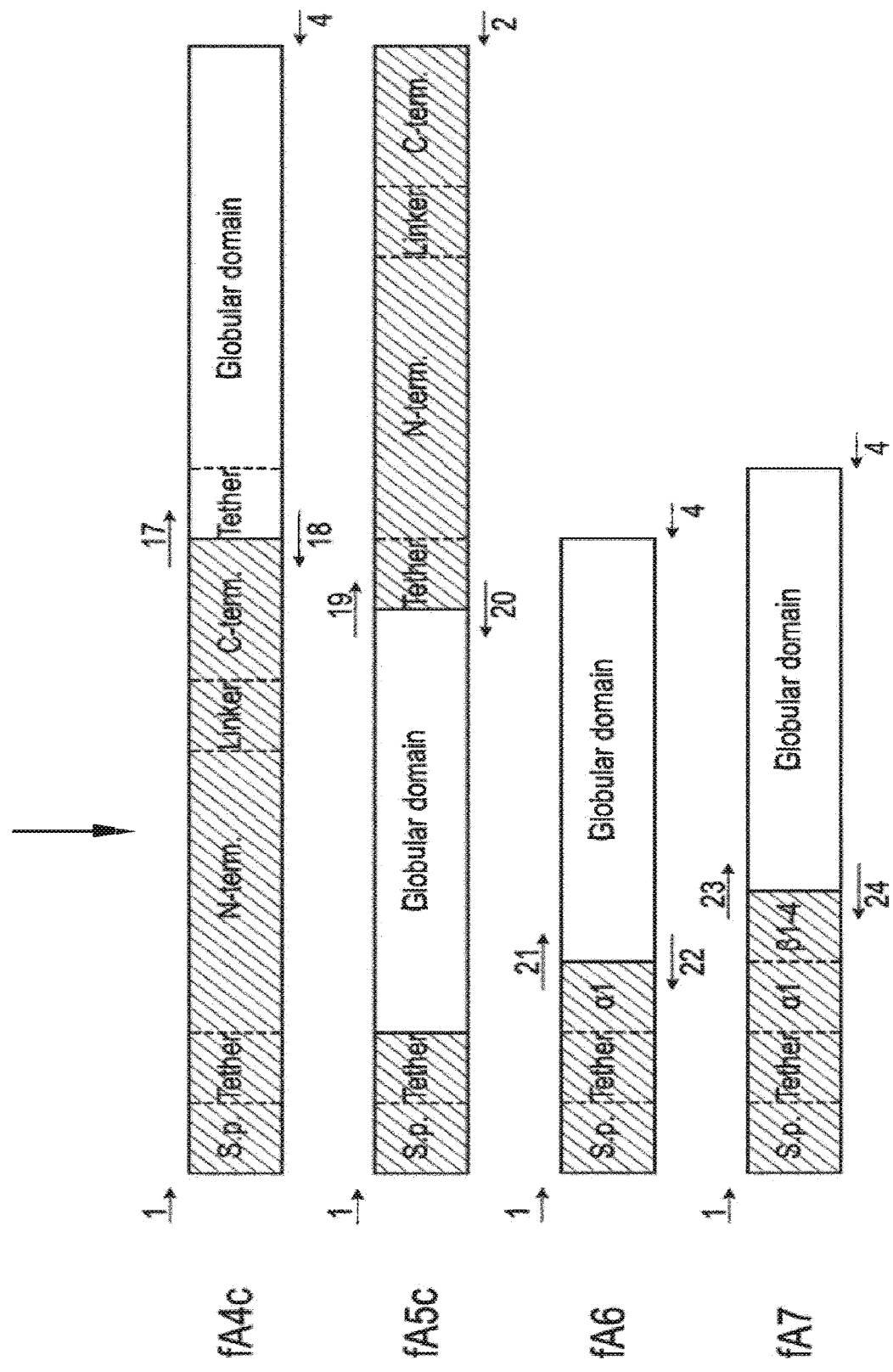

A schematic overview of fHbp and OspA, as well as the fusion genes created from these two genes by overlap extension PCR, is given in FIG. 1. Information regarding the structure of both lipoproteins was obtained from published crystal structures (48, 56). Both fHbp and OspA contain a signal peptide (that is cleaved after transport over the inner membrane) and a tether region. The globular domain of fHbp consists of an N-terminal and a C-terminal domain that are separated by a 15 amino acid linker.

Genomic DNA of N. meningitidis strain 44/76 was used as template in all PCR reactions involving the amplification of parts of fHbp. The fHbp-F primer anneals upstream of the fHbp promoter (57), and therefore all fusion-genes contain the fHbp promoter. OspA was amplified from genomic DNA of B. burgdorferi strain B31 using primers OspA-F and OspA-R (Table 1), and was successfully expressed in E. coli TOP10F' from the pEN11 plasmid, which contains an IPTG-inducible tac-lacUV5 promoter (54).

The six amino acid linker peptide that was introduced in constructs fA2b, fA3b, and fA4b was previously used to successfully link OspA to calmodulin (58).

We created eight different fusion constructs between fHbp and OspA. From here on we refer to these constructs as 'fA'. Primers used for the construction of fusion genes are shown above (forward primers) or below (reverse primers) the schematic genes in FIG. 1 (primer numbers refer to Table 1). All fusion genes were created by overlap extension PCR, a two-step PCR protocol (53). In short, the gene parts to be fused were first amplified separately using partially overlapping primers, after which both parts (that can anneal to each other) were used as template in a second reaction yielding the fusion gene. As an example, the first step PCRs for construct fA1 used primer pairs 1-10 (to amplify the fHbp promoter, signal peptide, and tether from the N. meningitidis genome) and 4-9 (to amplify the globular domain of OspA from the B. burgdorferi genome). The resulting PCR products were then mixed and used as template in a second PCR reaction. In this second reaction, both PCR products anneal to each other and at the same time serve as template for primer pair 1-4 resulting in the full-length PCR product fA1. All other fusion genes were created using the same method. Note that construct fA1 served as template for the construction of fA3b and fA5c.

In fA1, the signal peptide and tether of fHbp were fused to the globular domain of OspA. In constructs fA2b and fA3b, the C-terminal domain (fA2b) or N-terminal domain (fA3b) of fHbp was replaced by the globular domain of OspA and connected via an artificial linker (PGGSGA). In constructs fA4b and fA4c, the complete fHbp gene was linked to the globular domain of OspA using the artificial linker (fA4b) or the OspA tether (fA4c). Construct fA5c is fA1 linked to the globular domain of fHbp via the fHbp tether. Constructs fA6 is similar to fA1, but in addition to signal peptide and tether also contains the first alpha-helix and subsequent loop of the N-terminal domain of fHbp. Construct fA7 is similar to fA6, but additionally contains the first four beta-sheets of the N-terminal domain of fHbp. All constructs were successfully expressed from pEN11 in E. coli TOP10F' before transformation in Neisseria (data not shown).

2.2 Construction of TbpB-OspA Fusion Genes

TbpB of N. meningitidis H44/76 contains a signal peptide (residues 1-20), a 38 amino acid flexible linker or 'tether' (residues 21-58), and a large globular domain (residues 59-691). In order to test whether fusion of N-terminal parts of TbpB to OspA could rescue surface expression of OspA in N. meningitidis, four TbpB-OspA fusion constructs were designed. Because TbpB has an iron-regulated promoter, the TbpB promoter was first exchanged for the constitutive fHbp promoter using overlap extension PCR with primers 1, 25-27 (see Table 1). The resulting construct ('TbpB with fHbp promoter', see FIG. 5) was then used as template for fusion PCRs between TbpB and OspA.

An overview of constructs fTA1-4 can be found in FIG. 5, while primers for the overlap-extension PCRs can be found in Table 1. Genomic DNA from Neisseria meningitidis H44/76 was used as template for amplification of parts of TbpB and genomic DNA of Borrelia burgdorferi strain B31 was used as template for the OspA part.

Construct fTA1 contained residues 1-20 (the signal peptide) of TbpB fused to residues 17-273 (tether and globular domain) of OspA. Construct fTA2 contained residues 1-58 (signal peptide and tether) of TbpB fused to residues 29-273 (globular domain) of OspA. Construct fTA3 contained residues 1-75 (signal peptide, tether and first seventeen N-terminal amino acids of the globular domain) of TbpB fused to residues 29-273 (globular domain) of OspA. Construct fTA4 contained residues 1-99 (signal peptide, tether and first 41 N-terminal amino acids of the globular domain) of TbpB fused to residues 29-273 (globular domain) of OspA. TbpB fusion points for fTA3 and fTA4 were chosen in loops between secondary structure elements, based on the TbpB crystal structure (63).

Figure 7B:
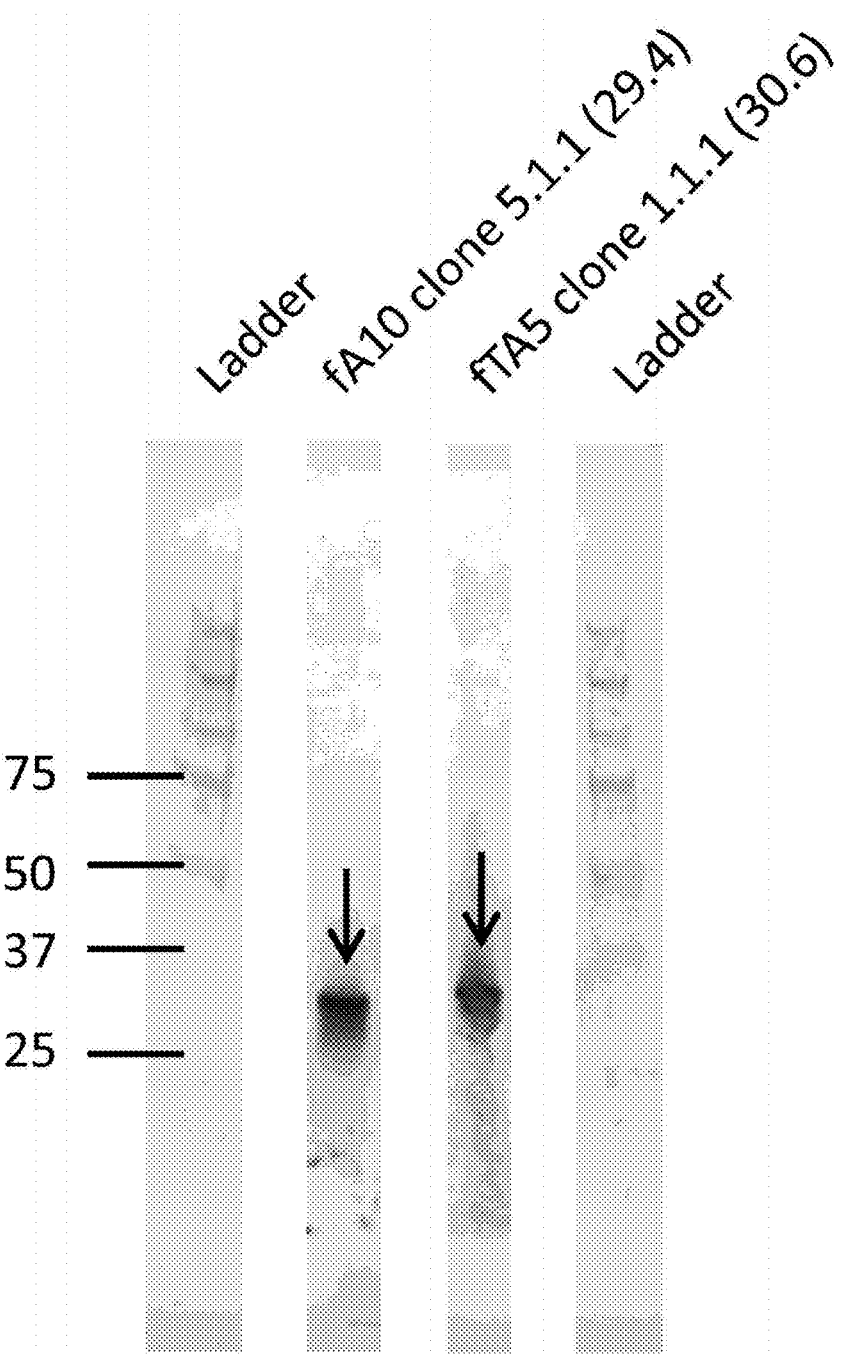
FIG. 7. Schematic overview and western blot analysis of fHbp-OspA and TbpB-OspA fusion constructs. A) Schematic overview of the constructs. fHbp fragments are hatched, OspA fragments are grey and TbpB fragments are white. Amino acid numbering for fHbp, TbpB and OspA is shown in boxed areas. S.p.=signal peptide. Numbered arrows refer to primers listed in Table 1, forward primers are shown above and reverse primers are shown below the schematic (fusion) genes, positioning of the arrow heads reflects the approximate positioning of the 3'end. B) Western blot analysis of OspA expression in *N. meningitidis* cells carrying constructs fA10 and fTA5 using OspA monoclonal antibody (Santa Cruz Biotechnologies). Expected molecular mass of the different constructs is shown in kDa (in parentheses). Arrows indicate full-length proteins.

To test whether OspA serotypes other than serotype 1 (B. burgdorferi B31) could be transported to the meningococcal cell surface with the help of N-terminal parts of fHbp or TbpB, fusion constructs similar to fA6 and fTA2 were made, the only difference being that they contained the globular domain of OspA serotype 2 from Borrelia afzelii PKo (residues 29-273). All constructs were made by overlap extension PCR, see FIG. 7 and Table 1 for details.

2.3 Construction of fHbp—OspC Fusion Genes

OspC is a surface-exposed borrelial lipoprotein. It is generally considered to be the most interesting vaccinogen after OspA (64). However, the expression of full-length OspC including its signal sequence has proven difficult in E. coli (65), possibly due to its tendency to aggregate; in the Borrelia outer membrane, it is present in the form of large multimeric complexes. Expression of full-length OspC in both E. coli and N. meningitidis previously led to similar problems in our hands, resulting in poor expression on Western blots (data not shown).

Figure 8A:
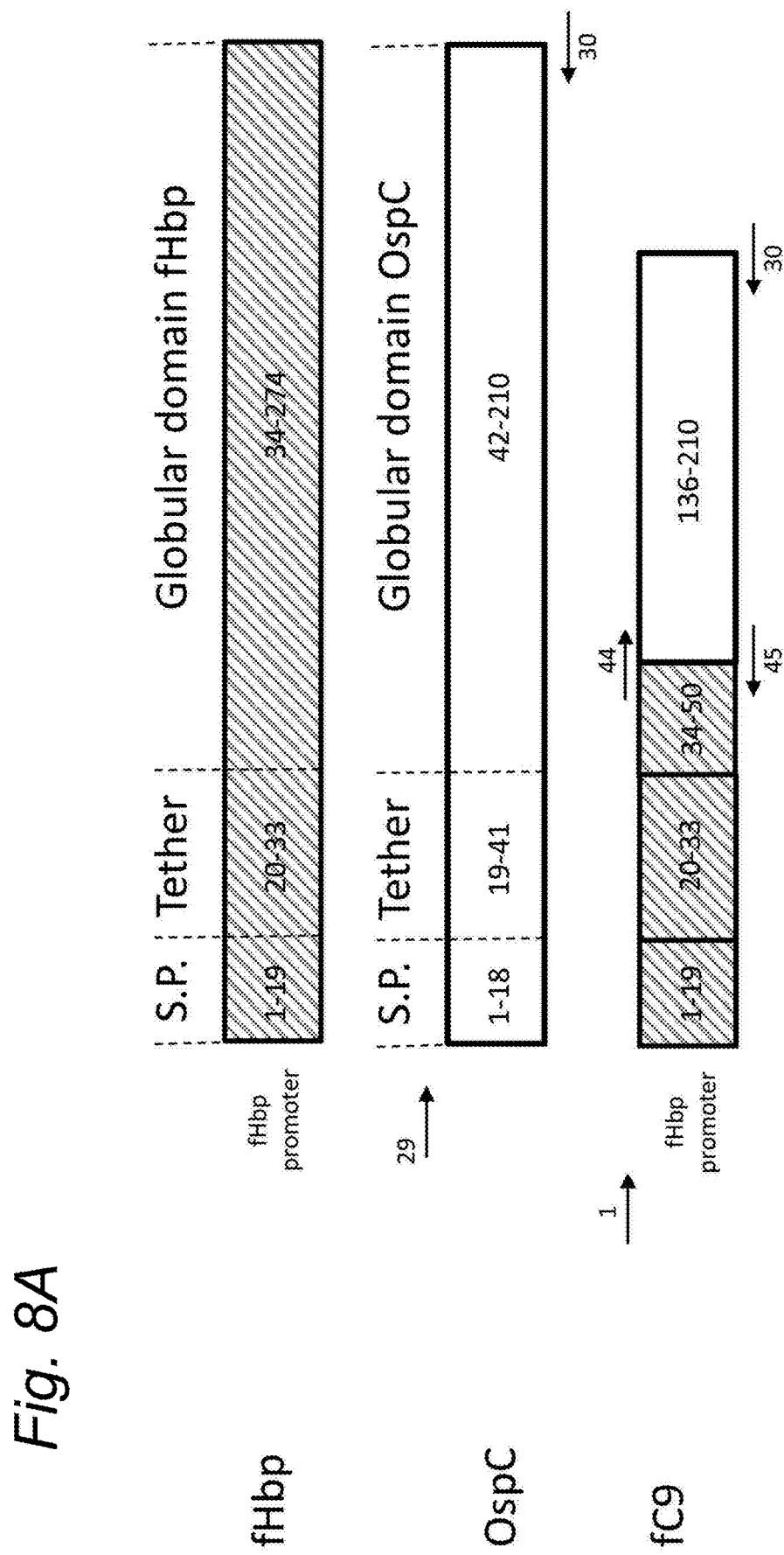
FIG. 8. Schematic overview and western blot analysis of fHbp-OspC fusion constructs. A) Schematic overview of the constructs. fHbp fragments are hatched and OspC fragments are white. Amino acid numbering for fHbp and OspC is shown in boxed areas. S.p.=signal peptide. Numbered arrows refer to primers listed in Table 1, forward primers are shown above and reverse primers are shown below the schematic (fusion) genes, positioning of the arrow heads reflects the approximate positioning of the 3' end. B) Western blot analysis of OspC expression in *N. meningitidis* cells with constructs fC9 and OspC. No clear expression for OspC was observed. Expected molecular mass of the different constructs is shown in kDa (in parentheses). The construct fC9 does not form homodimers.
Figure 8B:
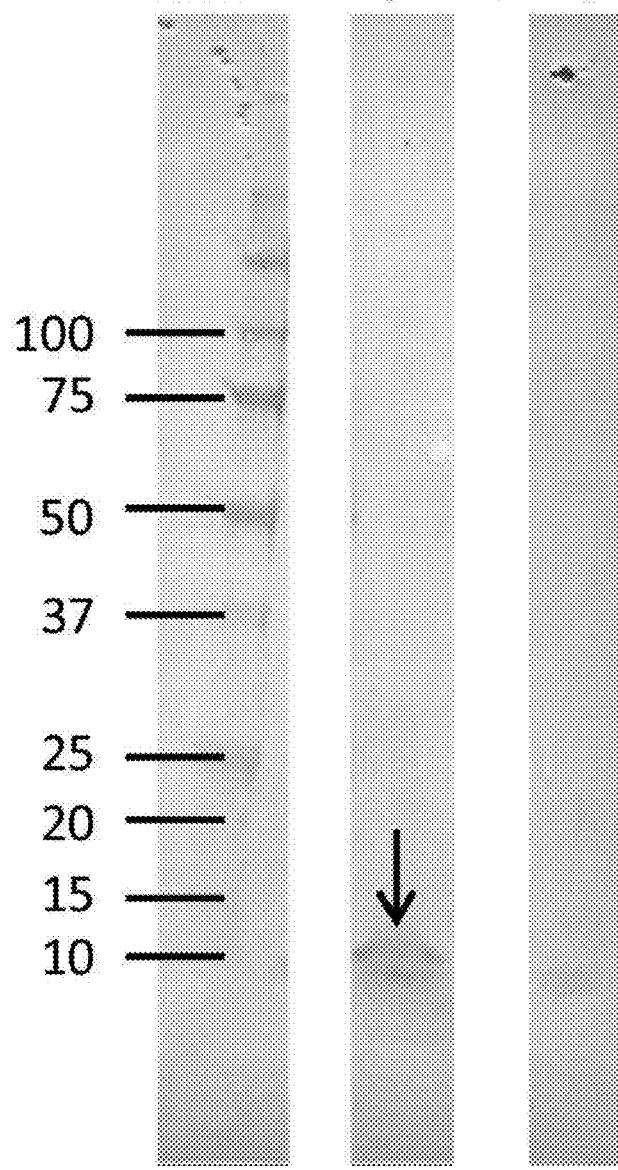
Figure 9B:
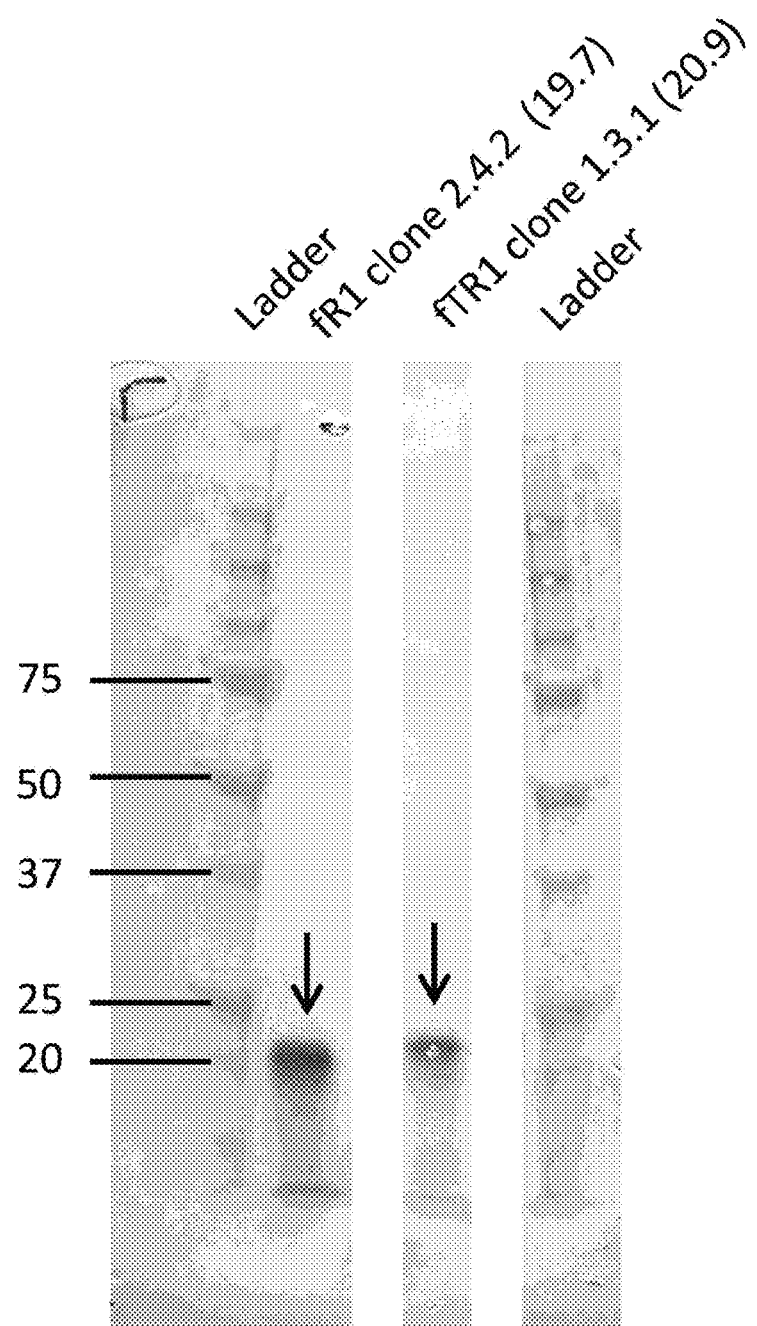
FIG. 9. Schematic overview and western blot analysis of the fHbp-RmpM and TbpB-RmpM fusion constructs. A) Schematic overview of the constructs. fHbp fragments are hatched, RmpM fragments are grey and TbpB fragments are white. Amino acid numbering for fHbp, TbpB and RmpM is shown in boxed areas. S.p.=signal peptide. Numbered arrows refer to primers listed in Table 1, forward primers are shown above and reverse primers are shown below the schematic (fusion) genes, positioning of the arrow heads reflects the approximate positioning of the 3'end. B) Western blot analysis of RmpM expression in *N. meningitidis* ΔRmpM cells with constructs fR1 and fTR1. Expected molecular mass of the different constructs is shown in kDa (in parentheses). Arrows indicate full-length proteins.

In Borrelia, OspC forms homo-dimers on the cell-surface, mostly by interactions between the N-terminal al-helices (66, 67). Since most murine and human OspC epitopes are located on the C-terminal side of the protein (68, 69), fusion construct fC9 (FIG. 8) was generated, that combined the previously described N-terminal part of fHbp (as used in fA6) and C-terminal residues 136-210 of OspC (see FIG. 8). To this end, genomic DNA of N. meningitidis strain H44/76 was used as template for the amplification of fHbp and genomic DNA of B. burgdorferi strain B31 was used for amplification of OspC 2.4 Construction of fHbp-RmpM and TbpB-RmpM Fusion Genes RmpM is an outer membrane protein of N. meningitidis that is thought to associate non-covalently with the peptidoglycan layer (70). It consists of a signal peptide, a flexible N-terminal domain (which binds to integral outer membrane proteins), and an OmpA-like C-terminal domain (which is thought to associate with peptidoglycan). Since RmpM is generally considered to be mostly periplasmic, an attempt was made to express RmpM at the cell surface of *N. meningitidis*. It was decided to leave out the first 89 residues that consist of signal peptide and the unstructured N-terminal domain. The remaining C-terminal domain (residues 90-242) was fused to N-terminal parts of fHbp (residues 1-50) and TbpB (residues 1-58) that had been used previously for the successful surface localization of OspA. Genomic DNA of *N. meningitidis* strain H44/76 was used as template for the amplification of fHbp, TbpB, and RmpM. The constructs were named fR1 and fTR1 (see FIG. 9).

Figure 2A:
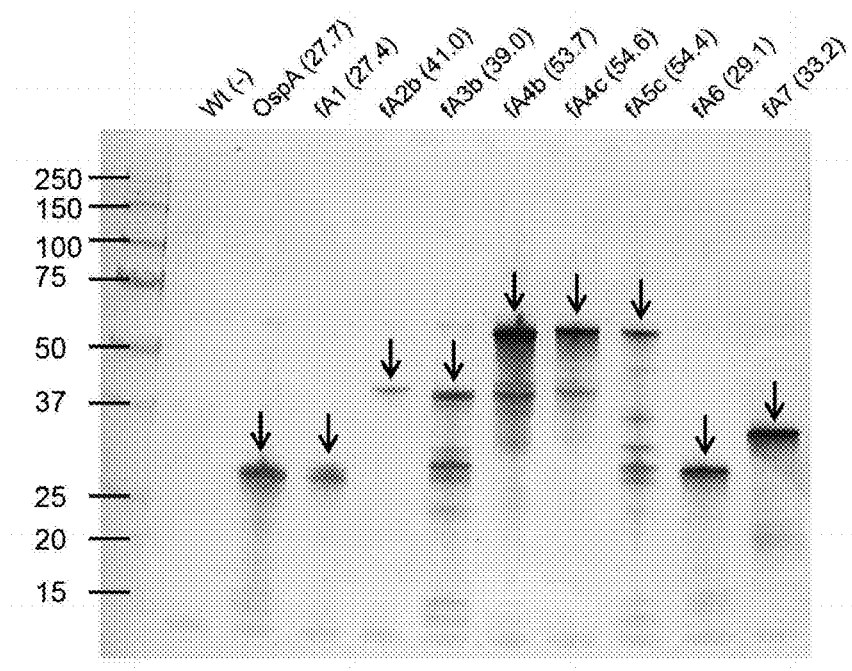
FIG. 2. Western blot analysis of OspA expression in *N. meningitidis* cells (A) or nOMVs (B) carrying OspA or fusion constructs. Cells and nOMVs were normalized based on $OD_{600}$ and protein content, respectively. Expected molecular mass of the different constructs is shown in kDa (in parentheses). Arrows indicate the full-length proteins. Wt: *N. meningitidis* cells (or nOMVs harvested from these cells) carrying 'empty' plasmid pEN11-Imp (see Materials and Methods).
Figure 2B:
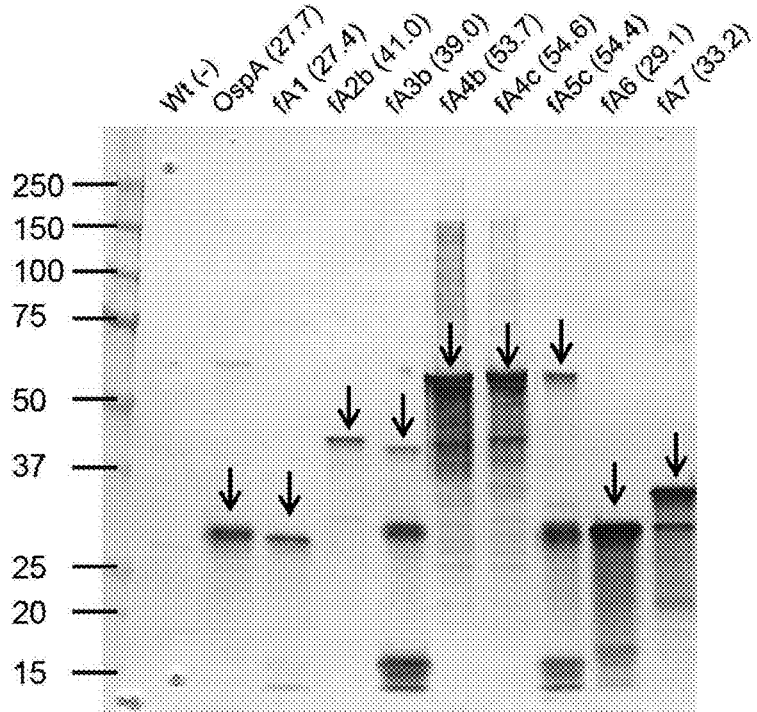

2.5 OspA and fHbp-OspA Fusions are Expressed in *N. meningitidis* Cells and nOMVs The expression of the different constructs in *N. meningitidis* is shown in FIG. 2A and expression in nOMVs harvested from these cells is shown in FIG. 2B. Expression levels in *N. meningitidis* cells clearly vary between the different constructs and similar variation is observed in the nOMVs, with high expression levels for constructs fA4b, fA4c, fA6, and fA7. Several constructs are apparently prone to degradation. For some constructs (fA3b, fA5c), degradation seems to be amplified in nOMVs compared to cells.

2.6 at Least Four fHbp-OspA Hybrids are Surface Exposed

We tested whether or not OspA and the eight fHbp-OspA fusions were surface-localized in *N. meningitidis* using immunostaining. Briefly, cells containing plasmid pEN11 with the various constructs were incubated with a mix of anti-OspA and anti-fHbp (positive control), followed by incubation with fluorescent secondary antibodies (green for OspA and red for fHbp). Cells containing constructs fA4b, fA4c, fA6, and fA7 showed clear green fluorescence, indicating surface exposure of these constructs (data not shown). No green fluorescence was observed for OspA or any of the other constructs (data not shown), indicating that they were not surface exposed, although we cannot rule out the possibility that this is due to their lower expression level (see FIG. 2A).

2.7 Expression and Surface-Exposure TbpB-OspA Hybrids

Successful expression of all four constructs in *E. coli* and *N. meningitidis* was confirmed by Western blot using a polyclonal antiserum against OspA (Rockland Immunochemicals—see FIG. 6 for *Neisseria* Western blots). Immunostaining (as described above) showed no signal for construct fTA1, but a strong signal for constructs fTA2, fTA3, and fTA4 (data not shown). This proves that N-terminal parts of TbpB can be used for the surface localization of OspA and that at least signal peptide and tether are required for this.

2.8 Expression and Surface-Exposure of Alternative C-Protein Fusion Partners

2.8.1 Expression and Surface Exposure of an Alternative OspA Serotype

Successful expression of both constructs in *E. coli* and *N. meningitidis* was confirmed by Western blot using a polyclonal antiserum against OspA (Rockland Immunochemicals—see FIG. 7 for *Neisseria* Western blots). Immunostaining with the OspA polyclonal (Rockland Immunochemicals) proved difficult, most probably because the antiserum (which was raised against serotype 1 OspA from *B. burgdorferi*) showed considerably weaker binding to the *B. afzelii* OspA. Therefore, an OspA monoclonal antibody (Santa Cruz Biotechnology) was used for immunostaining. *N. meningitidis* cells expressing constructs fA10 and fTA5 showed a strong signal when this monoclonal was used for immunostaining (data not shown), indicating that the serotype 2 OspA was indeed successfully expressed at the cell surface.

2.8.2 Expression and Surface Exposure of OspC

Despite poor expression in *N. meningitidis* (FIG. 8), cells carrying the fC9 construct surprisingly showed a signal with immunostaining (data not shown). This indicates that the N-terminal part of fHbp (as previously described in fA6) can be used for the surface localization of at least C-terminal parts of OspC.

2.8.3 Expression and Surface Exposure of the Non-Borrelial Non-Lipoprotein RmpM Both constructs (named fR1 and fTR1, see FIG. 11), were successfully expressed in *E. coli* and *N. meningitidis*.

Although immunostaining yielded bright signals for both constructs, the negative control (*N. meningitidis* cells without construct) showed bright fluorescence as well. This indicated either a-specific binding of the MN2D6D monoclonal antibody to *Neisseria* cells, or unanticipated surface localization of (parts of) RmpM. Therefore, a RmpM knockout was created using plasmid pCF13 (71). Plasmids carrying constructs fR1 and fTR1 were transformed in this ΔRmpM strain as before and successful expression of both constructs was determined by Western blot (see FIG. 12).

Immunostaining of *N. meningitidis* cells and the RmpM knockout showed that there was a-specific binding of the RmpM antibody at high antibody concentrations (strong staining of the knockout at 1:300 dilution and weak staining of the knockout at 1:2000 dilution, data not shown), while at low antibody concentrations (1:10,000) staining of the knockout completely vanished (data not shown). However, some normal *Neisseria* cells still showed staining at this low concentration (data not shown), indicating that at least for part of the cells RmpM might be (partially) surface exposed.

When placed in the RmpM knockout background, both fR1 and fTR1 showed a fluorescent signal at the lowest antibody concentration (1:10,000), while staining was completely absent for the RmpM knockout without construct at this concentration (data not shown). This indicates that the N-terminal parts of both fHbp and TbpB that were previously used for the surface localization of OspA can also be used for the surface localization of an otherwise (predominantly) periplasmic non-lipoprotein of *Neisseria meningitidis*.

2.9 Immunogenicity of nOMVs Carrying OspA and fHbp-OspA Hybrids

Next, we investigated the sera of mice immunized with nOMVs carrying heterologous (fusion) proteins using Western blot. Pooled sera of all 21 groups were blotted on membranes loaded with total protein content of *E. coli* with either pEN11-OspA or pEN11-Imp (see FIG. 3A for some of these groups). Pooled sera of the groups immunized with nOMVs carrying both low and high doses of constructs fA4b, fA4c, fA6, and fA7 all showed a strong band with the molecular mass of OspA (~28 kDa), indicating a strong antibody response. Additionally, the pooled sera of the group immunized with the 20 µg/ml dose of OspA-carrying nOMVS showed a very weak band at ~28 kDa (data not shown). All other groups showed no detectable response.

Figure 3A:
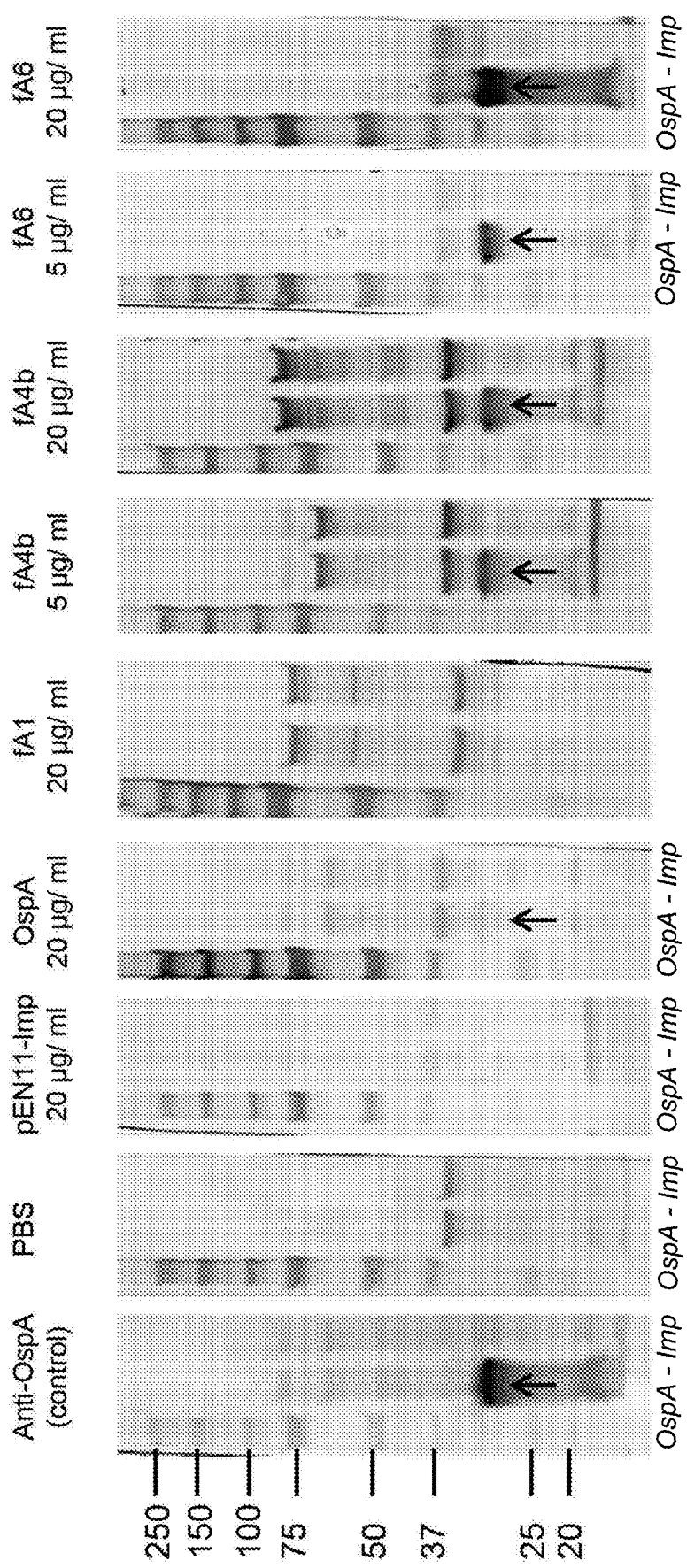
FIG. 3. Western blot analysis of mouse sera. Lanes were loaded with *E. coli* carrying pEN11-OspA ('OspA') or pEN11-Imp ('Imp'). (A) From left to right; (1) control blot with anti-OspA showing the expected band of ~28 kDa and blots with pooled sera of groups of five mice immunized with (2) PBS, (3) high dose empty nOMVS, (4) high dose OspA nOMVs, (5) high dose fA1 nOMVs, (6) low and (7) high dose fA4b nOMVs, and (8) low and (9) high dose of fA6 nOMVS. (B) Blots with sera from individual mice immunized with a high dose of fA6 nOMVs (pooled sera of this group are at the far right in FIG. 4A). Arrows point at bands with a molecular weight similar to that of OspA (~28 kDa).
Figure 3B:
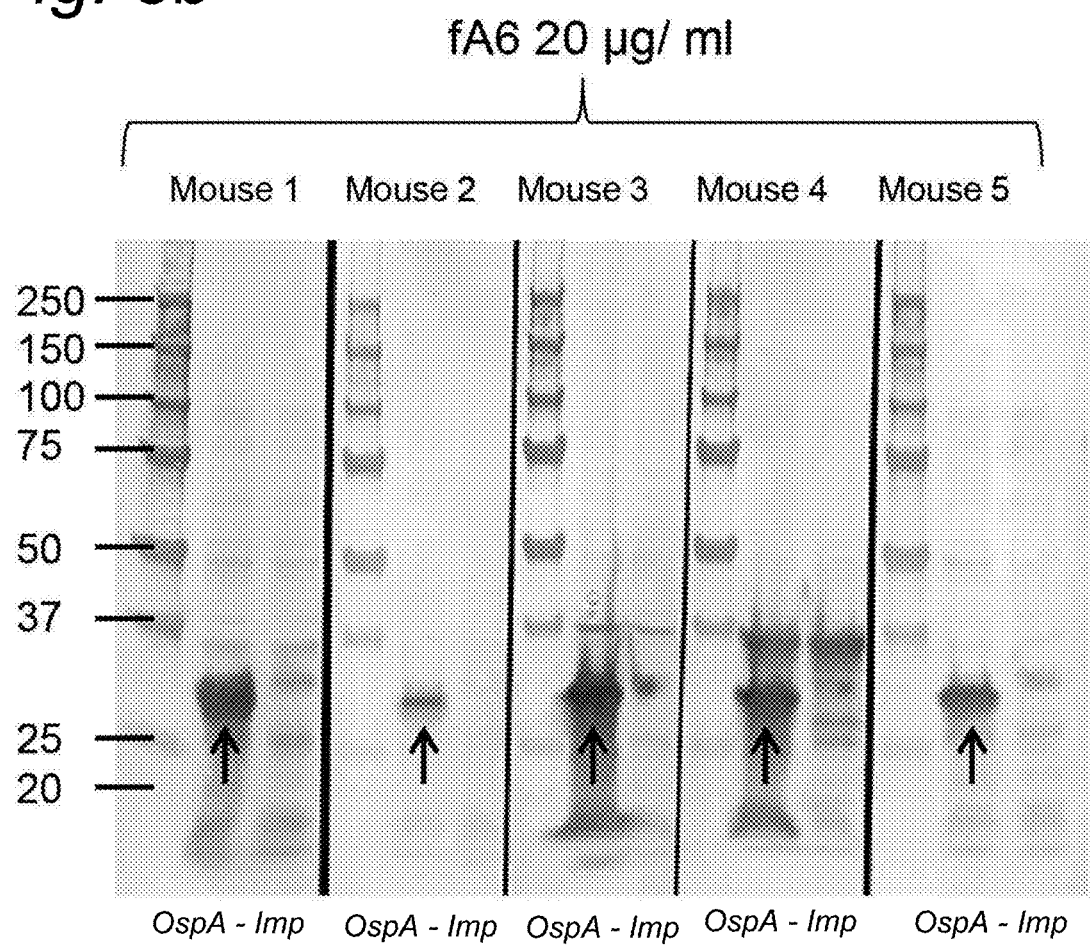

To see whether all individual mice raised OspA-specific antibodies, we blotted the sera of all ten individual mice from two highly responsive groups (20 µg/ml fA4b and 20 µg/ml fA6). In all cases a ~28 kDa band was detected (see FIG. 3B for the five mice immunized with 20 µg/ml fA6, data for fA4b not shown). This shows that the observed signals in the pooled sera were not due to single hyper-responders in the groups. Note that the ~36 kDa background signal in the pooled sera of the high dose fA6 group (FIG. 3A) is clearly caused by a single individual (mouse #4 in FIG. 4B).

Figure 4A:
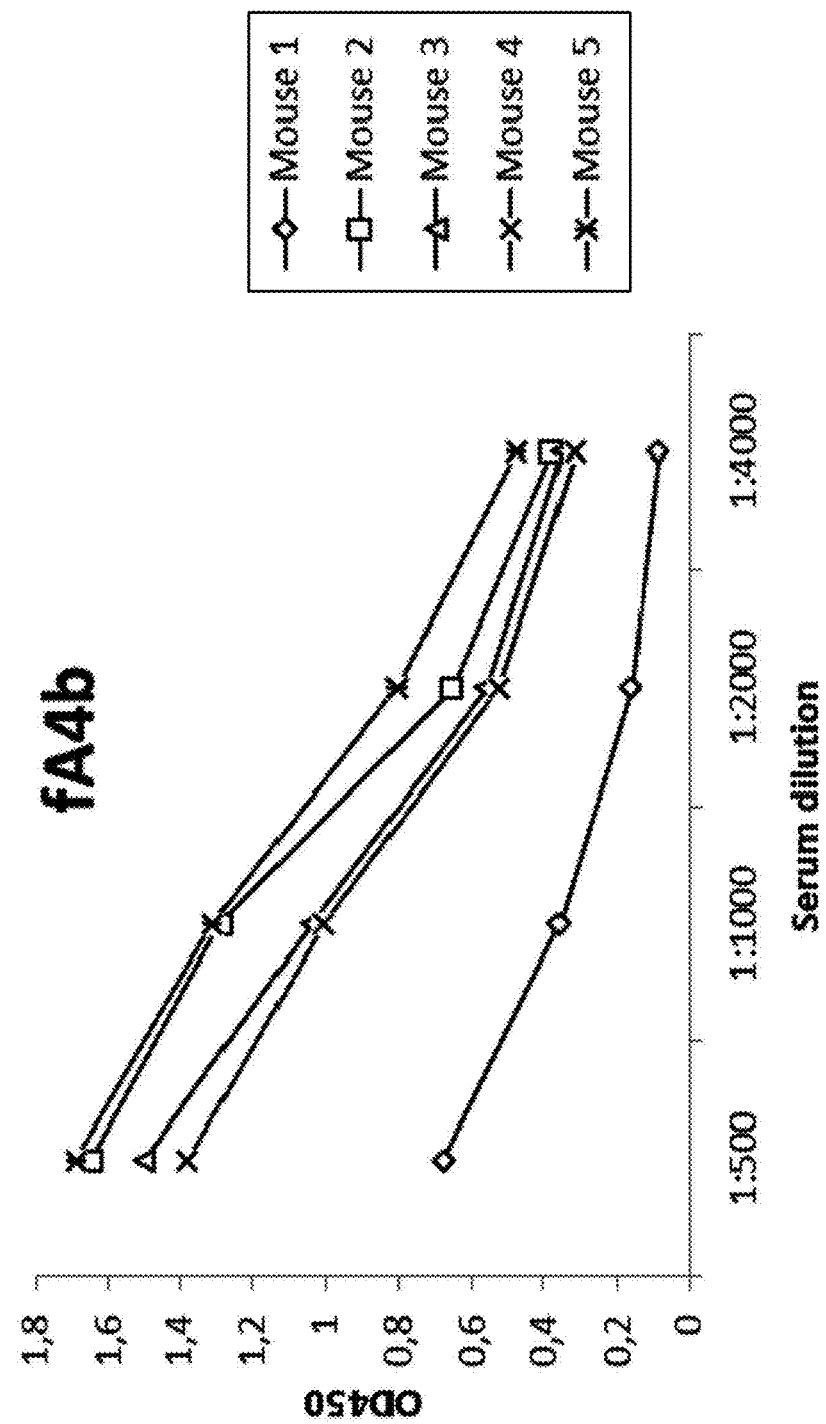
FIG. 4. ELISA data for sera from individual mice immunized with 20 µg/ml nOMVs carrying construct fA4b, fA4c, fA6, or fA7. Pooled sera of mice immunized with 20 µg/ml nOMVs carrying empty vector pEN11-Imp were used as negative control and subtracted from data before plotting. Note that sera of mice immunized with fA6 tested here are the same as the ones in the Western blot shown in FIG. 4b, which is reflected in the lower responsiveness of individual #2.
Figure 4B:
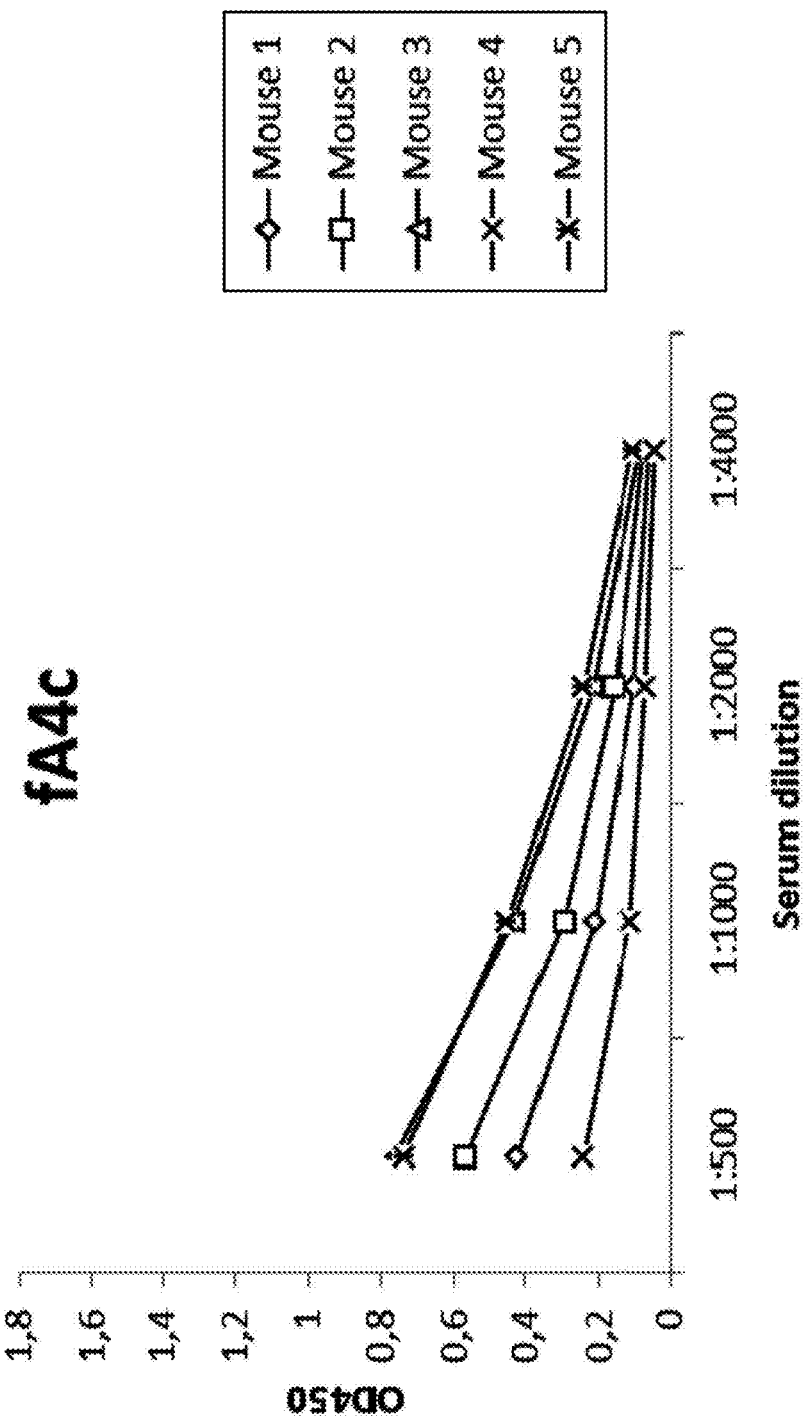
Figure 4D:
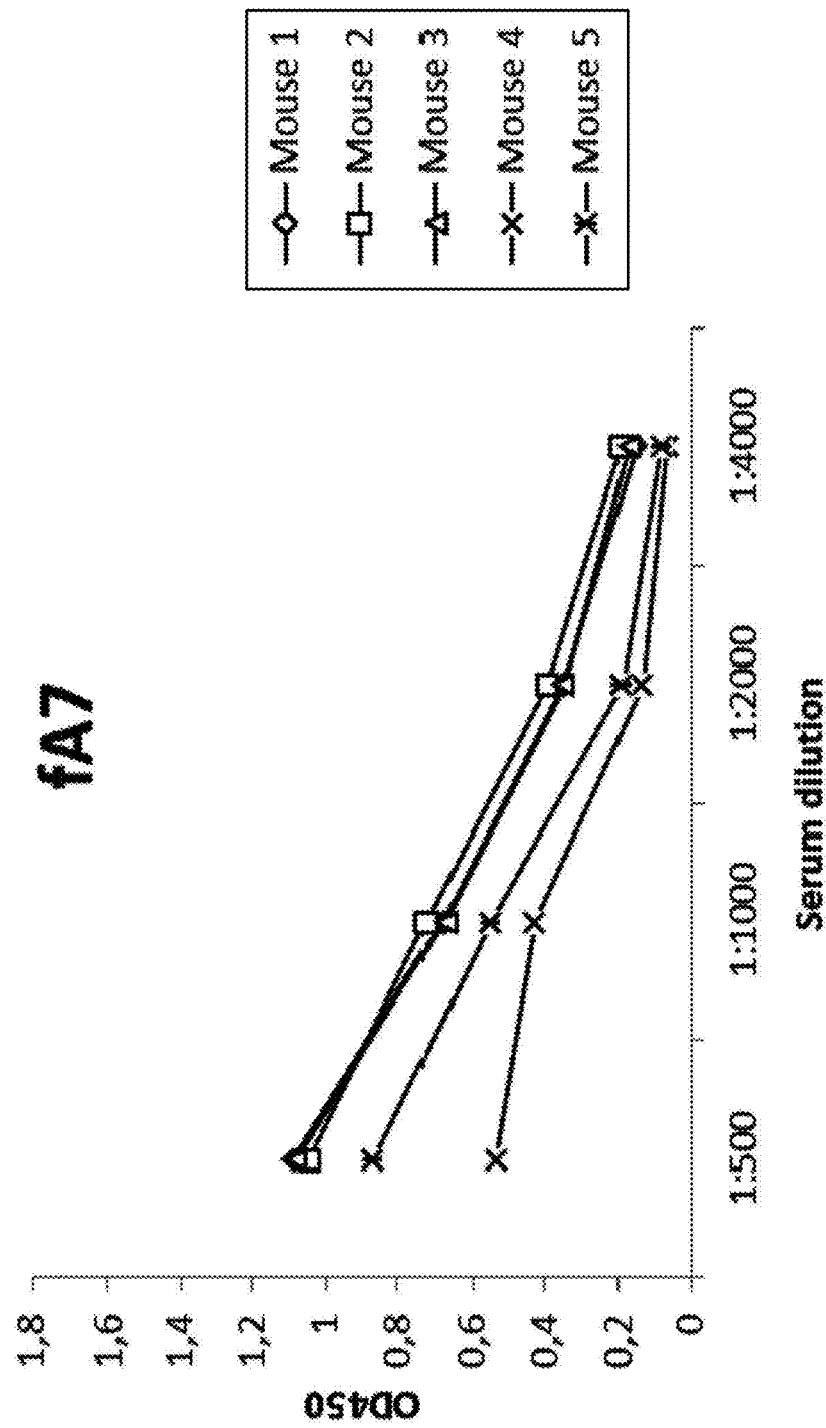
Figure 6:
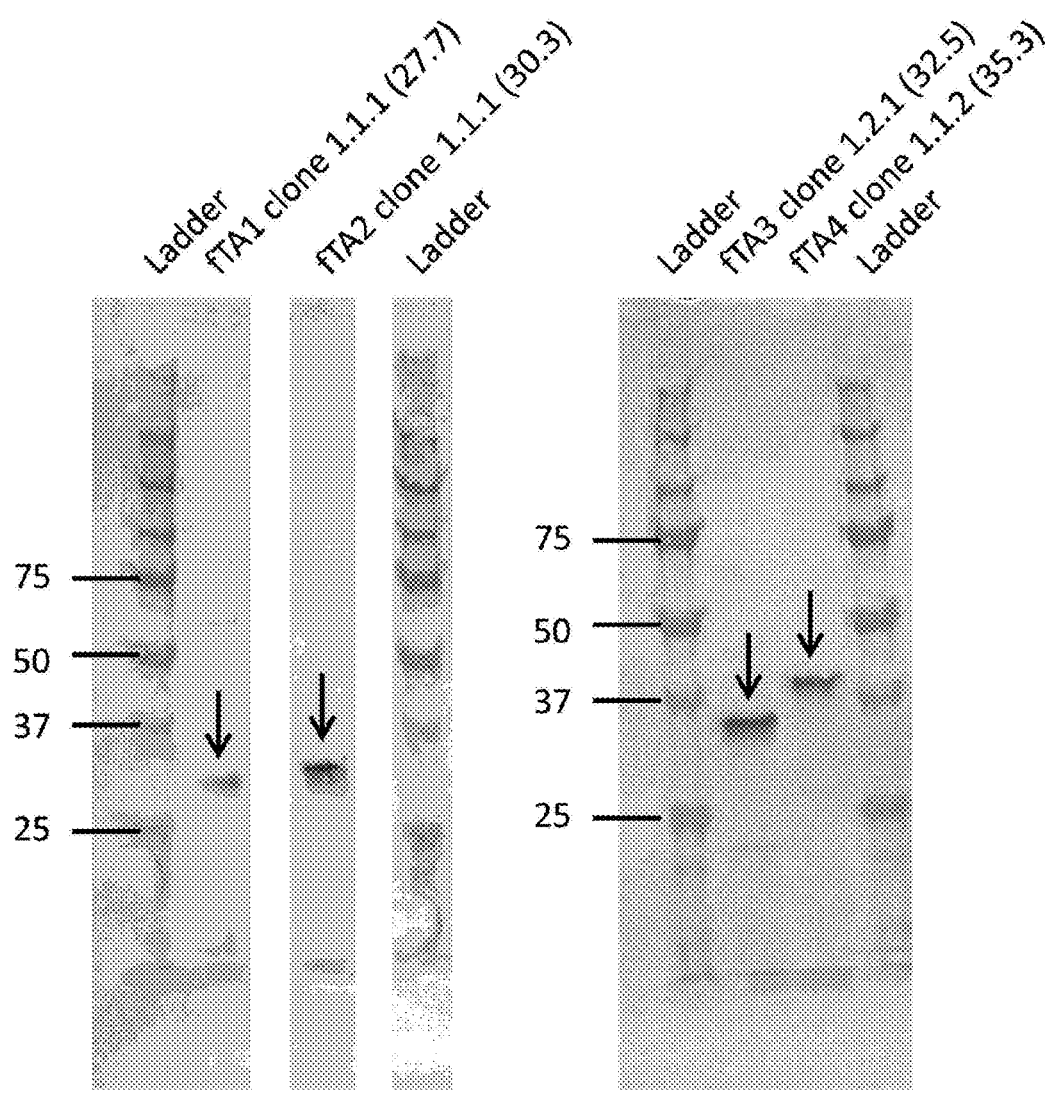
FIG. 6. Western blot analysis of OspA expression in *N. meningitidis* cells carrying constructs fTA1-4 using OspA polyclonal (Rockland Immunochemicals). Expected molecular mass of the different constructs is shown in kDa (in parentheses). Arrows indicate full-length proteins.

In order quantify the immune response, sera of all individual mice immunized with 20 µg/ml nOMVs carrying constructs fA4b, fA4c, fA6, or fA7 were tested for their binding capacity to purified OspA protein. Results for constructs fA4b and fA6 are shown in FIG. 4. The signal detected for fA4b was ~1.5 times higher than that observed for fA6 and fA7 and ~2.5 times higher than that observed for fA4c (data not shown).

3. Discussion

OMVs are gaining attention as a robust and engineerable vaccine platform against many bacterial diseases. With the recognition of their vaccine potential, interest in heterologous expression in OMVs has flourished. One of the unresolved issues regarding heterologous expression in OMVs is whether the location of the heterologous antigen (lumen, inside of OM, outside of OM) affects the immune response that it evokes. For whole cells, some studies indicate that heterologous antigens are more immunogenic when they are located on the cell surface than when they reside beneath it (59, 60), and it has been suggested that the same may be true for OMVs (21). This makes the display of heterologous proteins on the OMV surface of special interest.

Here, we demonstrate a novel approach for the surface display of heterologous antigens in OMVs. A detergent-free OMV extraction process was recently developed for *Neisseria* that allows surface-exposed lipoproteins to remain attached to the OMV. This new extraction protocol opens up the possibility to decorate the surface of *Neisseria* OMVs with heterologous lipoproteins. We therefore expressed OspA, a Borrelial surface lipoprotein, in *N. meningitidis*. Although OspA could be detected in *Neisseria* cells and OMVs, we found no evidence for its surface exposure. We then constructed fusions between OspA and fHbp, a meningococcal surface lipoprotein. Several of these constructs consisting of N-terminal parts of fHbp linked to OspA could be detected at the cell surface using immunostaining. Furthermore, we have demonstrated that technology is more broadly applicable as lipoprotein mediated surface expression could also be mediated by N-terminal parts of other lipoproteins, such as TbpB. In addition we demonstrated that a variety of antigenic proteins, including non-borrelial non-lipoproteins such as RmpM, could be surface expressed by fusion to N-terminal parts of lipoproteins. Hence, we have shown that the technology is broadly applicable to mediate the surface expression of specific antigens. The antigens may be associated with an infectious disease and/or a tumour. The fusion proteins of the invention cause surface expression of such antigens on e.g. OMVs, which triggers an immune response, resulting in the prevention or treatment of an infectious disease or tumour associated with the antigen.

In this respect, OMVs carrying these constructs elicited a strong immune response in immunized mice, while OMVs carrying constructs that showed no evidence of surface exposure did not.

3.1 Outer Membrane Translocation

Knowledge of factors that govern the translocation of lipoproteins over the OM is frugal and incomplete. In *Borrelia*, the lipoprotein tether (the unstructured region adjacent to the N-terminal cysteine) of several surface lipoproteins (OspA, OspC, and Vsp) seems to contain essential information for OM translocation, since deletion or mutation of amino acids in this region can lead to subsurface localization. Furthermore, fusion of the signal peptide and tether of these three lipoproteins to red fluorescent protein leads to surface localization of this otherwise periplasmic reporter-protein in *Borrelia* (47, 51, 55).

*Neisseria* has only a few surface lipoproteins and what factors affect their translocation over the OM is unknown. Our data indicate that, at least for fHbp, these factors are different from those found in *Borrelia*.

In our hands, expression of OspA in *N. meningitidis* leads to mislocalization in the periplasm or periplasmic side of the outer membrane. This is in line with previous findings that expression of a lipoprotein in an alternative host can lead to mislocalization, probably because host factors define the localization rules (51). We reasoned that hybridization with an autologous surface exposed lipoprotein from *Neisseria* like fHbp or TbpB might rescue this mislocalization and therefore constructed fusions between OspA and different parts of fHbp or TbpB. Replacement of the OspA signal peptide and tether with that of fHbp (construct fA1) did not restore OspA surface localization. However, when the fHbp part of this fusion gene was extended with the first 17 N-terminal amino acids of the globular domain of fHbp (consisting of the first alpha-helix and subsequent loop), the resulting construct (fA6) could be detected at the cell surface. This indicates that sorting rules may differ between *Neisseria* and *Borrelia*, since in the former the region affecting outer membrane translocation seems to extend beyond the tether region.

Almost all constructs that consists of fusion of OspA to an N-terminal part of fHbp longer than that in fA6 were detected at the cell surface (fA4b, fA4c, fA7). The only exception is construct fA2b, which contains amino acids 1-152 of fHbp (the so-called N-terminal domain) coupled to OspA via an artificial linker. It is however important to stress that considering the extremely poor expression level of fA2b in cells (see FIG. 2A), it is not possible to discriminate whether the lack of signal after immunostaining resulted from subsurface localization or poor expression. We discuss this localization-expression problem further below. Constructs in which OspA was placed in between N-terminal and C-terminal parts of fHbp (fA3b, fA5c) were not detected at the cell surface.

3.2 Effect of Antigen Location on Immunogenicity

We found evidence for surface exposure of constructs fA4b, fA4c, fA6, and fA7 in *Neisseria* cells. Coinciding with this, OMVs carrying these constructs were the only ones to elicit strong antibody responses in immunized mice.

This suggests that only antigens that are located on the surface of the OMV can elicit antibody responses. However, it is important to realize that the expression level of the four 'surface' constructs is clearly higher than that of the other constructs, both in cells and nOMVs (see FIG. 2). Failure to detect a specific construct after immunostaining could therefore also result from low expression levels rather than subsurface localization. It is not possible to exclude this scenario for constructs that have a very low expression levels in cells, e.g. fA1 and fA2b. However, cells that express OspA, fA3b, or fA5c have considerably higher expression levels, and it seems unlikely that we would not observe them after immunostaining in case they were surface exposed.

If we compare the Western blots of the groups of mice immunized with high dose OspA and low dose fA6 carrying OMVs (FIG. 2A, blots 4 and 5 from left), the difference in apparent immunogenicity is much higher than we would expect based on the observed expression levels of these constructs in OMVs (FIG. 2B). This indicates that surface display of a heterologous antigen in the OMV can indeed lead to enhanced immunogenicity.

3.3 Vaccine Potential

Borrelia vaccines that are currently in development are subunit vaccines that are based on various recombinant lipidated OspA serotypes (38, 39). However, subunit vaccines suffer from poor immunogenicity and require the use of adjuvants. The presentation of OspA on the surface of Neisserial nOMVs may result in better immunogenicity because of the intrinsic adjuvant activity of the nOMV and the presentation of the antigen in its native conformation.

Our OMV surface display method is generally applicable to other antigenic proteins from pathogens, including also non-lipoproteins, especially since it has been shown that lipidation of non-lipoproteins via fusion to lipoproteins can enhance immunogenicity (62). Furthermore it is possible to combine the expression and OMV surface display of multiple heterologous antigens in order to facilitate the production of multivalent heterologous OMVs.

REFERENCES

1. Ellis T N, Kuehn M J. Virulence and immunomodulatory roles of bacterial outer membrane vesicles. Microbiology and molecular biology reviews: MMBR. 2010; 74(1): 81-94.
2. Chen D J, Osterrieder N, Metzger S M, Buckles E, Doody A M, DeLisa M P, et al. Delivery of foreign antigens by engineered outer membrane vesicle vaccines. Proceedings of the National Academy of Sciences of the United States of America. 2010; 107(7): 3099-104.
3. Muralinath M, Kuehn M J, Roland K L, Curtiss R, 3rd. Immunization with Salmonella enterica serovar Typhimurium-derived outer membrane vesicles delivering the pneumococcal protein PspA confers protection against challenge with Streptococcus pneumoniae. Infection and immunity. 2011; 79(2): 887-94.
4. Alaniz R C, Deatherage B L, Lara J C, Cookson B T. Membrane vesicles are immunogenic facsimiles of Salmonella typhimurium that potently activate dendritic cells, prime B and T cell responses, and stimulate protective immunity in vivo. J Immunol. 2007; 179(11): 7692-701.
5. Gaillard M E, Bottero, D., Errea, A. Acellular pertussis vaccine based on outer membrane vesicles capable of conferring both long-lasting immunity and protection against different strain genotypes. Vaccine. 2014; 32: 931-7.
6. Zollinger W D, Donets M A, Schmiel D H, Pinto V B, Labrie J E, 3rd, Moran E E, et al. Design and evaluation in mice of a broadly protective meningococcal group B native outer membrane vesicle vaccine. Vaccine. 2010; 28(31): 5057-67.
7. Nieves W, Petersen H, Judy B M, Blumentritt C A, Russell-Lodrigue K, Roy C J, et al. A Burkholderia pseudomallei outer membrane vesicle vaccine provides protection against lethal sepsis. Clinical and vaccine immunology: CVI. 2014; 21(5): 747-54.
8. Camacho A I, de Souza J, Sanchez-Gomez S, Pardo-Ros M, Irache J M, Gamazo C. Mucosal immunization with Shigella flexneri outer membrane vesicles induced protection in mice. Vaccine. 2011; 29(46): 8222-9.
9. Kim O Y, Hong B S, Park K S, Yoon Y J, Choi S J, Lee W H, et al. Immunization with Escherichia coli outer membrane vesicles protects bacteria-induced lethality via Th1 and Th17 cell responses. J Immunol. 2013; 190(8): 4092-102.
10. Keenan J I, Rijpkema S G, Durrani Z, Roake J A. Differences in immunogenicity and protection in mice and guinea pigs following intranasal immunization with Helicobacter pylori outer membrane antigens. FEMS immunology and medical microbiology. 2003; 36(3): 199-205.
11. Roberts R, Moreno G, Bottero D, Gaillard M E, Fingermann M, Graieb A, et al. Outer membrane vesicles as acellular vaccine against pertussis. Vaccine. 2008; 26(36): 4639-46.
12. Bartolini E, Ianni E, Frigimelica E, Petracca R, Galli G, Berlanda Scorza F, et al. Recombinant outer membrane vesicles carrying Chlamydia muridarum HtrA induce antibodies that neutralize chlamydial infection in vitro. Journal of extracellular vesicles. 2013; 2.
13. Hoist J, Martin D, Arnold R, Huergo C C, Oster P, O'Hallahan J, et al. Properties and clinical performance of vaccines containing outer membrane vesicles from Neisseria meningitidis. Vaccine. 2009; 27 Suppl 2: B3-12.
14. Nokleby H, Aavitsland P, O'Hallahan J, Feiring B, Tilman S, Oster P. Safety review: two outer membrane vesicle (OMV) vaccines against systemic Neisseria meningitidis serogroup B disease. Vaccine. 2007; 25(16): 3080-4.
15. Acevedo R, Fernandez S, Zayas C, Acosta A, Sarmiento M E, Ferro V A, et al. Bacterial Outer Membrane Vesicles and Vaccine Applications. Frontiers in immunology. 2014; 5: 121.
16. Kesty N C, Kuehn M J. Incorporation of heterologous outer membrane and periplasmic proteins into Escherichia coli outer membrane vesicles. The Journal of biological chemistry. 2004; 279(3): 2069-76.
17. Fantappie L, de Santis M, Chiarot E, Carboni F, Bensi G, Jousson O, et al. Antibody-mediated immunity induced by engineered Escherichia coli OMVs carrying heterologous antigens in their lumen. Journal of extracellular vesicles. 2014; 3.
18. Schild S, Nelson E J, Bishop A L, Camilli A. Characterization of Vibrio cholerae outer membrane vesicles as a candidate vaccine for cholera. Infection and immunity. 2009; 77(1): 472-84.
19. Kim J Y, Doody A M, Chen D J, Cremona G H, Shuler M L, Putnam D, et al. Engineered bacterial outer membrane vesicles with enhanced functionality. Journal of molecular biology. 2008; 380(1): 51-66.
20. Barat S, Willer Y, Rizos K, Claudi B, Maze A, Schemmer A K, et al. Immunity to intracellular Salmonella depends on surface-associated antigens. PLoS pathogens. 2012; 8(10): e1002966.

21. Daleke-Schermerhorn M H, Felix T, Soprova Z, Ten Hagen-Jongman C M, Vikstrom D, Majlessi L, et al. Decoration of outer membrane vesicles with multiple antigens by using an autotransporter approach. Applied and environmental microbiology. 2014; 80(18): 5854-65.

22. Galen J E, Curtiss R, 3rd. The delicate balance in genetically engineering live vaccines. Vaccine. 2014; 32(35): 4376-85.

23. Hess J, Gentschev I, Miko D, Welzel M, Ladel C, Goebel W, et al. Superior efficacy of secreted over somatic antigen display in recombinant *Salmonella* vaccine induced protection against listeriosis. Proceedings of the National Academy of Sciences of the United States of America. 1996; 93(4): 1458-63.

24. Kang H Y, Curtiss R, 3rd. Immune responses dependent on antigen location in recombinant attenuated *Salmonella typhimurium* vaccines following oral immunization. FEMS immunology and medical microbiology. 2003; 37(2-3): 99-104.

25. Cornelis P. Expressing genes in different *Escherichia coli* compartments. Current opinion in biotechnology. 2000; 11(5): 450-4.

26. Georgiou G, Stathopoulos C, Daugherty P S, Nayak A R, Iverson B L, Curtiss R, 3rd. Display of heterologous proteins on the surface of microorganisms: from the screening of combinatorial libraries to live recombinant vaccines. Nature biotechnology. 1997; 15(1): 29-34.

27. van Bloois E, Winter R T, Kolmar H, Fraaije M W. Decorating microbes: surface display of proteins on *Escherichia coli*. Trends in biotechnology. 2011; 29(2): 79-86.

28. Lee S Y, Choi J H, Xu Z. Microbial cell-surface display. Trends in biotechnology. 2003; 21(1): 45-52.

29. Samuelson P, Gunneriusson E, Nygren P A, Stahl S. Display of proteins on bacteria. Journal of biotechnology. 2002; 96(2): 129-54.

30. Jong W, Daleke-Schermerhorn M H, Vikstrom D, Ten Hagen-Jongman C M, de Punder K, van der Wel N N, et al. An autotransporter display platform for the development of multivalent recombinant bacterial vector vaccines. Microbial cell factories. 2014; 13(1): 162.

31. Park M, Sun Q, Liu F, DeLisa M P, Chen W. Positional assembly of enzymes on bacterial outer membrane vesicles for cascade reactions. PloS one. 2014; 9(5): e97103.

32. Schroeder J, Aebischer T. Recombinant outer membrane vesicles to augment antigen-specific live vaccine responses. Vaccine. 2009; 27(48): 6748-54.

33. Jong W S, Sauri A, Luirink J. Extracellular production of recombinant proteins using bacterial autotransporters. Current opinion in biotechnology. 2010; 21(5): 646-52.

34. Jose J, Meyer T F. The autodisplay story, from discovery to biotechnical and biomedical applications. Microbiology and molecular biology reviews: MMBR. 2007; 71(4): 600-19.

35. Jung H C, Lebeault J M, Pan J G. Surface display of *Zymomonas mobilis* levansucrase by using the ice-nucleation protein of *Pseudomonas syringae*. Nature biotechnology. 1998; 16(6): 576-80.

36. Sigal L H, Zahradnik J M, Lavin P, Patella S J, Bryant G, Haselby R, et al. A vaccine consisting of recombinant *Borrelia burgdorferi* outer-surface protein A to prevent Lyme disease. Recombinant Outer-Surface Protein A Lyme Disease Vaccine Study Consortium. The New England journal of medicine. 1998; 339(4): 216-22.

37. Steere A C, Sikand V K, Meurice F, Parenti D L, Fikrig E, Schoen R T, et al. Vaccination against Lyme disease with recombinant *Borrelia burgdorferi* outer-surface lipoprotein A with adjuvant. Lyme Disease Vaccine Study Group. The New England journal of medicine. 1998; 339(4): 209-15.

38. Wressnigg N, Barrett P N, Pollabauer E M, O'Rourke M, Portsmouth D, Schwendinger M G, et al. A Novel Multivalent OspA Vaccine against Lyme Borreliosis Is Safe and Immunogenic in an Adult Population Previously Infected with *Borrelia burgdorferi* Sensu Lato. Clinical and vaccine immunology: CVI. 2014; 21(11): 1490-9.

39. Comstedt P, Hanner M, Schuler W, Meinke A, Lundberg U. Design and Development of a Novel Vaccine for Protection against Lyme Borreliosis. PloS one. 2014; 9(11): e113294.

40. Fletcher L D, Bernfield L, Barniak V, Farley J E, Howell A, Knauf M, et al. Vaccine Potential of the *Neisseria meningitidis* 2086 Lipoprotein. Infection and immunity. 2004; 72(4): 2088-100.

41. Masignani V, Comanducci M, Giuliani M M, Bambini S, Adu-Bobie J, Arico B, et al. Vaccination against *Neisseria meningitidis* using three variants of the lipoprotein GNA1870. The Journal of experimental medicine. 2003; 197(6): 789-99.

42. Koeberling O, Seubert A, Granoff D M. Bactericidal antibody responses elicited by a meningococcal outer membrane vesicle vaccine with overexpressed factor H-binding protein and genetically attenuated endotoxin. The Journal of infectious diseases. 2008; 198(2): 262-70.

43. van de Waterbeemd B, Streefland M, van der Ley P, Zomer B, van Dijken H, Martens D, et al. Improved OMV vaccine against *Neisseria meningitidis* using genetically engineered strains and a detergent-free purification process. Vaccine. 2010; 28(30): 4810-6.

44. Brightbill H D, Libraty D H, Krutzik S R, Yang R B, Belisle J T, Bleharski J R, et al. Host defense mechanisms triggered by microbial lipoproteins through toll-like receptors. Science. 1999; 285(5428): 732-6.

45. Thoma-Uszynski S, Stenger S, Takeuchi O, Ochoa M T, Engele M, Sieling P A, et al. Induction of direct antimicrobial activity through mammalian toll-like receptors. Science. 2001; 291(5508): 1544-7.

46. Okuda S, Tokuda H. Lipoprotein sorting in bacteria. Annual review of microbiology. 2011; 65: 239-59.

47. Schulze R J, Zuckert W R. *Borrelia burgdorferi* lipoproteins are secreted to the outer surface by default. Molecular microbiology. 2006; 59(5): 1473-84.

48. Mascioni A, Bentley B E, Camarda R, Dilts D A, Fink P, Gusarova V, et al. Structural Basis for the Immunogenic Properties of the Meningococcal Vaccine Candidate LP2086. The Journal of biological chemistry. 2009; 284(13): 8738-46.

49. Steere A C, Livey I. Lyme disease vaccines. Plotkin S A, Orenstein W A, editors. Saunders, Pa., USA2013.

50. Poland G A. Vaccines against Lyme disease: What happened and what lessons can we learn? Clinical infectious diseases: an official publication of the Infectious Diseases Society of America. 2011; 52 Suppl 3: s253-8.

51. Kumru O S. Surface localization determinants of *Borrelia burgdorferi* lipoproteins. Kansas: University of Kansas; 2011.

52. van der Ley P, Steeghs L, Hamstra H J, ten Hove J, Zomer B, van Alphen L. Modification of lipid A biosynthesis in *Neisseria meningitidis* lpxL mutants: influence on lipopolysaccharide structure, toxicity, and adjuvant activity. Infection and immunity. 2001; 69(10): 5981-90.

53. Horton R M, Hunt H D, Ho S N, Pullen J K, Pease L R. Engineering hybrid genes without the use of restriction enzymes: gene splicing by overlap extension. Gene. 1989; 77(1): 61-8.

54. Bos M P, Tefsen B, Geurtsen J, Tommassen J. Identification of an outer membrane protein required for the transport of lipopolysaccharide to the bacterial cell surface. Proceedings of the National Academy of Sciences of the United States of America. 2004; 101(25): 9417-22.
55. Schulze R J, Chen S, Kumru O S, Zuckert W R. Translocation of *Borrelia burgdorferi* surface lipoprotein OspA through the outer membrane requires an unfolded conformation and can initiate at the C-terminus. Molecular microbiology. 2010; 76(5): 1266-78.
56. Li H, Dunn J J, Luft B J, Lawson C L. Crystal structure of Lyme disease antigen outer surface protein A complexed with an Fab. Proceedings of the National Academy of Sciences of the United States of America. 1997; 94(8): 3584-9.
57. Oriente F, Scarlato V, Delany I. Expression of factor H binding protein of meningococcus responds to oxygen limitation through a dedicated FNR-regulated promoter. Journal of bacteriology. 2010; 192(3): 691-701.
58. Chen S, Zuckert W R. Probing the *Borrelia burgdorferi* surface lipoprotein secretion pathway using a conditionally folding protein domain. Journal of bacteriology. 2011; 193 (23): 6724-32.
59. Lee J S, Shin K S, Pan J G, Kim C J. Surface-displayed viral antigens on *Salmonella* carrier vaccine. Nature biotechnology. 2000; 18(6): 645-8.
60. Rizos K, Lattemann C T, Bumann D, Meyer T F, Aebischer T. Autodisplay: efficacious surface exposure of antigenic UreA fragments from *Helicobacter pylori* in *Salmonella* vaccine strains. Infection and immunity. 2003; 71(11): 6320-8.
61. Lee S J, Liang L, Juarez S, Nanton M R, Gondwe E N, Msefula C L, et al. Identification of a common immune signature in murine and human systemic Salmonellosis. Proceedings of the National Academy of Sciences of the United States of America. 2012; 109(13): 4998-5003.
62. Cote-Sierra J, Bredan A, Toldos C M, Stijlemans B, Brys L, Cornelis P, et al. Bacterial lipoprotein-based vaccines induce tumour necrosis factor-dependent type 1 protective immunity against *Leishmania major*. Infection and immunity. 2002; 70(1): 240-8.
63. Noinaj N, Easley N C, Oke M, Mizuno N, Gumbart J, Boura E, et al. Structural basis for iron piracy by pathogenic *Neisseria*. Nature. 2012; 483(7387): 53-8.
64. Steere A C, Livey I. Lyme disease vaccines. In: Plotkin S A, Orenstein W A, Offit P A, editors. Vaccines. 6th ed: Saunders, and imprint of Elsevier Inc.; 2013. p. 1122-32.
65. Probst C, Ott A, Scheper T, Meyer W, Stocker W, Komorowski L. N-terminal disulfide-bridging of *Borrelia* outer surface protein C increases its diagnostic and vaccine potentials. Ticks and tick-borne diseases. 2012; 3(1): 1-7.
66. Eicken C, Sharma V, Klabunde T, Owens R T, Pikas D S, Hook M, et al. Crystal structure of Lyme disease antigen outer surface protein C from *Borrelia burgdorferi*. The Journal of biological chemistry. 2001; 276(13): 10010-5.
67. Kumaran D, Eswaramoorthy S, Luft B J, Koide S, Dunn J J, Lawson C L, et al. Crystal structure of outer surface protein C (OspC) from the Lyme disease spirochete, *Borrelia burgdorferi*. The EMBO journal. 2001; 20(5): 971-8.
68. Buckles E L, Earnhart C G, Marconi R T. Analysis of antibody response in humans to the type A OspC loop 5 domain and assessment of the potential utility of the loop 5 epitope in Lyme disease vaccine development. Clinical and vaccine immunology: CVI. 2006; 13(10): 1162-5.
69. Earnhart C G, Buckles E L, Dumler J S, Marconi R T. Demonstration of OspC type diversity in invasive human lyme disease isolates and identification of previously uncharacterized epitopes that define the specificity of the OspC murine antibody response. Infection and immunity. 2005; 73(12): 7869-77.
70. Grizot S, Buchanan S K. Structure of the OmpA-like domain of RmpM from *Neisseria meningitidis*. Molecular microbiology. 2004; 51(4): 1027-37.
71. van der Voort E R, van der Ley P, van der Biezen J, George S, Tunnela O, van Dijken H, et al. Specificity of human bactericidal antibodies against PorA P1.7,16 induced with a hexavalent meningococcal outer membrane vesicle vaccine. Infection and immunity. 1996; 64(7): 2745-51.

The invention claimed is:

1. An OMV comprising a fusion lipoprotein, wherein the fusion lipoprotein comprises an N-terminal and a C-terminal fusion partner, wherein:
   (a) the N-terminal fusion partner comprises in N- to C-terminal order:
      i) a lipidated N-terminal cysteine;
      ii) a tether of a surface exposed lipoprotein of a Gram-negative bacterium; and, optionally,
      iii) a stretch of at least 5 contiguous amino acids that are located C-terminally of the tether of a surface exposed lipoprotein of a Gram-negative bacterium;
      wherein the N-terminal fusion partner causes presentation of the fusion lipoprotein on the extracellular outer membrane surface of a Gram-negative bacterium upon expression therein; and,
   (b) the C-terminal fusion partner comprises at least one epitope of an antigen associated with an infectious disease and/or a tumour,
   wherein the C-terminal fusion partner does not comprise an amino acid sequence of at least 10 contiguous amino acids from the surface exposed lipoprotein from which the sequence of the N-terminal fusion partner originates; and
   wherein the amino acid sequence of the fusion lipoprotein does not occur in nature.

2. The OMV according to claim 1, wherein the tether of the fusion lipoprotein is located adjacent to the lipidated N-terminal cysteine.

3. The OMV according to claim 1, wherein the N-terminal fusion partner of the fusion lipoprotein comprises an N-terminal fragment from a surface exposed lipoprotein of a Gram-negative bacterium and wherein the fragment causes surface expression of the fusion lipoprotein when expressed in the Gram-negative bacterium.

4. The OMV according to claim 1, wherein the tether of the fusion protein is of a Gram-negative bacterium of the genus *Neisseria*.

5. The OMV according to claim 3, wherein the surface exposed lipoprotein is selected from the group consisting of fHbp, LpbB, TbpB, NHBA and Ag473.

6. The OMV according to claim 1, wherein the N-terminal fusion partner of the fusion lipoprotein comprises at least one of:
   a) the amino acid sequence in positions 20-38 of SEQ ID NO: 1;
   b) the amino acid sequence in positions 21-61 or positions 21-63 of SEQ ID NO: 2; and,
   c) the amino acid sequence in positions 23-51 of SEQ ID NO: 3.

7. The OMV according to claim 6, wherein the N-terminal fusion partner of the fusion lipoprotein comprises at least one of:
   a) the amino acid sequence in positions 20-50 of SEQ ID NO: 1;
   b) the amino acid sequence in positions 21-73 or positions 21-75 of SEQ ID NO: 2; or,
   c) the amino acid sequence in positions 23-63 of SEQ ID NO: 3.

8. The OMV according to claim 1, wherein the C-terminal fusion partner of the fusion lipoprotein does not comprise a contiguous amino acid sequence of at least 5 amino acids from the surface exposed lipoprotein from which the sequence of the N-terminal fusion partner originates.

9. The OMV according to claim 8, wherein the C-terminal fusion partner of the fusion lipoprotein comprises surface exposed epitopes from a proteinaceous antigen of an infectious agent or tumour.

10. The OMV according to claim 9, wherein the C-terminal fusion partner of the fusion lipoprotein comprises a surface exposed domain of a surface exposed bacterial protein or lipoprotein.

11. The OMV according to claim 10, wherein the bacterial protein comprises a *Borrelia* surface lipoprotein selected from the group consisting of OspA, OspB, OspC, OspF, VlsE, BbCRASP1, Vsp1, P35 (BBK32), P37 (BBK50), P39, P66, DpbA and BB017.

12. The OMV according to claim 11, wherein the *Borrelia* surface lipoprotein comprises amino acids 29-273 of SEQ ID NO: 4, amino acids 29-273 of SEQ ID NO: 58 or amino acids 136-210 of SEQ ID NO: 59.

13. The OMV according to claim 1, wherein the OMV is not a detergent-extracted OMV.

14. The OMV according to claim 1, wherein the OMV is a supernatant OMV or a native OMV.

15. The OMV according to claim 1, wherein the OMV is obtainable from a Gram-negative bacterium that has one or more genetic modifications selected from the group consisting of:
   a) a genetic modification causing the bacterium to produce an LPS with reduced toxicity;
   b) genetic modification that increases vesicle formation; and,
   c) genetic modification that prevent proteolytic release of cell surface-exposed lipoprotein.

16. The OMV according to claim 15, wherein the Gram-negative bacterium belongs to a genus selected from the group consisting of *Neisseria, Bordetella, Escherichia* and *Salmonella*.

* * * * *